United States Patent
Andreotti et al.

(10) Patent No.: US 9,365,551 B2
(45) Date of Patent: *Jun. 14, 2016

(54) 2-(BENZYLOXY) BENZAMIDES AS LRRK2 KINASE INHIBITORS

(75) Inventors: Daniele Andreotti, Verona (IT); Xuedong Dai, Shanghai (CN); Andrew John Eatherton, Middlesex (GB); Karamjit Singh Jandu, Middlesex (GB); Qian Liu, Shanghai (CN); Oliver James Philps, Middlesex (GB)

(73) Assignee: Glaxo Group Limited, Brentford, Middlesex (GB)

(*) Notice: Subject to any disclaimer, the term of this patent is extended or adjusted under 35 U.S.C. 154(b) by 274 days.

This patent is subject to a terminal disclaimer.

(21) Appl. No.: 13/820,184

(22) PCT Filed: Aug. 31, 2011

(86) PCT No.: PCT/EP2011/064943
§ 371 (c)(1),
(2), (4) Date: May 10, 2013

(87) PCT Pub. No.: WO2012/028629
PCT Pub. Date: Mar. 8, 2012

(65) Prior Publication Data
US 2013/0225584 A1    Aug. 29, 2013

(30) Foreign Application Priority Data

Sep. 2, 2010   (WO) ............... PCT/CN2010/076557
Mar. 28, 2011  (WO) ............... PCT/CN2011/000511
Jul. 26, 2011  (WO) ............... PCT/CN2011/001227

(51) Int. Cl.
| | |
|---|---|
| *C07D 403/12* | (2006.01) |
| *C07D 213/75* | (2006.01) |
| *C07D 231/12* | (2006.01) |
| *C07D 237/20* | (2006.01) |
| *C07D 261/14* | (2006.01) |
| *C07D 295/192* | (2006.01) |
| *C07D 401/12* | (2006.01) |
| *C07D 413/12* | (2006.01) |

(52) U.S. Cl.
CPC ............ *C07D 403/12* (2013.01); *C07D 213/75* (2013.01); *C07D 231/12* (2013.01); *C07D 237/20* (2013.01); *C07D 261/14* (2013.01); *C07D 295/192* (2013.01); *C07D 401/12* (2013.01); *C07D 413/12* (2013.01)

(58) Field of Classification Search
CPC .. C07D 213/75; C07D 231/12; C07D 237/20; C07D 261/14; C07D 295/192; C07D 301/00; C07D 331/00; C07D 401/00; C07D 451/00; C07D 401/12; C07D 403/12; C07D 413/12
See application file for complete search history.

(56) References Cited

U.S. PATENT DOCUMENTS 5,236,931 A    8/1993  Jagdmann et al.

FOREIGN PATENT DOCUMENTS

| WO | WO2009/127642 | 10/2009 | |
|---|---|---|---|
| WO | WO 2011038572 A1 | * 4/2011 | |

OTHER PUBLICATIONS

Wermuth, The Practice of Medicinal Chemistry, 1996, Chapter 13, pp. 203-237.*
Patani et. al., Chemical Reviews, 1996, American Chemical Society, vol. 96, pp. 3147-3176.*
International Search Report for PCT/EP2011/064943 mailed Dec. 15, 2011.

* cited by examiner

*Primary Examiner* — Sarah Pihonak
(74) *Attorney, Agent, or Firm* — Fang Qian; William R. Majarian

(57) ABSTRACT

The present invention relates to novel compounds that inhibit LRRK2 kinase activity, processes for their preparation, to compositions containing them and to their use in the treatment of diseases characterized by LRRK2 kinase activity, for example Parkinson's disease or Alzheimer's disease.

14 Claims, No Drawings

2-(BENZYLOXY) BENZAMIDES AS LRRK2 KINASE INHIBITORS

This application is a 371 of International Application No, PCT/EP2011/064943, filed 31 Aug. 2011, which claims priority to PCT/CN/2011/001227 filed 26 Jul. 2011, PCT/CN2011/000511 filed 28 Mar. 2011 and PCT/CN2011/076557 filed 2 Sep. 2010.

FIELD OF THE INVENTION

The present invention relates to novel compounds that inhibit LRRK2 kinase activity, processes for their preparation, to compositions containing them and to their use in the treatment of diseases characterized by LRRK2 kinase activity, particularly Parkinson's disease and Alzheimer's disease.

BACKGROUND OF THE INVENTION

Parkinson's disease is a neurodegenerative disorder characterized by selective degeneration and cell death of dopaminergic neurones in the substantia nigra region of the brainstem. Parkinson's disease is generally considered to be sporadic and of unknown etiology. Over the past five years, however, a handful of mutations in the leucine rich repeat kinase 2 (LRRK2) gene have been linked to Parkinson's disease (WO2006068492 and WO2006045392). The G2019S mutation co-segregates with autosomal dominant parkinsonism and accounts for about 6% of familial Parkinson's disease cases and 3% of sporadic Parkinson's disease cases in Europe (Gilks et al., 2005, Lancet, 365: 415-416; Jaleel et al., 2007, Biochem J, 405: 307-317). LRRK2 is a member of the ROCO protein family and all members of this family share five conserved domains. The G2019S mutation occurs in the highly conserved kinase domain and it has therefore been postulated that the G2019S mutation may have an effect on kinase activity (WO2006068492). It has since been verified that this mutation increases the Vmax of LRRK2 for the non-natural, in vitro, substrates, moesin and the LRRKtide peptide (Jaleel et al., 2007, Biochem J, 405: 307-317). Amino acid substitutions at a second residue R1441 are also associated with Parkinson's Disease (reviewed in Paisan-Ruiz 2009, Hum. Mutat. 30: 1153-1160) and have also been shown to elevate LRRK2 kinase activity via decreasing the rate of GTP hydrolysis by the GTPase domain of LRRK2 (Guo et al., 2007 Exp Cell Res. 313: 3658-3670; West et al., 2007 Hum. Mol Gen. 16: 223-232). Over-expression of the mutant protein LRRK2 R1441G is reported to cause symptoms of Parkinson's disease and hyperphosphorylation of Tau in transgenic mouse models (Li, Y. et al. 2009, Nature Neuroscience 12: 826-828). This LRRK2 driven phenotype is also characterized by diminished dopamine release, suggesting that inhibitors of LRRK2 would be expected to positively regulate dopamine release. These data suggest that novel LRRK2 inhibitors of kinase catalytic activity could be useful for the treatment of Parkinson's disease, including idiopathic Parkinson's disease and familial Parkinson's disease, particularly familial Parkinson's disease in patients expressing LRRK2 kinase bearing the G2019S mutation or the R1441G mutation. In addition, LRRK2 inhibitors may have potential utility in treatment of other conditions characterized by diminished dopamine levels such as withdrawal symptoms/relapse associated with drug addiction (Rothman et al., 2008, Prog. Brain Res, 172: 385), and Tauopathy diseases characterized by hyperphosphorylation of Tau such as argyrophilic grain disease, Pick's disease, corticobasal degeneration, progressive supranuclear palsy and inherited frontotemporal dementia and parkinsonism linked to chromosome 17 (FTDP-17) (Goedert, M and Jakes, R (2005) Biochemica et Biophysica Acta 1739, 240-250).

Two further mutations in LRRK2 have been identified that are clinically associated with the transition from mild cognitive impairment (MCI) to Alzheimer's disease (WO2007149798). These data suggest that inhibitors of LRRK2 kinase activity could be useful for the treatment diseases such as Alzheimer's disease, other dementias and related neurodegenerative disorders.

In an experimental model of Parkinson's disease in marmosets an elevation of LRRK2 mRNA is observed in a manner that correlates with the level of L-Dopa induced dyskinesia (Hurley, M. J et al., 2007 Eur. J. Neurosci. 26: 171-177). This suggests that LRRK2 inhibitors may have utility in amelioration of such dyskinesias.

Evidence is also emerging of roles for LRRK2 in regulating neuronal progenitor differentiation in vitro (Milosevic, J. et al., 2009 Mol. Neurodegen. 4: 25), suggesting that inhibitors of LRRK2 may have utility in production of neuronal progenitor cells in vitro for consequent therapeutic application in cell based-treatment of CNS disorders.

Parkinson's disease patients bearing LRRK2 G2019S mutation have been reported to display increased frequency of non-skin cancers, including renal, breast, lung, prostate cancers as well as acute myelogenous leukemia (AML). Given that G2019S mutation in LRRK2 is reported to increase catalytic activity of the LRRK2 kinase domain, it is anticipated that there may be utility in small molecule inhibitors of LRRK2 for treatment of cancers, especially those of kidney, breast, lung, prostate (e.g. solid tumors) and blood (e.g. AML; Saunders-Pullman et al., 2010, Movement Disorders, 25:2536-2541). Amplification and overexpression of LRRK2 has also been reported in papillary renal and thyroid carcinomas, where co-operativity between LRRK2 and the MET oncogene may promote tumor cell growth and survival (Looyenga et al., 2011 PNAS 108: 1439-1444).

Meta-analysis of three genome wide associated scans for Crohn's disease identified a number of loci associated with the disease, including the locus containing the LRRK2 gene (Barrett et al., 2008, Nature Genetics, 40: 955-962). More recently, evidence has emerged suggesting that LRRK2 is an IFN-γ target gene that may be involved in signaling pathways relevant to Crohn's disease pathogenesis (Gardet et al., 2010, The Journal of Immunology, 185: 5577-5585). These findings suggest that inhibitors of LRRK2 may have utility in the treatment of Crohn's disease.

As an IFN-γ target gene LRRK2 may also play a role in T cell mechanisms that underlie other diseases of the immune system such as Multiple Sclerosis and rheumatoid arthritis. Further potential utility of LRRK2 inhibitors comes from the reported finding that B lymphocytes constitute a major population of LRRK2 expressing cells (Maekawa et al. 2010, BBRC 392: 431-435), This suggests that LRRK2 inhibitors may be effective in treatment of diseases of the immune system for which B cell depletion is, or may be, effective—such as lymphomas, leukemias, multiple sclerosis (Ray et al., 2011 J. Immunol. 230: 109), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies (Engel et al., 2011 Pharmacol. Rev. 63: 127-156; Homam et al., 2010 J. Clin. Neuromuscular Disease 12: 91-102)

SUMMARY OF THE INVENTION

The present invention provides, in a first aspect, a compound of formula (I) or a salt thereof:

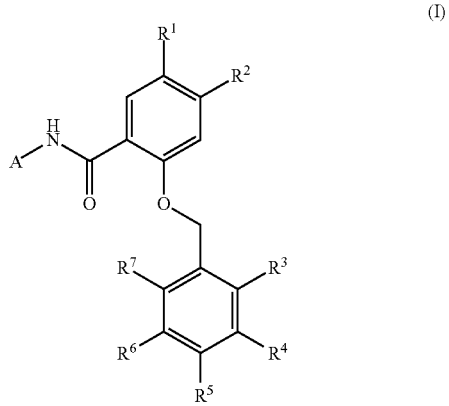

wherein:

A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

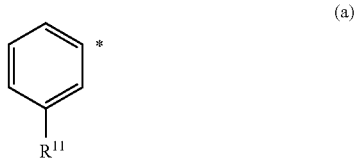

wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;

$R^1$ and $R^2$ independently represent halo, $C_{1-3}$ haloalkyl, —$(CH_2)_nR^8$, —$(CO)R^8$, nitrogen containing heteroaryl ring optionally substituted with one, two or three groups selected from methyl and trifluoromethyl;

n represents 1, 2 or 3;

$R^3$, $R^4$, $R^5$, $R^6$ and $R^7$ independently represent hydrogen, halo, CN, $C_{1-3}$alkyl or $C_{1-3}$alkoxy;

$R^8$ represents hydrogen or —$NR^9R^{10}$; $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl; and $R^{11}$ represents hydrogen, halo, CN, $C_{1-2}$alkyl, $C_{1-2}$alkoxy or —$CONHCH_3$.

The term 'halo' as used herein refers to a fluoro, chloro, bromo or iodo group.

The term '$C_{x-y}$ alkyl' as used herein refers to a linear or branched saturated hydrocarbon group containing from x to y carbon atoms. Examples of $C_{1-3}$ alkyl groups include methyl, ethyl, n-propyl and isopropyl.

The term '$C_{x-y}$ haloalkyl' as used herein refers to a $C_{x-y}$ alkyl group as defined herein wherein at least one hydrogen atom is replaced with halogen. Examples of such groups include fluoroethyl, trifluoromethyl or trifluoroethyl and the like.

The term '$C_{x-y}$ alkoxy' as used herein refers to a group of formula —O—$C_{x-y}$ alkyl, wherein $C_{x-y}$ alkyl is defined as above. Examples of $C_{1-3}$ alkoxy groups include methoxy, ethoxy, n-propoxy, and isopropoxy.

The term 'nitrogen containing monoheterocyclic ring' as used herein refers to a 4-7 membered monocyclic ring which may be saturated or partially unsaturated, and which contains at least one nitrogen atom. Optionally, the ring may contain 1 to 3 other heteroatoms selected from oxygen, nitrogen or sulphur. Examples of nitrogen containing heterocyclyl groups include pyrrolidinyl, azetidinyl, pyrazolidinyl, oxazolidinyl, imidazolidinyl, piperidinyl, piperazinyl, morpholinyl, thiomorpholinyl, thiazolidinyl, hydantoinyl, valerolactamyl, tetrahydropyridinyl, tetrahydropyrimidinyl, diazepanyl, azepanyl and the like.

The term 'nitrogen containing heteroaryl ring' as used herein refers to a 5-6 membered monocyclic aromatic ring which monocyclic aromatic ring contains at least one nitrogen atom. Optionally, the aromatic ring may contain 1 to 3 further heteroatoms selected from oxygen, nitrogen and sulphur. Examples of such monocyclic aromatic rings include, furazanyl, pyrrolyl, triazolyl, tetrazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl, pyridinyl, triazinyl, tetrazinyl and the like.

In one embodiment, the invention provides a compound of formula (I) or a salt thereof:

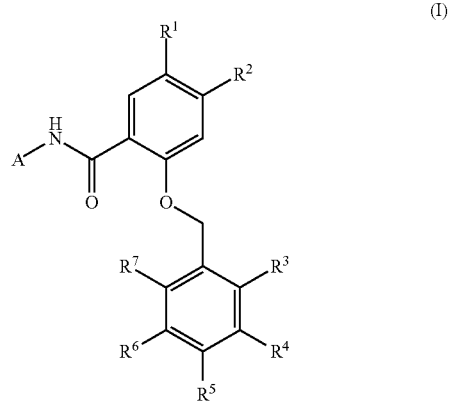

wherein:

A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl, wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;

$R^1$ and $R^2$ independently represent halo, $—(CH_2)_nR^8$, $—(CO)R^8$, nitrogen containing heteroaryl ring optionally substituted with one, two or three methyl groups;
n represents 1, 2 or 3;
$R^3$, $R^4$, $R^5$, $R^6$ and $R^7$ independently represent hydrogen, halo, CN, $C_{1-3}$alkyl or $C_{1-3}$alkoxy; and
$R^8$ represents hydrogen or $—NR^9R^{10}$; $R^9$ and $R^{19}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three methyl groups.

In further aspects of the invention, the invention provides a pharmaceutical composition comprising the compound of formula (I) or a pharmaceutically acceptable salt thereof and a pharmaceutically acceptable carrier and medical uses of the compound of formula (I) or pharmaceutically acceptable salt thereof.

DETAILED DESCRIPTION OF THE INVENTION

As discussed above, in a first aspect, the invention provides a compound of formula (I) or a salt thereof:

(I)

wherein:
A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

(a)

wherein when A represents pyridin-3-yl, the pyridinyl ring may optionally be substituted at the 2 position by fluoro, methoxy or $CH_2OH$, at the 4 position by methyl or $CH_2OH$, or at the position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;

$R^1$ and $R^2$ independently represent halo, $C_{1-3}$ haloalkyl, $—(CH_2)_nR^8$, $—(CO)R^8$, nitrogen containing heteroaryl ring optionally substituted with one, two or three groups selected from methyl and trifluoromethyl;
n represents 1, 2 or 3;
$R^3$, $R^4$, $R^5$, $R^6$ and $R^7$ independently represent hydrogen, halo, CN, $C_{1-3}$alkyl or $C_{1-3}$alkoxy;
$R^8$ represents hydrogen or $—NR^9R^{10}$; $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl; and
$R^{11}$ represents hydrogen, halo, CN, $C_{1-2}$alkyl, $C_{1-2}$alkoxy or $—CONHCH_3$.

In some embodiments, $R^1$ represents halo. In other embodiments, $R^1$ represents bromo or chloro. In one embodiment, $R^1$ represents bromo.

In some embodiments, $R^1$ represents $C_{1-3}$ haloalkyl. In other embodiments, $R^1$ represents trifluoromethyl.

In some embodiments, $R^1$ represents $—(CH_2)_nR^8$ wherein n is 1, 2 or 3 and $R^8$ represents hydrogen or $—NR^9R^{10}$. In other embodiments, $R^1$ represents $—(CH_2)_nR^8$ wherein n is 1 and $R^8$ represents hydrogen or $—NR^9R^{10}$.

In some embodiments, $R^1$ represents $—(CH_2)_nR^8$ wherein n is 1 and $R^8$ represents hydrogen.

In other embodiments, $R^1$ represents $—(CH_2)_nR^8$ wherein n is 1, 2 or 3 and $R^8$ represents $—NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl. In some embodiments, $R^1$ represents $—(CH_2)_nR^8$ wherein n is 1, 2 or 3 and $R^8$ represents $—NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three methyl groups. In some embodiments, $R^1$ represents $—(CH_2)_nR^8$ wherein n is 1 and $R^8$ represents $—NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl. In other embodiments, $R^1$ represents $—(CH_2)_nR^8$ wherein n is 1 and $R^8$ represents $—NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three methyl groups. In some embodiments, $R^1$ represents 4-morpholinylmethyl, 1-piperidinylmethyl or 1-pyrrolidinyl-methyl wherein the morpholinyl, piperidinyl or pyrrolidinyl ring is optionally substituted with one, two or three groups selected from halo, methyl and trifluoromethyl. In other embodiments, $R^1$ represents 4-morpholinylmethyl.

In some embodiments, $R^1$ represents —(CO)$R^8$ and $R^8$ represents —$NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl. In some embodiments, $R^1$ represents —(CO)$R^8$ and $R^8$ represents —$NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three methyl groups. In some embodiments, $R^1$ represents 4-morpholinylcarbonyl, 1-piperidinylcarbonyl or 1-pyrrolidinylcarbonyl wherein the morpholinyl, piperidinyl or pyrrolidinyl ring is optionally substituted with one, two or three groups selected from halo, methyl and trifluoromethyl. In other embodiments, $R^1$ represents 4-morpholinylcarbonyl.

In certain embodiments in which $R^1$ represents —(CH$_2$)$_n R^8$ or —(CO)$R^8$, $R^9$ and $R^{10}$ are either independently selected from hydrogen and $C_{1-3}$ alkyl. In other embodiments in which $R^1$ represents —(CH$_2$)$_n R^8$ or —(CO)$R^8$, $R^9$ and $R^{10}$, together with the nitrogen atom to which they are attached, join together to form a nitrogen containing monoheterocyclic ring which ring is optionally substituted with one, two or three groups selected from halo, methyl and trifluoromethyl. In certain embodiments in which $R^1$ represents —(CH$_2$)$_n R^8$ or —(CO)$R^8$, $R^9$ and $R^{10}$, together with the nitrogen atom to which they are attached, join together to form a nitrogen containing monoheterocyclic ring which ring is optionally substituted with one, two or three methyl groups. In some embodiments, —$NR^9R^{10}$ represents morpholinyl, piperidinyl or pyrrolidinyl, which rings are optionally substituted with one, two or three groups selected from halo, methyl and trifluoromethyl. In other embodiments, —$NR^9R^{10}$ represents unsubstituted morpholinyl.

In a further embodiment, $R^1$ represents a nitrogen containing heteroaryl ring optionally substituted with one, two or three groups selected from methyl and trifluoromethyl. In some embodiments, $R^1$ represents a nitrogen containing heteroaryl ring optionally substituted with one, two or three methyl groups. In other embodiments, $R^1$ represents pyrazolyl optionally substituted with one, two or three groups selected from methyl or trifluoromethyl. In some embodiments, $R^1$ represents pyrazolyl optionally substituted with one, two or three methyl groups. In other embodiments, $R^1$ represents pyrazolyl optionally substituted with one methyl group. In some embodiments, $R^1$ represents pyrazol-4-yl optionally substituted with one methyl group, such as 1-methylpyrazol-4-yl.

In some embodiments, this invention also relates to compounds of any of the above embodiments, wherein $R^2$ represents halo. In other embodiments, this invention also relates to compounds of any of the above embodiments, wherein $R^2$ represents chloro or bromo. In some embodiments, this invention also relates to compounds of any of the above embodiments, wherein $R^2$ represents bromo.

In some embodiments, this invention also relates to compounds of any of the above embodiments, wherein $R^2$ represents $C_{1-3}$ haloalkyl. In other embodiments, this invention also relates to compounds of any of the above embodiments, wherein $R^2$ represents trifluoromethyl.

In another embodiment, this invention also relates to compounds of any of the above embodiments, wherein $R^2$ represents —(CH$_2$)$_n R^8$ wherein n is 1, 2 or 3 and $R^8$ represents hydrogen or —$NR^9R^{10}$. In some embodiments, this invention also relates to compounds of any of the above embodiments, wherein $R^2$ represents —(CH$_2$)$_n R^8$ wherein n is 1 and $R^8$ represents hydrogen or —$NR^9R^{10}$.

In some embodiments, this invention also relates to compounds of any of the above embodiments, wherein $R^2$ represents —(CH$_2$)$_n R^8$ wherein n is 1 and $R^8$ represents hydrogen.

In other embodiments, this invention also relates to compounds of any of the above embodiments, wherein $R^2$ represents —(CH$_2$)$_n R^8$ wherein n is 1, 2 or 3 and $R^8$ represents —$NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl. In one embodiment, this invention also relates to compounds of any of the above embodiments, wherein $R^2$ represents —(CH$_2$)$_n R^8$ wherein n is 1, 2 or 3 and $R^8$ represents —$NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three methyl groups. In some embodiments, this invention also relates to compounds of any of the above embodiments, wherein $R^2$ represents —(CH$_2$)$_n R^8$ wherein n is 1 and $R^8$ represents —$NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl. In some embodiments, this invention also relates to compounds of any of the above embodiments, wherein $R^2$ represents —(CH$_2$)$_n R^8$ wherein n is 1 and $R^8$ represents —$NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three methyl groups. In some embodiments, this invention also relates to compounds of any of the above embodiments, wherein $R^2$ represents 4-morpholinylmethyl, 1-piperidinylmethyl or 1-pyrrolidinylmethyl wherein the morpholinyl, piperidinyl or pyrrolidinyl ring is optionally substituted with one, two or three groups selected from halo, methyl and trifluoromethyl. In other embodiment, this invention also relates to compounds of any of the above embodiments, wherein $R^2$ represents 4-morpholinylmethyl.

In a further embodiment, this invention also relates to compounds of any of the above embodiments, wherein $R^2$ represents —(CO)$R^8$ and $R^8$ represents —$NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl. In some embodiments, this invention also relates to compounds of any of the above embodiments, wherein $R^2$ represents —(CO)$R^8$ and $R^8$ represents —$NR^9R^{10}$ wherein $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three methyl groups. In some embodiments, this invention also relates to compounds of any of the above embodiments, wherein $R^2$ represents 4-morpholinylcarbonyl, 1-piperidinylcarbonyl or 1-pyrrolidinylcarbonyl, wherein the morpholinyl, piperidinyl or pyrrolidinyl ring is optionally substituted with one, two or three groups selected from halo, methyl and trifluoromethyl. In other embodiments, this invention also relates to compounds of any of the above embodiments, wherein $R^2$ represents 4-morpholinylcarbonyl, 1-piperidinylcarbonyl or 1-pyrrolidinylcarbonyl wherein the morpholinyl, piperidinyl or pyrrolidinyl ring is optionally substituted with one, two or three groups selected from halo, methyl and trifluoromethyl. In some embodiments, this invention also relates to compounds of any of the above embodiments, wherein $R_2$ represents 1-piperidinylcarbonyl or 1-piperidinylmethyl. In other embodiments, this invention also relates to compounds of any of the above embodiments, wherein $R_2$ represents 1-pyrrolidinylcarbonyl optionally substituted with one or more fluoro group. In some embodiments, this invention also relates to compounds of any of the above embodiments, wherein $R^2$ represents 4-morpholinylcarbonyl. In another embodiment, $R_2$ represents —C(=O)N(CH$_3$)$_2$.

In certain embodiments, this invention also relates to compounds of any of the above embodiments, wherein $R^2$ represents —(CH$_2$)$_n$$R^8$ or —(CO)$R^8$, $R^9$ and $R^{10}$ are either independently selected from hydrogen and $C_{1-3}$ alkyl. In other embodiments in which $R^2$ represents —(CH$_2$)$_n$$R^8$ or —(CO)$R^8$, $R^9$ and $R^{10}$, together with the nitrogen atom to which they are attached, join together to form a nitrogen containing monoheterocyclic ring which ring is optionally substituted with one, two or three groups selected from halo, methyl and trifluoromethyl. In certain embodiments in which $R^2$ represents —(CH$_2$)$_n$$R^8$ or —(CO)$R^8$, $R^9$ and $R^{10}$, together with the nitrogen atom to which they are attached, join together to form a nitrogen containing monoheterocyclic ring which ring is optionally substituted with one, two or three methyl groups. In some embodiments, —$NR^9R^{10}$ represents morpholinyl, piperidinyl or pyrrolidinyl, which rings are optionally substituted with one, two or three groups selected from halo, methyl and trifluoromethyl. In some embodiments, —$NR^9R^{10}$ represents unsubstituted morpholinyl.

In a further embodiment, this invention also relates to compounds of any of the above embodiments, wherein $R^2$ represents a nitrogen containing heteroaryl ring optionally substituted with one, two or three groups selected from methyl and trifluoromethyl. In some embodiments, this invention also relates to compounds of any of the above embodiments, wherein $R^2$ represents a nitrogen containing heteroaryl ring optionally substituted with one, two or three methyl groups. In other embodiments, this invention also relates to compounds of any of the above embodiments, wherein $R^2$ represents pyrazolyl optionally substituted with one, two or three groups selected from methyl and trifluoromethyl. In some embodiments, this invention also relates to compounds of any of the above embodiments, wherein $R^2$ represents pyrazolyl optionally substituted with one, two or three methyl groups. In other embodiments, this invention also relates to compounds of any of the above embodiments, wherein $R^2$ represents pyrazolyl optionally substituted with one methyl group. In some embodiments, this invention also relates to compounds of any of the above embodiments, wherein $R^2$ represents pyrazol-4-yl optionally substituted with one methyl group, such as 1-methylpyrazol-4-yl.

In some embodiments, this invention also relates to compounds of any of the above embodiments, wherein one of $R^1$ and $R^2$ represents a nitrogen containing heteroaryl ring optionally substituted with one, two or three groups selected from methyl and trifluoromethyl and the other of $R^1$ and $R^2$ represents either —(CO)$R^8$ or —(CH$_2$)$_n$$R^8$ wherein n is 1, 2 or 3 and $R^8$ represents —$NR^9R^{10}$. In some embodiments, this invention also relates to compounds of any of the above embodiments, wherein one of $R^1$ and $R^2$ represents a nitrogen containing heteroaryl ring optionally substituted with one, two or three methyl groups and the other of $R^1$ and $R^2$ represents either —(CO)$R^8$ or —(CH$_2$)$_n$$R^8$ wherein n is 1, 2 or 3 and $R^8$ represents —$NR^9R^{10}$. In other embodiments, this invention also relates to compounds of any of the above embodiments, wherein one of $R^1$ and $R^2$ represents a nitrogen containing heteroaryl ring optionally substituted with one, two or three methyl groups and the other of $R^1$ and $R^2$ represents either —(CO)$R^8$ or —(CH$_2$)$_n$$R^8$ wherein n is 1 and $R^8$ represents —$NR^9R^{10}$. In some embodiments, this invention also relates to compounds of any of the above embodiments, wherein one of $R^1$ and $R^2$ represents a nitrogen containing heteroaryl ring optionally substituted with one methyl group and the other of $R^1$ and $R^2$ represents either —(CO)$R^8$ or —(CH$_2$)$_n$$R^8$ wherein n is 1 and $R^8$ represents —$NR^9R^{10}$. In other embodiments, this invention also relates to compounds of any of the above embodiments, wherein one of $R^1$ and $R^2$ represents pyrazolyl optionally substituted with one methyl group, particularly pyrazol-4-yl optionally substituted with one methyl group, such as 1-methylpyrazol-4-yl and the other of $R^1$ and $R^2$ represents either —(CO)$R^8$ or —(CH$_2$)$_n$$R^8$ wherein n is 1 and $R^8$ represents —$NR^9R^{10}$ wherein $R^9$ and $R^{10}$ are either independently selected from hydrogen and $C_{1-3}$ alkyl, or, together with the nitrogen atom to which they are attached, join together to form a nitrogen containing monoheterocyclic ring which ring is optionally substituted with one, two or three groups selected from halo, methyl and trifluoromethyl. In some embodiments, this invention also relates to compounds of any of the above embodiments, wherein one of $R^1$ and $R^2$ represents pyrazolyl optionally substituted with one methyl group. In other embodiments, this invention also relates to compounds of any of the above embodiments, wherein one of $R^1$ and $R^2$ represents pyrazol-4-yl optionally substituted with one methyl group, such as 1-methylpyrazol-4-yl and the other of $R^1$ and $R^2$ represents either —(CO)$R^8$ or —(CH$_2$)$_n$$R^8$ wherein n is 1 and $R^8$ represents —$NR^9R^{10}$ wherein $R^9$ and $R^{10}$ are either independently selected from hydrogen and $C_{1-3}$ alkyl, or, together with the nitrogen atom to which they are attached, join together to form a nitrogen containing monoheterocyclic ring which ring is optionally substituted with one, two or three methyl groups. In some embodiments, this invention also relates to compounds of any of the above embodiments, wherein one of $R^1$ and $R^2$ represents pyrazolyl optionally substituted with one methyl group, particularly pyrazol-4-yl optionally substituted with one methyl group, such as 1-methylpyrazol-4-yl and the other of $R^1$ and $R^2$ represents either —(CO)$R^8$ or —(CH$_2$)$_n$R$^8$ wherein n is 1 and R$^8$ represents —NR$^9$R$^{10}$ wherein R$^9$ and R$^{10}$, together with the nitrogen atom to which they are attached, join together to form a nitrogen containing monoheterocyclic ring which ring is optionally substituted with one, two or three groups selected from halo, methyl and trifluoromethyl. In one embodiment, one of R$^1$ and R$^2$ represents pyrazolyl optionally substituted with one methyl group, particularly pyrazol-4-yl optionally substituted with one methyl group, such as 1-methylpyrazol-4-yl and the other of R$^1$ and R$^2$ represents either —(CO)R$^8$ or —(CH$_2$)$_n$R$^8$ wherein n is 1 and R$^8$ represents —NR$^9$R$^{10}$ wherein R$^9$ and R$^{10}$, together with the nitrogen atom to which they are attached, join together to form a nitrogen containing monoheterocyclic ring which ring is optionally substituted with one, two or three methyl groups, such as unsubstituted morpholinyl.

In some embodiments, this invention also relates to compounds of any of the above embodiments, wherein A represents:
pyridin-3-yl, wherein the pyridinyl ring may optionally be substituted at the 2 position by fluoro;
pyridazin-4-yl;
1H-pyrazol-4-yl, wherein the pyrazolyl ring may optionally be substituted at the 1 position by methyl; or
isoxazol-4-yl, wherein the isoxazolyl ring may optionally be substituted at the 3 position by methyl or at the 5 position by methyl.

In other embodiments, this invention also relates to compounds of any of the above embodiments, wherein A represents unsubstituted pyridin-3-yl.

In other embodiments, this invention also relates to compounds of any of the above embodiments, wherein A represents unsubstituted pyridazin-4-yl.

In an alternative embodiment, this invention also relates to compounds of any of the above embodiments, wherein A represents a group of formula (a).

In other embodiments, this invention also relates to compounds of any of the above embodiments, wherein A represents phenyl.

In some embodiments, this invention also relates to compounds of any of the above embodiments, wherein R$^{11}$ represents:
hydrogen;
halo (e.g. fluoro, chloro);
CN;
C$_{1-2}$alkyl (e.g. methyl, ethyl);
C$_{1-2}$alkoxy (e.g. methoxy); or
—CONHCH$_3$.

In other embodiments, this invention also relates to compounds of any of the above embodiments, wherein R$^{11}$ represents hydrogen, halo (e.g. fluoro chloro), CN, C$_{1-2}$alkyl (e.g. methyl, ethyl) or C$_{1-2}$alkoxy (e.g. methoxy). In some embodiments, this invention also relates to compounds of any of the above embodiments, wherein R$^{11}$ represents hydrogen, chloro, CN, methyl and methoxy. In some embodiments, this invention also relates to compounds of any of the above embodiments, wherein R$^{11}$ represents chloro.

In some embodiments, this invention also relates to compounds of any of the above embodiments, wherein R$^3$, R$^4$, R$^5$, R$^6$ and R$^7$ independently represent hydrogen or fluoro. In other embodiments, this invention also relates to compounds of any of the above embodiments, wherein one or two of R$^3$, R$^4$, R$^5$, R$^6$ and R$^7$ represent fluoro and the remaining groups represent hydrogen.

In some embodiments, this invention also relates to compounds of any of the above embodiments, wherein R$^3$, R$^4$, R$^5$, R$^6$ and R$^7$ each represent hydrogen.

In an alternative embodiment, this invention also relates to compounds of any of the above embodiments, wherein R$^4$, R$^5$, R$^6$ and R$^7$ each represent hydrogen and R$^3$ represents fluoro.

In another embodiment, this invention also relates to compounds of any of the above embodiments, wherein R$^3$, R$^5$, R$^6$ and R$^7$ each represent hydrogen and R$^4$ represents fluoro.

In yet other embodiments, this invention also relates to compounds of any of the above embodiments, wherein R$^3$, R$^4$, R$^6$ and R$^7$ each represent hydrogen and R$^5$ represents fluoro.

In a further embodiment, this invention also relates to compounds of any of the above embodiments, wherein R$^4$, R$^6$ and R$^7$ each represent hydrogen, and R$^3$ and R$^5$ each represent fluoro.

In a further embodiment, this invention also relates to compounds of any of the above embodiments, wherein R$^3$, R$^6$ and R$^7$ each represent hydrogen, and R$^4$ and R$^5$ each represent fluoro.

Compounds of formula (I) or salts thereof include the compounds of examples 1-53 or salts thereof. In one embodiment, compounds of formula (I) or salts thereof include the compounds of examples 1-7, 9-28 and 30-46, or salts thereof.

In one embodiment, the compound of formula (I) is not:
2-{[(4-fluorophenyl)methyl]oxy}-4-(1-methyl-1H-pyrazol-4-yl)-5-(4-morpholinylcarbonyl)-N-4-pyridazinylbenzamide or a salt thereof.

In one embodiment, the compound of formula (I) is not:
2-{[(2,4-Difluorophenyl)methyl]oxy}-N-(3-methyl-4-isoxazolyl)-5-(1-methyl-1H-pyrazol-4-yl)-4-(4-morpholinylmethyl)benzamide or a salt thereof.

In one embodiment, the compound of formula (I) is not:
4-Methyl-5-(1-methyl-1H-pyrazol-4-yl)-2-[(phenylmethyl)oxy]-N-4-pyridazinylbenzamide or a salt thereof.

In one embodiment, compounds of formula (I) include:
2-{[(4-fluorophenyl)methyl]oxy}-5-(1-methyl-1H-pyrazol-4-yl)-4-(4-morpholinylcarbonyl)-N-3-pyridinylbenzamide or salts thereof.

In one embodiment, compounds of formula (I) include:
2-{[(4-Fluorophenyl)methyl]oxy}-5-(1-methyl-1H-pyrazol-4-yl)-4-(4-morpholinylcarbonyl)-N-4-pyridazinylbenzamide or salts thereof.

In one embodiment, compounds of formula (I) include:

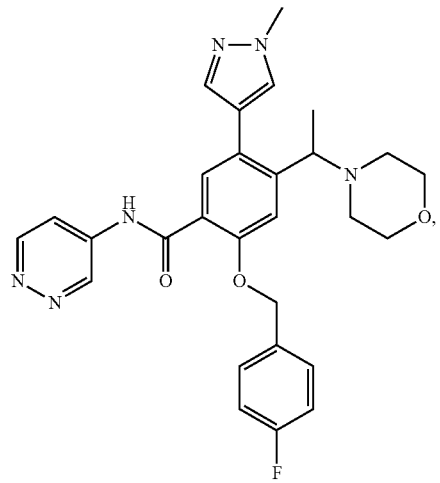 [SMILES: CC(c1cc(OCc2ccc(F)cc2)c(C(=O)Nc2ccnnc2)cc1-c1cnn(C)c1)N1CCOCC1]

or a salt thereof.

In one embodiment, compounds of formula (I) include:

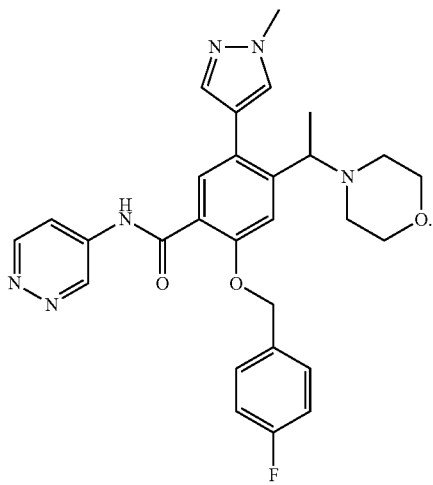 [SMILES: CC(c1cc(OCc2ccc(F)cc2)c(C(=O)Nc2ccnnc2)cc1-c1cnn(C)c1)N1CCOCC1]

Certain compounds of formula (I) are capable of forming salts. For example, the compounds of formula (I) wherein A represents optionally substituted pyridinyl or pyridazinyl rings can form acid addition salts. Such salts can be formed by reaction with the appropriate acid, optionally in a suitable solvent such as an organic solvent, to give the salt which may be isolated for example by crystallisation and filtration. Where A represents a group of formula (a) and $R^{11}$ represents —$CH_2CO_2H$, the compounds of formula (I) may form basic salts. Such salts may be formed by reacting with the appropriate base, optionally in a suitable solvent such as an organic solvent, to give the salt which may be isolated for example by crystallisation and filtration.

Because of their potential use in medicine, the salts of the compound of formula (I) are pharmaceutically acceptable.

Pharmaceutically acceptable acid addition salts of the compounds of formula (I) include sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate, adipate, bicarbonate/carbonate, bisulphate/sulphate, borate, camsylate, citrate, cyclamate, disylate, esylate, formate, gluceptate, gluconate, glucuronate, hexafluorophosphate, hibenzate, hydrochloride/chloride, hydrobromide/bromide, hydroiodide/iodide, isethionate, maleate, maleic acid, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts.

Pharmaceutically acceptable base addition salts of the compounds of formula (I) include metal salts (such as sodium, lithium, potassium, aluminium, calcium, magnesium and zinc) and ammonium salts (such as isopropylamine, diethylamine, diethanolamine salts).

The invention includes within its scope all possible stoichiometric and non-stoichiometric forms of the salts of the compounds of formula (I).

Certain compounds of formula (I) or salts thereof may exist in the form of solvates (e.g. hydrates).

Certain compounds of formula (I) are capable of existing in stereoisomeric forms. It will be understood that the invention encompasses all geometric and optical isomers of these compounds and the mixtures thereof including racemates. The different stereoisomeric forms may be separated one from the other by methods known in the art (e.g. separation by chiral HPLC), or any given isomer may be obtained by stereospecific or asymmetric synthesis. The invention also extends to any tautomeric forms and mixtures thereof. The invention also includes isotopically-labelled compounds and salts, which are identical to compounds of formula (I) or salts thereof, but for the fact that one or more atoms are replaced by an atom having an atomic mass or mass number different from the atomic mass or mass number most commonly found in nature. Examples of isotopes that can be incorporated into compounds of formula (I) or salts thereof isotopes of hydrogen, carbon, nitrogen, fluorine, such as $^3H$, $^{11}C$, $^{14}C$ and $^{18}F$. Such isotopically-labelled compound of formula (I) or salts thereof are useful in drug and/or substrate tissue distribution assays. For example, $^{11}C$ and $^{18}F$ isotopes are particularly useful in PET (positron emission tomography). PET is useful in brain imaging. Isotopically labelled compounds of formula (I) and salts thereof can generally be prepared by carrying out the procedures disclosed below, by substituting a readily available isotopically labelled reagent for a non-isotopically labelled reagent. In one embodiment, compounds of formula (I) or salts thereof are not isotopically labelled.

Certain compounds of formula (I) or salts thereof may exist in solid or liquid form. In the solid state, compounds of formula (I) or salts may exist in crystalline or noncrystalline form, or as a mixture thereof. For compounds of formula (I) or salts that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing vaiable amounts of water. The invention includes all such solvates.

The skilled artisan will further appreciate that certain compounds of formula (I) or salts thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. The invention includes all such polymorphs.

Compounds of formula (I) or pharmaceutically acceptable salts thereof are inhibitors of LRRK2 kinase activity and are thus believed to be of potential use in the treatment of neurological disorders. Exemplary neurological disorders include, but are not limited to, Parkinson's disease, Alzheimer's disease, dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies.

One aspect of the invention provides compounds of formula (I) or pharmaceutically acceptable salts thereof for use in therapy. In some embodiments, the invention provides compounds of formula (I) or pharmaceutically acceptable salts thereof for use in the treatment or prophylaxis of Parkinson's disease.

A further aspect of the invention provides use of compounds of formula (I) or pharmaceutically acceptable salts thereof in the manufacture of a medicament for the treatment of or prophylaxis of Parkinson's disease.

Another aspect of the invention provides methods of treatment of Parkinson's disease, which comprises administering to a host in need thereof an effective amount of a compound of formula (I) or a pharmaceutically acceptable salt thereof. In some embodiment, the host is human.

In the context of the present invention, treatment of Parkinson's disease refers to the treatment of idiopathic Parkinson's disease and/or familial Parkinson's disease. In one embodiment, familial Parkinson's disease includes patients expressing LRRK2 kinase bearing the G2019S mutation or the R1441G mutation. Treatment of Parkinson's disease may be symptomatic or may be disease modifying. In one embodiment, treatment of Parkinson's disease refers to symptomatic treatment.

Compounds of the present invention may also be useful in treating patients identified as susceptible to progression to severe Parkinsonism by means of one of more subtle features associated with disease progression such as family history, olfaction deficits, constipation, cognitive defects, gait or biological indicators of disease progression gained from molecular, biochemical, immunological or imaging technologies. In this context, treatment may be symptomatic or disease modifying.

In the context of the present invention, treatment of Alzheimer's disease refers to the treatment of idiopathic Alzheimer's disease and/or familial Alzheimer's disease. Treatment of Alzheimer's disease may be symptomatic or may be disease modifying. In one embodiment, treatment of Alzheimer's disease refers to symptomatic treatment. Similarly, treatment of dementia (including Lewy body dementia and vascular dementia), age related memory dysfunction, mild cognitive impairment argyrophilic grain disease, Pick's disease, corticobasal degeneration, progressive supranuclear palsy, inherited frontotemporal dementia and parkinsonism linked to chromosome 17 (FTDP-17), Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies may be symptomatic or disease modifying. In some embodiments, treatment of dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies refers to symptomatic treatment.

In the context of the present invention, treatment of withdrawal symptoms/relapse associated with drug addiction and L-Dopa induced dyskinesia refers to symptomatic treatment.

In a further aspect, the invention provides a compound of formula (I) or a pharmaceutically acceptable salt thereof wherein A, n, $R^1$, $R^2$, $R^3$, $R^4$, $R^5$, $R^6$, $R^7$, $R^8$, $R^9$, $R^{10}$, $R^{11}$ and n are as defined above for use in the treatment of the above disorders, for example Parkinson's disease or Alzheimer's disease. In some embodiments, the invention provides a compound of formula (I) or a pharmaceutically acceptable salt thereof wherein A, n, $R^1$, $R^2$, $R^3$, $R^4$, $R^5$, $R^6$, $R^7$, $R^8$, $R^9$, $R^{10}$, $R^{11}$ and n are as defined above for use in the prophylaxis of Parkinson's disease, Alzheimer's disease, of dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia or parkinsonism linked to chromosome 17 (FTDP-17), or renal, breast, lung, prostate cancers as well as acute myelogenous leukemia (AML). In one embodiment, the invention provides a compound of formula (I) or a pharmaceutically acceptable salt thereof wherein A, n, $R^1$, $R^2$, $R^3$, $R^4$, $R^5$, $R^6$, $R^7$, $R^8$, $R^9$, $R^{10}$, $R^{11}$ and n are as defined above for use in the prophylaxis of Parkinson's disease or Alzheimer's disease.

The invention further provides a method of treatment of the above disorders, for example Parkinson's disease or Alzheimer's disease, in mammals including humans, which comprises administering to a subject in need thereof a therapeutically effective amount of a compound of formula (I) or a pharmaceutically acceptable salt thereof wherein A, n, $R^1$, $R^2$, $R^3$, $R^4$, $R^5$, $R^6$, $R^7$, $R^8$, $R^9$, $R^{10}$, $R^{11}$ and n are as defined above.

The invention also provides the use of the compound of formula (I) or a pharmaceutically acceptable salt thereof wherein A, n, $R^1$, $R^2$, $R^3$, $R^4$, $R^5$, $R^6$, $R^7$, $R^8$, $R^9$, $R^{10}$, $R^{11}$ and n are as defined above in the manufacture of a medicament for use in the treatment of the above disorders, for example, Parkinson's disease or Alzheimer's disease. The invention also provides the use of the compound of formula (I) or a pharmaceutically acceptable salt thereof wherein A, n, $R^1$, $R^2$, $R^3$, $R^4$, $R^5$, $R^6$, $R^7$, $R^8$, $R^9$, $R^{10}$, $R^{11}$ and n are as defined above in the manufacture of a medicament for use in the prophylaxis of Parkinson's disease, Alzheimer's disease, dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia or parkinsonism linked to chromosome 17 (FTDP-17), or renal, breast, lung, prostate cancers as well as acute myelogenous leukemia (AML). In some embodiments, the invention provides the use of the compound of formula (I) or a pharmaceutically acceptable salt thereof wherein A, n, $R^1$, $R^2$, $R^3$, $R^4$, $R^5$, $R^6$, $R^7$, $R^8$, $R^9$, $R^{10}$, $R^{11}$ and n are as defined above in the manufacture of a medicament for use in the prophylaxis of Parkinson's disease or Alzheimer's disease.

The invention also provides the use of inhibitors of LRRK2 in the production of neuronal progenitor cells in vitro for consequent therapeutic application in cell based-treatment of CNS disorders.

When used in therapy, a compound of formula (I) or pharmaceutically acceptable salt thereof is usually formulated in a standard pharmaceutical composition. Such compositions can be prepared using standard procedures.

The present invention further provides a pharmaceutical composition which comprises the compound of formula (I) or a pharmaceutically acceptable salt thereof and a pharmaceutically acceptable carrier.

When a compound of formula (I) or a pharmaceutically acceptable salt thereof is intended for use in the treatment of Parkinson's disease, it may be used in combination with medicaments claimed to be useful as symptomatic treatments of Parkinson's disease. Suitable examples of such other therapeutic agents include L-dopa, and dopamine agonists (e.g. pramipexole, ropinirole).

When a compound of formula (I) or a pharmaceutically acceptable salt thereof is intended for use in the treatment of Alzheimer's disease, it may be used in combination with medicaments claimed to be useful as either disease modifying or symptomatic treatments of Alzheimer's disease. Suitable examples of such other therapeutic agents may be symptomatic agents, for example those known to modify cholinergic transmission such as M1 muscarinic receptor agonists or allosteric modulators, M2 muscarinic antagonists, acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-$HT_4$ receptor partial agonists, 5-$HT_6$ receptor antagonists or 5HT1A receptor antagonists and NMDA receptor antagonists or modulators, or disease modifying agents such as β or γ-secretase inhibitors, mitochondrial stabilisers, microtubule stabilisers or modulators of Tau pathology such as Tau aggregation inhibitors (e.g. methylene blue and REMBER™).

When a compound of formula (I) or a pharmaceutically acceptable salt thereof is used in combination with other therapeutic agents, the compounds may be administered either sequentially or simultaneously by any convenient route.

The invention thus provides, in a further aspect, a combination comprising a compound of formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

Pharmaceutical compositions can be administered to patients by any convenient route. For example, pharmaceutical compositions include those adapted for (1) oral administration such as tablets, capsules, caplets, pills lozenges, powders, syrups, elixirs, suspensions, solutions, emulsions, sachets and cachets; (2) parenteral administration such as sterile solutions, suspensions, implants and powders for reconstitution; (3) transdermal administration such as transdermal patches; (4) inhalation and intranasal such as dry powders, aerosols, suspensions and solutions (sprays and drops); (5) buccal and sublingual administration such as lozenges, patches, sprays, drops, chewing gums and tablets. Orally administrable pharmaceutical compositions are generally preferred.

The compounds of formula (I) or pharmaceutically acceptable salt thereof may be milled using known milling procedures such as wet milling to obtain a particle size appropriate for tablet formation and for other formulation types. Finely divided (nanoparticulate) preparations of the compounds of the invention may be prepared by processes known in the art, for example WO 02/00196.

Tablets and capsules for oral administration may be in unit dose form, and may contain conventional excipients, such as diluents, binding agents, lubricants, disintegrants, glidants, granulating agents, coating agents and wetting agents. The skilled artisan will appreciate that certain pharmaceutically acceptable excipients may serve more than one function and may serve alternative functions depending on how much of the excipient is present in the formulation and what other ingredients are present in the formulation. The tablets may be coated according to methods well known in normal pharmaceutical practice.

The composition may contain from 0.1% to 99% by weight, in some embodiments, 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable compositions will contain 0.1 to 1000 mg, in some embodiments, 0.1 to 200 mg and in some embodiments, 1.0 to 200 mg of the compound of formula (I) or a pharmaceutically acceptable salt thereof and 0.1 to 2 g of one or more pharmaceutically acceptable carriers. Such pharmaceutical compositions may be administered more than once a day, for example two or three a day. Such therapy may extend for a number of weeks, months or years.

The present invention also provides a process for the preparation of a compound of formula (I) or a salt thereof. Compounds of formula (I) or salts thereof may be prepared by a process comprising:

a) reacting a compound of formula (II) or a salt thereof:

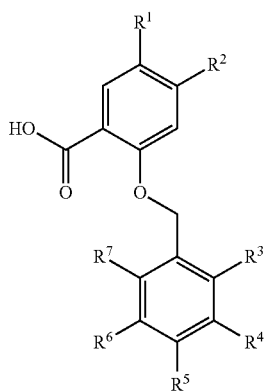

wherein $R^1$, $R^2$, $R^3$, $R^4$, $R^5$, $R^6$ and $R^7$ are as defined above, with a A-$NH_2$ or a salt thereof; or b) reacting a compound of formula (VI) or a salt thereof:

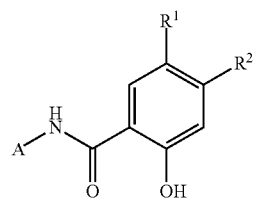

wherein A, $R^1$ and $R^2$ are as defined above, with a compound of formula (IV) or a salt thereof:

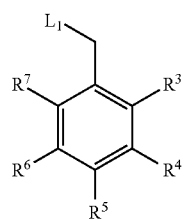

wherein $R^3$, $R^4$, $R^5$, $R^6$ and $R^7$ are as defined above and wherein $L_1$ is a suitable leaving group, such as a halo group (e.g. bromo) or a hydroxyl group; or c) interconversion of one compound of formula (I) or a salt thereof to another compound of formula (I), or a salt thereof.

Process (a) typically utilises activating agents such as 1-(3-dimethylaminopropyl)-3-ethylcarbodiimide hydrochloride (EDC) together with 1-hydroxybenzotriazole (HOBT), or HATU, or CDI (N,N'-carbonyldiimidazole) in a suitable solvent at a suitable temperature. Where EDC/HOBT are used, the reaction may optionally take place in the presence of a base (e.g. triethylamine, diisopropylethylamine or N-ethyl morpholine). Suitable solvents for this reaction include dichloromethane (DCM) or dimethylformamide (DMF) and a suitable temperature would be e.g. between 15° and 40° C. Where CDI is used, a suitable solvent would be THF (tetrahydrofuran). The reaction is a two step process where the reaction of CDI with the acid is carried out at a suitable temperature such as room temperature, followed by addition of the amine with stirring at a suitable temperature e.g. reflux. Where HATU is used, the reaction may optionally take place in the presence of a base (e.g. diisopropylethylamine). Suitable solvents for this reaction include dimethylformamide (DMF) and a suitable temperature would be e.g. room temperature.

Alternatively, process (a) may comprise a step of converting the compound of formula (II) into the corresponding acyl chloride, followed by reaction with A-$NH_2$ or a salt thereof. The step of converting the compound of formula (II) to an acyl chloride typically comprises treatment of the compound of formula (II) with oxalyl chloride in a suitable solvent (e.g. DCM in the presence of a catalytic amount of DMF) at a suitable temperature (e.g. room temperature). The step of reacting the acyl chloride with A-$NH_2$ or a salt thereof optionally takes place in the presence of a base (e.g. diisopropylethylamine or triethylamine) in a suitable solvent such as DCM, at a suitable temperature e.g. between room temperature and 40° C.

When $L_1$ is a hydroxyl group, process (b) is a two step process. The first step is the formation of a basic salt by treatment of the compound of formula (VI) with a base (e.g. potassium hydroxide) in a suitable solvent (such as methanol), at a suitable temperature (such as room temperature). The second step involves the addition of the compound of formula (IV) and takes place in a suitable solvent (such as DMF) at a suitable temperature, such as 50° C. Alternatively, when $L_1$ is a hydroxy group, process (b) may takes place in the presence of coupling agents such as DEAD (diethyl azodicarboxylate) or DIAD (diisopropyl azodicarboxylate), and $Ph_3P$ (triphenyl phosphine). The reaction takes place in a suitable solvent such as toluene or DCM at a suitable temperature such as from 0° C. to room temperature.

When $L_1$ is halo (e.g. bromo), process (b) typically takes place in the presence of a base such as potassium carbonate or caesium carbonate, in a suitable solvent (e.g. DMF or acetone) at a suitable temperature (e.g. between room temperature and reflux).

Process (c) utilises standard chemical transformations known to a person of ordinary skill in the art.

Compounds of formula (I) where either $R^1$ or $R^2$ represent a nitrogen containing heteroaryl ring, which nitrogen containing heteroaryl ring is optionally substituted by one two or three groups selected from halo, methyl or trifluoromethyl and wherein $R^3$ to $R^7$ and $R^{11}$ are not bromo or iodo may be prepared by reaction of the corresponding compound of formula (I) wherein $R^1$ or $R^2$ represents bromo or iodo with the corresponding boronic acid or dioxoborolane compound.

Where the boronic acid is used, the reaction takes place in the presence of a suitable coupling agent such as tetrakis(triphenylphosphine)palladium(0) or bis(triphenylphosphine)palladium(II) chloride optionally in the presence of a base, such as sodium carbonate. The reaction takes place in a suitable solvent (such as DME or 1,4-dioxane) and at a suitable temperature such as 100-140° C.

Where the corresponding dioxoborolane is used, the reaction takes place in the presence of a suitable coupling agent such as tetrakis(triphenylphosphine)palladium(0), optionally in the presence of a base, such as sodium carbonate or tripotassium phosphate. The reaction takes place in a suitable solvent (such as DME or 1,4-dioxane) at a suitable temperature such as 80-140° C.

Compounds of formula (I) where either $R^1$ or $R^2$ represent —(CO)$R^8$ wherein $R^8$ represents —$NR^9R^{10}$ may be prepared from the corresponding compound of formula (I) where either $R^1$ or $R^2$ represent —(CO)$R^8$ wherein $R^8$ represents hydrogen (i.e. formyl) in a two step reaction. The first step comprises oxidation of the formyl group by treatment with sodium chorite. This reaction typically takes place in the presence of an acid (e.g. sulfamic acid) and 2-methyl-1-butene. The second step comprises reaction with the corresponding amine and may be carried out as described above in relation to process (a).

Compounds of formula (II) or salts thereof and compounds of formula (VI) or salts thereof where $R^1$ and $R^2$ independently represent:
halo; or
—$(CH_2)_nR^8$, wherein $R^8$ represents hydrogen;
may be prepared in accordance with the following process:

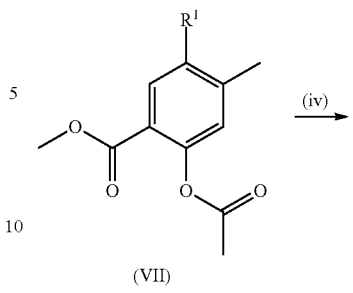

(VII)

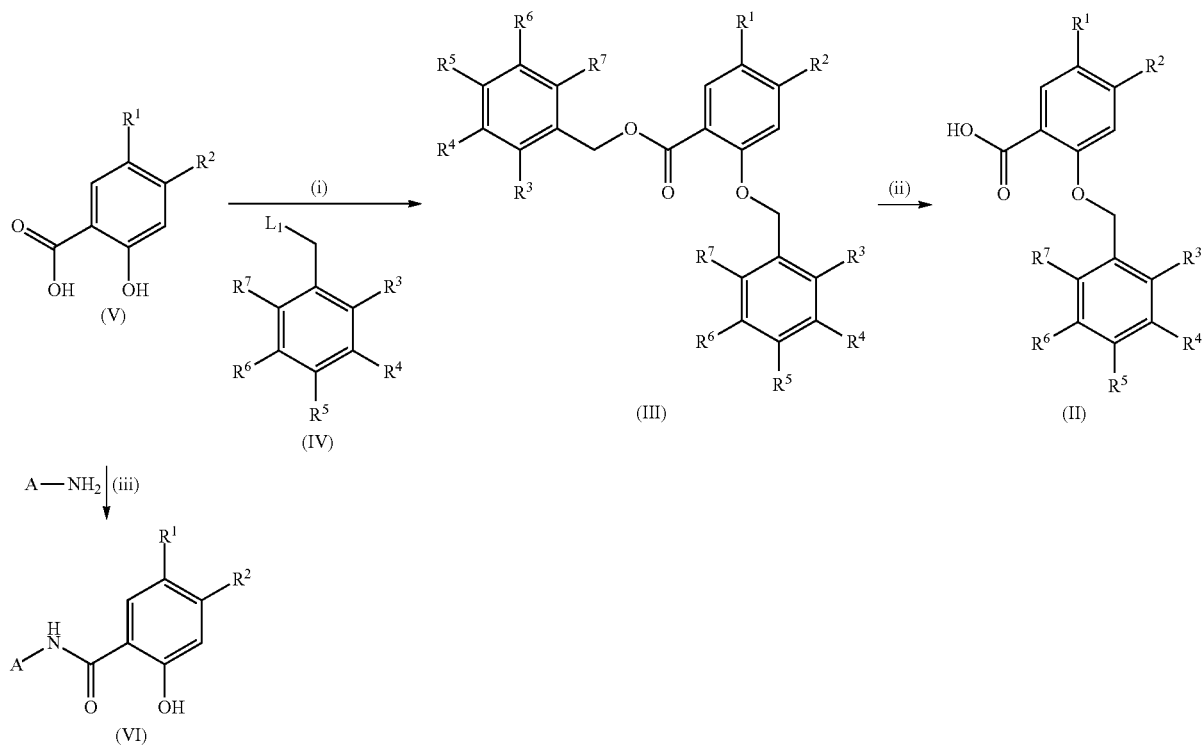

wherein $L_1$, A, $R^3$, $R^4$, $R^5$, $R^6$ and $R^7$ are as defined above and wherein $R^1$ and $R^2$ represent halo or —$(CH_2)_nR^8$, wherein $R^8$ represents hydrogen.

Step (i) may be carried out as described above for process (b).

Step (ii) typically comprises treatment of a compound of formula (III) with lithium hydroxide in a suitable solvent, such as a mixture of THF (tetrahydrofuran) and water or a mixture of THF, methanol and water, at a suitable temperature such as between room temperature and reflux. Alternatively, step (ii) may comprise refluxing in a mixture of ethanol and 2M NaOH.

Step (iii) may be carried out as described above for process (a).

Compounds of formula (V) or salts thereof wherein where $R^2$ represents —$(CO)R^8$ wherein $R^8$ represents hydrogen (i.e. formyl) may be prepared in accordance with the following process:

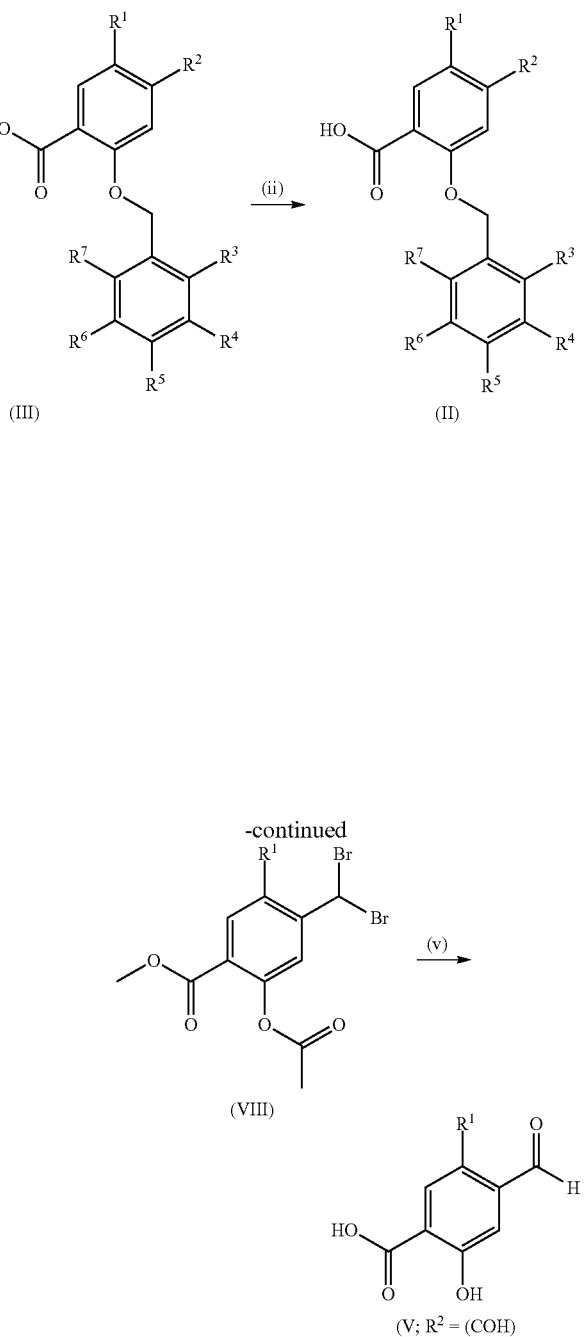

wherein $R^1$ is as defined above.

Step (iv) comprises dibromination using NBS (N-bromosuccinimide) in carbon tetrachloride at 85° C. in the presence of a radical initiator (benzoyl peroxide or AlBN).

Step (v) is an oxidation reaction and typically comprises treatment with calcium carbonate. This step takes place in the presence of a suitable solvent such as a mixture of 1,4-dioxane and water, at a suitable temperature such as 150° C. This is followed by hydrolysis as described above in relation to step (ii).

The skilled person will appreciate that compounds of formula (V) or salts thereof wherein where $R^1$ represents —(CO)$R^8$ wherein $R^8$ represents hydrogen (i.e. formyl) may be prepared in an analogous manner.

Compounds of formula (III) or (VI) where either $R^1$ or $R^2$ represent —(CO)$R^8$ wherein $R^8$ represents —$NR^9R^{10}$ may be prepared from the corresponding compound of formula (III) or (VI) where either $R^1$ or $R^2$ represent —(CO)$R^8$ wherein $R^8$ represents hydrogen (i.e. formyl) in a two step reaction. The first step comprises oxidation of the formyl group by treatment with sodium chorite. This reaction typically takes place in the presence of an acid (e.g. sulfamic acid) and 2-methyl-1-butene. The second step comprises reaction with the corresponding amine and may be carried out as described above in relation to process (a).

Compounds of formula (V) where $R^2$ represents —(CH$_2$)$_n$R$^8$, wherein $R^8$ represents —$NR^9R^{10}$ may be prepared in accordance with the following process:

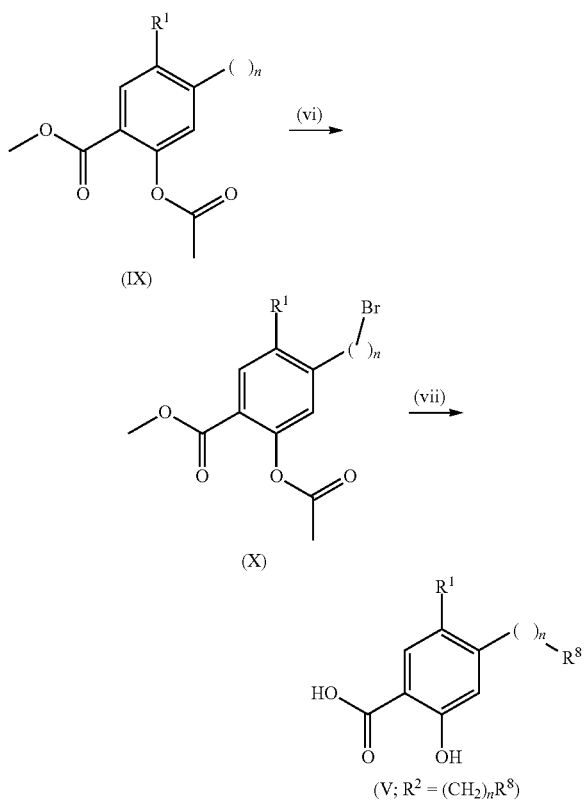

wherein $R^1$ is as defined above and $R^8$ represents —$NR^9R^{10}$.

Step (vi) may be carried out as described above in relation to step (iv).

Step (vii) comprises displacement of the bromide with the corresponding amine in the presence of a base (e.g. triethylamine) in a suitable solvent such as dichloromethane followed by hydrolysis as described above in relation to step (ii).

The skilled person will appreciate that compounds of formula (V) or salts thereof wherein where $R^1$ represents —(CH$_2$)$_n$R$^8$, wherein $R^8$ represents —$NR^9R^{10}$ may be prepared in an analogous manner.

Compounds of formula (V) where $R^2$ represents $C_{1-3}$ haloalkyl may be prepared in accordance with the following process:

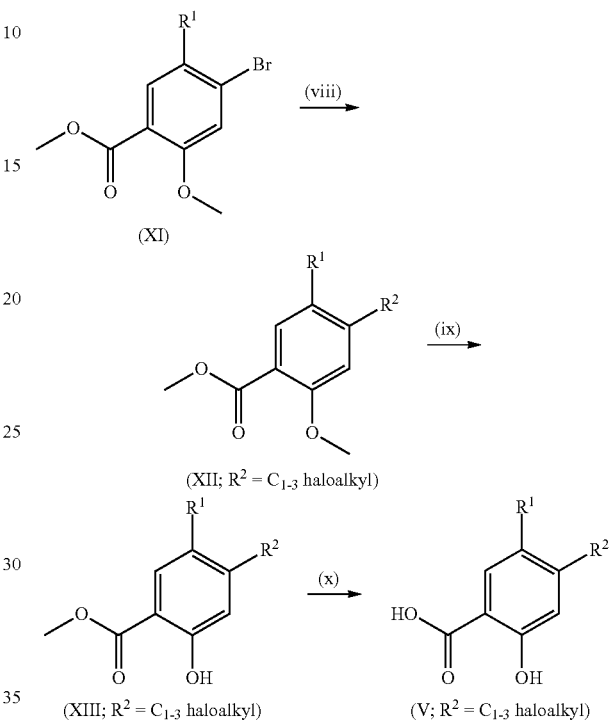

wherein $R^1$ is as defined above and $R^2$ represents $C_{1-3}$ haloalkyl.

Step (viii) comprises reaction with a salt of formula K(CO$_2$R$^2$) in the presence of a copper (I) catalyst such as copper (I) iodide. The reaction takes place in a suitable solvent at a suitable temperature such as 170° C.

Step (ix) is a two step reaction. The first step comprises reaction with BBr$_3$ in a suitable solvent such as DCM, at a suitable temperature such as 0° C. The second step comprises hydrolysis by treatment with concentrated HCl.

Step (x) is another hydrolysis reaction and may be carried out as described above for step (ii).

The skilled reader will appreciate that, where $R^1$ and $R^2$ are different, it will be necessary to use a starting material in which the corresponding positions are differently substituted to allow different reactions at the two positions. It may be necessary to order the reactions to avoid unwanted side reactions and it may be necessary to protect certain groups during other reactions.

Compounds of formula (V) wherein where $R^1$ and $R^2$ independently represent halo or —(CH$_2$)$_n$R$^8$ wherein $R^8$ represents hydrogen, compounds of formula (IV), (VII) (IX) and (XI) and compounds of formula A-NH$_2$ and K(CO$_2$R$^2$) are either commercially available or may be readily prepared from commercially available compounds using procedures known to a person of ordinary skill in the art.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Abbreviations
DCM Dichloromethane
DMSO Dimethyl sulfoxide
DIPEA Diisopropylethylamine
EDC 1-(3-Dimethylaminopropyl)-3-ethylcarbodiimide hydrochloride
HATU 2-(1H-7-Azabenzotriazol-1-yl)-1,1,3,3-tetramethyl uranium hexafluorophosphate
HOAt 1-Hydroxy-7-azabenzotriazole
HOBT 1-Hydroxybenzotriazole
MDAP Mass Directed Auto Purification
NBS N-Bromosuccinimide
NCS N-Chlorosuccinimide
Pd($Ph_3P)_4$/palladium tetrakis Tetrakis(triphenylphosphine)palladium(0)
SP4 Biotage four-column sequential FLASH purification system Description 1

Methyl 2-hydroxy-4-methylbenzoate (D1)

Thionyl chloride (2.16 ml, 29.6 mmol) was added dropwise to a solution of 2-hydroxy-4-methylbenzoic acid (3 g, 19.72 mmol) in methanol (20 ml). The solution was heated at 50° C. for 24 hours. The solution was cooled, the solvent was removed in vacuo and the residue was dissolved in dichloromethane (20 ml), washed with water (15 ml) and saturated $NaHCO_3$ solution (2×10 ml), dried and the solvent removed in vacuo to yield the title compound as an oil. 3.28 g.

$^1$H NMR (DMSO-$d_6$): 2.30 (3H, s), 3.80 (3H, s), 6.61-6.88 (2H, m), 7.68 (1H, d, J=7.89 Hz), 10.48 (1H, s)

Description 2

Methyl 5-bromo-2-hydroxy-4-methylbenzoate (D2)

Bromine (0.47 ml, 9.03 mmol) was added dropwise to a solution of methyl 2-hydroxy-4-methylbenzoate (may be prepared as described in Description 1; 1.5 g, 9.03 mmol) in chloroform (20 ml) at 0° C. The solution was stirred for 1 hour at 0° C. The reaction was quenched with saturated sodium sulphite (10 ml), then extracted with dichloromethane (2×10 ml). The combined organic layers were washed with brine (10 ml), dried ($MgSO_4$) and the solvent removed in vacuo to yield the title compound as a white solid. 2.24 g.

$^1$H NMR (DMSO-$d_6$): 2.33 (3H, s), 3.95 (3H, s), 7.03 (1H, s), 7.87 (1H, s), 10.40 (1H, br. s.)

Description 3

Methyl 2-(acetyloxy)-5-bromo-4-methylbenzoate (D3)

Acetic anhydride (3.06 mL, 32.5 mmol) was added to a solution of methyl 5-bromo-2-hydroxy-4-methylbenzoate (3.98 g, 16.24 mmol), which may be prepared according to procedure described in Description 2, in Pyridine (10 mL) was added. The reaction mixture was stirred for four hours. The solvent was removed in vacuo and the residue was purified by SP4 (10-20% EtOAc/hexane) to yield the desired compound as oil (4.54 g, 97% yield).

MS (electrospray): m/z [M+H]+287/289

$^1$H NMR (DMSO-d6): 2.28 (3H, s), 2.40 (3H, s), 3.82-3.85 (3H, m), 7.30 (1H, s), 8.06 (1H, s)

Description 4

Methyl 2-(acetyloxy)-5-bromo-4-(bromomethyl)benzoate (D4)

NBS (0.71 g, 4.01 mmol) and benzoyl peroxide (0.07 g, 0.20 mmol) were added to a solution of methyl 2-(acetyloxy)-5-bromo-4-methylbenzoate (may be prepared as described in Description 3; 1.15 g, 4.01 mmol) in carbon tetrachloride (20 ml). The mixture was heated at reflux for 18 hours, cooled and the solvent removed in vacuo. Purification by SP4 (10-20% ethyl acetate/hexane) yielded the title compound as a pale yellow oil. 1.38 g.

MS (electrospray): m/z [M+H]$^+$366/368

$^1$H NMR (DMSO-$d_6$): 2.31 (3H, s), 3.83 (3H, s), 4.74 (2H, s), 7.59 (1H, s), 8.08-8.16 (1H, m)

Description 5

5-Bromo-2-hydroxy-4-(4-morpholinylmethyl)benzoic acid (D5)

Triethylamine (0.37 ml, 2.63 mmol) and morpholine (0.15 ml, 1.71 mmol) were added to a solution of methyl 2-(acetyloxy)-5-bromo-4-(bromomethyl)benzoate (may be prepared as described in Description 4; 481 mg, 1.31 mmol) in acetone (10 ml). The mixture was stirred for 30 minutes then the solvent was removed in vacuo. The residue was redissolved in dichloromethane (10 ml), washed with water (10 ml), dried ($MgSO_4$) and the solvent removed in vacuo to give the morpholine intermediate.

The intermediate was redissolved in tetrahydrofuran (4 ml) and lithium hydroxide (126 mg, 5.26 mmol) was added followed by water (1 ml). The mixture was heated at 50° C. for 90 minutes. The mixture was cooled and the solvent removed in vacuo to yield the title compound as a brown oil which was used in the next step without further purification. 415 mg.

MS (electrospray): m/z [M+H]$^+$316/318

Description 6

Phenylmethyl 5-bromo-4-(4-morpholinylmethyl)-2-[(phenylmethyl)oxy]benzoate (D6)

To a solution of 5-bromo-2-hydroxy-4-(4-morpholinylmethyl)benzoic acid (may be prepared as described in Description 5; 415 mg, 1.31 mmol) in N,N-dimethylformamide (10 ml) was added potassium carbonate (635 mg, 4.59 mmol) and benzyl bromide (0.34 ml, 2.89 mmol). The reaction was stirred at room temperature overnight. Ethyl acetate (20 ml) and water (20 ml) were added and the organic layer was separated, washed with water (3×10 ml), dried ($MgSO_4$), and the solvent removed in vacuo to give a residue. Purification by column chromatography (10% ethyl acetate/hexane) yielded the title compound as oil. 379 mg.

MS (electrospray): m/z [M+H]⁺496/498

¹H NMR (DMSO-d$_6$): 1.99 (2H, s), 2.07 (6H, s), 2.38 (2H, s), 5.07 (4H, s), 7.27-7.40 (11H, m)

Description 7

5-Bromo-4-(4-morpholinylmethyl)-2-[(phenylmethyl)oxy]benzoic acid (D7)

To a solution of phenylmethyl 5-bromo-4-(4-morpholinylmethyl)-2-[(phenylmethyl)oxy]benzoate (may be prepared as described in Description 6; 379 mg, 0.76 mmol) in tetrahydrofuran (6 ml) was added lithium hydroxide (110 mg, 4.58 mmol) followed by water (1.5 ml). The reaction was stirred over the weekend, the solvent removed in vacuo and purified by MDAP to yield the title compound as a solid. 249 mg.

MS (electrospray): m/z [M+H]⁺406/408

LCMS: N15123-52-A1 (LHD12187-1) m/z 406/408 M+H.

¹H NMR (DMSO-d$_6$): 2.25-2.35 (4H, m), 3.39 (2H, s), 3.45-3.55 (4H, m), 5.09 (2H, s), 6.90 (1H, s), 7.27 (2H, dd, J=4.60, 2.19 Hz), 7.33 (2H, t, J=7.34 Hz), 7.46 (2H, d, J=7.23 Hz)

Description 8

Methyl 5-bromo-4-methyl-2-[(phenylmethyl)oxy]benzoate (D8)

Potassium carbonate (0.85 g, 6.12 mmol) and benzyl bromide (0.53 ml, 4.49 mmol) were added to a solution of methyl 5-bromo-2-hydroxy-4-methylbenzoate (1 g, 4.08 mmol) in N,N-dimethylformamide (10 ml). The mixture was stirred at room temperature for 72 hours. Ethyl acetate (20 ml) and water (20 ml) were added and the organic layer separated, washed with water (3×10 ml), dried (MgSO$_4$) and the solvent removed in vacuo. Purification by column chromatography (10% ethyl acetate/hexanes) yielded the title compound as an oil. 1.35 g.

MS (electrospray): m/z [M+H]⁺335/337

¹H NMR (DMSO-d$_6$): 2.38 (3H, s), 3.77 (3H, s), 5.21 (2H, s), 7.29-7.36 (2H, m), 7.41 (2H, t, J=7.56 Hz), 7.45-7.53 (2H, m), 7.85 (1H, s)

Description 9

5-Bromo-4-methyl-2-[(phenylmethyl)oxy]benzoic acid (D9)

Lithium hydroxide (0.29 g, 12.08 mmol) and water (4 ml) were added to a solution of methyl 5-bromo-4-methyl-2-[(phenylmethyl)oxy]benzoate (may be prepared as described in Description 8; 1.35 g, 4.03 mmol) in tetrahydrofuran (20 ml). The reaction was heated at 40° C. for 18 hours. The solvent was removed in vacuo and the residue was partitioned between water (20 ml) and ethyl acetate (30 ml). The aqueous layer was acidified to pH2 using 2N HCl. The organic layer was separated, dried (MgSO$_4$) and the solvent removed in vacuo to yield the title compound as a white solid. 1.26 g.

MS (electrospray): m/z [M+H]⁺321/323

¹H NMR (DMSO-d$_6$): 2.37 (3H, s), 5.20 (2H, s), 7.24-7.44 (4H, m), 7.49 (2H, d, J=7.45 Hz), 7.81 (1H, s)

Description 10

1-(4-Bromo-2-hydroxy-5-methylphenyl)ethanone (D10)

To 3-bromo-4-methylphenol (2 g, 10.69 mmol) was added acetyl chloride (0.80 ml, 11.23 mmol). The mixture was heated at 60° C. for one hour, cooled and aluminium chloride (1.426 g, 10.69 mmol) was added. The mixture was heated at 180° C. for 40 minutes, cooled and quenched by stirring with 5N HCl (20 ml) for 20 minutes. The solid was filtered to yield the title compound as a brown solid. 2.45 g.

¹H NMR (DMSO-d$_6$): 2.31 (3H, s), 2.61 (3H, s), 7.24 (1H, s), 7.83 (1H, s), 11.72 (1H, s)

Description 11

1-{4-Bromo-5-methyl-2-[(phenylmethyl)oxy]phenyl}ethanone (D11)

Potassium carbonate (1.45 g, 10.48 mmol) and benzyl bromide (0.65 ml, 5.50 mmol) were added to a solution of 1-(4-bromo-2-hydroxy-5-methylphenyl)ethanone (may be prepared as described in Description 10; 1.2 g, 5.24 mmol) in N,N-dimethylformamide (10 ml). The mixture was stirred at room temperature overnight. Water (20 ml) and ethyl acetate (30 ml) were added and the organic layer was separated, washed with water (2×20 ml), dried (MgSO$_4$) and the solvent removed in vacuo. Purification by column chromatography (5-10% ethyl acetate/hexane) yielded the title compound. 607 mg.

MS (electrospray): m/z [M+H]⁺319/321

¹H NMR (DMSO-d$_6$): 2.30 (3H, s), 3.32 (3H, s), 5.25 (2H, s), 7.32-7.46 (3H, m), 7.47-7.53 (3H, m), 7.56 (1H, s)

Description 12

4-Bromo-5-methyl-2-[(phenylmethyl)oxy]benzoic acid (D12)

To a solution of 1-{4-bromo-5-methyl-2-[(phenylmethyl)oxy]phenyl}ethanone (may be prepared as described in Description 11; 607 mg, 1.90 mmol) in 1,4-dioxane (10 ml) was added sodium hydroxide (761 mg, 19.02 mmol) in water (10 ml). The solution was cooled to 0° C. and bromine (0.29 ml, 5.71 mmol) was added. The mixture was stirred for 10 minutes at 0° C. and then at room temperature for one hour. The dioxane was removed under reduced pressure and the residue acidified to pH=2 using 2N HCl. The mixture was extracted with ethyl acetate (3×20 ml), dried (MgSO$_4$) and the solvent removed in vacuo to yield the title compound. 611 mg.

MS (electrospray): m/z [M+H]⁺321/323

¹H NMR (DMSO-d$_6$): 2.29 (3H, s), 3.35 (1H, br. s.), 5.20 (2H, s), 7.28-7.46 (4H, m), 7.48 (2H, d, J=7.02 Hz), 7.64 (1H, s)

Description 13

4-Bromo-2-hydroxy-5-methylbenzoic acid (D13)

To a solution of 4-bromo-5-methyl-2-[(phenylmethyl)oxy]benzoic acid (may be prepared as described in Description 12; 3.61 g, 11.24 mmol) in toluene (15 ml)/trifluoroacetic acid (15 ml) was added thioanisole (1.33 ml, 11.24 mmol). The solution was stirred for 18 hours, then the solvent was removed in vacuo. The residue was partitioned between 2N HCl (10 ml) and ethyl acetate (30 ml). The organic layer was separated, dried (MgSO$_4$) and the solvent removed in vacuo to give the product as a brown solid which contained thioanisole. Trituration with 6:1 cyclohexane/ethyl acetate yielded the title compound as a white solid. 2.08 g.

MS (electrospray): m/z, [M+H]$^+$=229/231

Description 14

Methyl 4-bromo-2-hydroxy-5-methylbenzoate (D14)

To a solution of 4-bromo-2-hydroxy-5-methylbenzoic acid (may be prepared as described in Description 13; 1.47 g, 6.36 mmol) in methanol (15 ml) was added thionyl chloride (0.93 ml, 12.72 mmol). The reaction was heated at 50° C. for 72 hours, then DCM (20 ml) and water (10 ml) were added. The organic layer was separated and washed with saturated NaHCO$_3$ solution (10 ml), dried (MgSO$_4$) and the solvent removed in vacuo to yield the title compound as a white solid. 1.2 g.

$^1$H NMR (400 MHz, DMSO-d$_6$); 2.28 (3H, s), 2.67 (0H, br. s.), 3.87 (3H, s), 7.24 (1H, s), 7.71 (1H, s).

Description 15

Methyl 2-(acetyloxy)-4-bromo-5-methylbenzoate (D15)

To a solution of methyl 4-bromo-2-hydroxy-5-methylbenzoate (may be prepared as described in Description 14; 1.2 g, 4.90 mmol) in pyridine (10 ml) was added acetic anhydride (2.08 ml, 22.03 mmol). The solution was stirred for one hour, then the solvent was removed in vacuo and purified by column chromatography (SiO$_2$, 6:1 cyclohexane/ethyl acetate) to yield the title compound as a white solid. 1.28 g.

MS (electrospray): m/z, [M+H]$^+$=288/290

Description 16

Methyl 2-(acetyloxy)-4-bromo-5-(bromomethyl)benzoate (D16)

To a solution of methyl 2-(acetyloxy)-4-bromo-5-methylbenzoate (may be prepared as described in Description 15; 705 mg, 2.46 mmol) in carbon tetrachloride (10 ml) was added NBS (437 mg, 2.46 mmol) and benzoyl peroxide (47.6 mg, 0.15 mmol). The solution was heated at 85° C. overnight, cooled and the solvent was removed in vacuo to give a residue. Purification by column chromatography (SiO$_2$, 6:1 cyclohexane/ethyl acetate) yielded the title compound as an oil. 741 mg.

LCMS did not ionise
$^1$H NMR (400 MHz, DMSO-d$_6$); 1.40 (3H, s), 2.28 (3H, s), 3.83 (3H, s), 4.81 (2H, s), 7.69 (1H, s), 8.20 (1H, s).

Description 17

Methyl 4-bromo-2-hydroxy-5-(4-morpholinylmethyl)benzoate (D17)

To a solution of methyl 2-(acetyloxy)-4-bromo-5-(bromomethyl)benzoate (may be prepared as described in Description 16; 741 mg, 2.03 mmol) in acetone (5 ml) was added triethylamine (0.56 ml, 4.05 mmol) and morpholine (0.23 ml, 2.63 mmol). The mixture was stirred for 1 hour, then the solvent was removed in vacuo to give a residue. The residue was redissolved in ethyl acetate (10 ml) and washed with water (10 ml). The organic layer was dried (MgSO$_4$) and the solvent removed in vacuo to give oil. Purification by column chromatography (SiO$_2$, 3:1-1:1 cyclohexane/ethyl acetate) gave the product as oil. 580 mg.

MS (electrospray): m/z, [M+H]$^+$=330/332

Description 18

Methyl 2-{[(4-fluorophenyl)methyl]oxy}-4-(1-methyl-1H-pyrazol-4-yl)-5-(4-morpholinylmethyl)benzoate (D18)

To a solution of methyl 4-bromo-2-hydroxy-5-(4-morpholinylmethyl)benzoate (may be prepared as described in Description 17; 250 mg, 0.76 mmol) in 1,2-dimethoxyethane (3 ml) was added 1-methyl-4-(4,4,5,5-tetramethyl-1,3,2-dioxaborolan-2-yl)-1H-pyrazole (189 mg, 0.91 mmol), tripotassium phosphate (321 mg, 1.51 mmol), and Pd(Ph$_3$P)$_4$ (52.5 mg, 0.05 mmol). The reaction was heated at 120° C. for one hour, cooled and the solvent removed in vacuo. The residue was redissolved in N,N-dimethylformamide (4 ml) and cesium carbonate (493 mg, 1.15 mmol) and 4-fluorobenzyl bromide (0.11 ml, 0.91 mmol) were added and the mixture heated at 40° C. for 3 hours. Water (10 ml) and ethyl acetate (15 ml) were added and the organic layer was separated and washed further with water (2×10 ml), dried (MgSO$_4$) and the solvent removed in vacuo. Purification by column chromatography (SiO$_2$; (solute, 10% 7M NH$_3$ in methanol/dichloromethane) yielded the title compound as a gum. 333 mg.

MS (electrospray): m/z, [M+H]$^+$=440

Description 19

(4-Fluorophenyl)methyl 5-bromo-2-{[(4-fluorophenyl)methyl]oxy}-4-(4-morpholinylmethyl)benzoate (D19)

To a solution of 5-bromo-2-hydroxy-4-(4-morpholinylmethyl)benzoic acid (may be prepared as described in Description 5; 720 mg, 2.28 mmol) in N,N-dimethylformamide (10 ml) was added potassium carbonate (1102 mg, 7.97 mmol) and 4-fluorobenzyl bromide (0.62 ml, 5.01 mmol). The mixture was heated at 50° C. for 2 hours, cooled and the solvent removed in vacuo. The residue was partitioned between water (10 ml) and ethyl acetate (15 ml). The organic layer was separated, washed further with water (2×5 ml), dried (MgSO$_4$) and the solvent removed in vacuo to give a residue. Purification by column (SiO$_2$, 6:1-1:1 cyclohexane/ethyl acetate) gave the product as a pale yellow oil. 544 mg.

MS (electrospray): m/z, [M+H]$^+$=532/534

Description 20

5-Bromo-2-{[(4-fluorophenyl)methyl]oxy}-4-(4-morpholinylmethyl)benzoic acid (D20)

To a solution of phenylmethyl 5-bromo-4-(4-morpholinylmethyl)-2-[(phenylmethyl)oxy]benzoate (may be prepared as described in Description 6; 544 mg, 1.02 mmol) in tetrahydrofuran (4 ml) was added lithium hydroxide (147 mg, 6.13 mmol) and water (1 ml). The mixture was heated at 50° C. for 4 hours, cooled and neutralised with 2M hydrochloric acid (3.07 ml, 6.13 mmol). The solvent was removed in vacuo to yield the title compound as a white solid. 424 mg. MS (electrospray): m/z, [M+H]$^+$=422/424

Description 21

(2,4-Difluorophenyl)methyl 5-bromo-2-{[(2,4-difluorophenyl)methyl]oxy}-4-(4-morpholinylmethyl)benzoate (D21)

To a solution of 5-bromo-2-hydroxy-4-(4-morpholinylmethyl)benzoic acid (may be prepared as described in Description 5; 720 mg, 2.277 mmol) in N,N-dimethylformamide (10 ml) was added potassium carbonate (1102 mg, 7.97 mmol) and 4-fluorobenzyl bromide (619 µl, 5.01 mmol). The mixture was heated at 50° C. for 2 hours, cooled and the solvent removed in vacuo. The residue was partitioned between water (10 ml) and ethyl acetate (15 ml). The organic layer was separated, washed further with water (2×5 ml) and then dried (MgSO$_4$) and the solvent removed in vacuo. Purification by column chromatography (SiO$_2$, 6:1-1:1 cyclohexane/ethyl acetate) yielded the title compound as a pale yellow oil. 833 mg. MS (electrospray): m/z, [M+H]$^+$=568/570

Description 22

5-Bromo-2-{[(2,4-difluorophenyl)methyl]oxy}-4-(4-morpholinylmethyl)benzoic acid (D22)

To a solution of (2,4-difluorophenyl)methyl 5-bromo-2-{[(2,4-difluorophenyl)methyl]oxy}-4-(4-morpholinylmethyl)benzoate (may be prepared as described in Description 21; 833 mg, 1.466 mmol) in tetrahydrofuran (4 ml) was added lithium hydroxide (211 mg, 8.79 mmol) and water (1 ml). The mixture was heated at 50° C. for 4 hours, cooled and neutralised with 2M hydrochloric acid (3.66 ml, 7.33 mmol). The solvent was removed in vacuo to yield the title compound as a white solid. 648 mg.
MS (electrospray): m/z, [M+H]$^+$=442/444

Description 23

Methyl 2-(acetyloxy)-5-bromo-4-(dibromomethyl)benzoate (D23)

To a solution of methyl 2-(acetyloxy)-5-bromo-4-methylbenzoate (may be prepared as described in Description 3; 2.13 g, 7.42 mmol) in carbon tetrachloride (20 ml) was added NBS (2.64 g, 14.84 mmol) and benzoyl peroxide (0.18 g, 0.74 mmol). The mixture was heated at 85° C. for overnight, cooled and the solvent removed in vacuo. Purification by column chromatography (SiO$_2$; 6:1 cyclohexane/ethyl acetate) yielded the title compound as a white solid. 3.05 g.
$^1$H NMR (400 MHz, DMSO-d$_6$); 2.31 (3H, s) 3.83 (3H, s) 7.31 (1H, s) 7.82 (1H, s) 8.12 (1H, s)

Description 24

Phenylmethyl 5-bromo-4-formyl-2-[(phenylmethyl)oxy]benzoate (D20)

To a solution of methyl 2-(acetyloxy)-5-bromo-4-(dibromomethyl)benzoate (may be prepared as described in Description 23; 1 g, 2.25 mmol) in 1,4-dioxane (5 ml) was added calcium carbonate (0.68 g, 6.74 mmol) and water (5 ml). The mixture was heated at 150° C. for 3 hours, cooled and the solvent was removed in vacuo. The residue was suspended in N,N-dimethylformamide (5 ml) and potassium carbonate (0.78 g, 5.62 mmol) and benzyl bromide (0.59 ml, 4.94 mmol) were added and the mixture was stirred for 18 hours. Ethyl acetate (15 ml) and water (10 ml) were added and the organic layer washed further with water (2×10 ml), dried (MgSO$_4$) and the solvent removed in vacuo. Some starting material was still present. The residue was redissolved in N,N-dimethylformamide (5 ml) and potassium carbonate (0.78 g, 5.62 mmol) and benzyl bromide (0.59 ml, 4.94 mmol) were added and heated at 50° C. for 3 hours, cooled and the solvent was removed in vacuo. Purification by column chromatography (SiO$_2$; 6:1 cyclohexane/ethyl acetate) yielded the title compound as an oil. 956 mg.
MS (electrospray): m/z, [M+H]$^+$=426

Description 25

Phenylmethyl 5-bromo-4-(4-morpholinylcarbonyl)-2-[(phenylmethyl)oxy]benzoate (D25)

To a solution of phenylmethyl 5-bromo-4-formyl-2-[(phenylmethyl)oxy]benzoate (may be prepared as described in Description 24; 920 mg, 2.00 mmol) in tetrahydrofuran (8 ml), water (5 ml) and dimethyl sulfoxide (0.8 ml) was added sulfamic acid (742 mg, 7.64 mmol) and 2-methyl-1-butene (0.48 ml, 4.50 mmol). The solution was cooled to 0° C. and sodium chlorite (610 mg, 6.74 mmol) in water (3 ml) was added dropwise. After 45 minutes at 0° C. the mixture was quenched with saturated Na$_2$S$_2$O$_3$ solution (20 ml) and extracted with ethyl acetate (3×10 ml). The organic layer was dried (MgSO$_4$) and the solvent removed in vacuo to give the intermediate as an oil. The oil was redissolved in N,N-dimethylformamide (5 ml) and diisopropylethylamine (0.79 ml, 4.50 mmol), morpholine (0.29 ml, 3.37 mmol), 1-hydroxy-7-azabenzotriazole (367 mg, 2.70 mmol) and EDC (733 mg, 3.82 mmol) were added. The mixture was stirred for 4 hours then water (10 ml) and ethyl acetate (20 ml) were added. The organic layer was separated and further washed with water (2×10 ml), dried (MgSO$_4$) and the solvent removed in vacuo to give a gum. Purification by column chromatography (SiO$_2$; 1:1 ethyl acetate/cyclohexane) yielded the title compound as a yellow gum. 730 mg.
MS (electrospray): m/z, [M+H]$^+$=510/512

Description 26

5-(1-Methyl-1H-pyrazol-4-yl)-4-(4-morpholinylcarbonyl)-2-[(phenylmethyl)oxy]benzoic acid (D26)

To a solution of phenylmethyl 5-bromo-4-(4-morpholinylcarbonyl)-2-[(phenylmethyl)oxy]benzoate (may be prepared as described in Description 25; 730 mg, 1.430 mmol) in 1,2-dimethoxyethane (6 ml) was added 1-methyl-4-(4,4,5,5-tetramethyl-1,3,2-dioxaborolan-2-yl)-1H-pyrazole (357 mg, 1.72 mmol), tripotassium phosphate (607 mg, 2.86 mmol) and Pd(Ph$_3$P)$_4$ (99 mg, 0.09 mmol) followed by water (0.5 ml). The mixture was heated in a microwave at 130° C. for 90 minutes, cooled and the solvent removed in vacuo. Purification by column chromatography (SiO$_2$; 1:1 ethyl acetate/cyclohexane to 10% 7M NH$_3$ in methanol/dichloromethane) gave the intermediate. To a solution of this intermediate in tetrahydrofuran (4 ml) was added lithium hydroxide (103 mg, 4.29 mmol) and water (0.5 ml). The solution was stirred for 18 hours before neutralising with 2M hydrochloric acid (2.15 ml, 4.29 mmol). The solvent removed in vacuo to give the product as a solid. 603 mg.

MS (electrospray): m/z, [M+H]$^+$=422

Description 27

(4-Fluorophenyl)methyl 5-bromo-2-{[(4-fluorophenyl)methyl]oxy}-4-formylbenzoate (D27)

To a suspension of methyl 2-(acetyloxy)-5-bromo-4-(dibromomethyl)benzoate (may be prepared as described in Description 23; 1 g, 2.25 mmol) in 1,4-dioxane (5 ml)/water (5 ml) was added calcium carbonate (0.68 g, 6.74 mmol). The mixture was heated in a microwave for 3.5 hours, cooled and the solvent removed in vacuo. The intermediate was suspended in N,N-dimethylformamide (10 ml) and potassium carbonate (0.78 g, 5.62 mmol) and 4-fluorobenzyl bromide (0.61 ml, 4.94 mmol) were added and the mixture stirred for overnight. The solvent was removed in vacuo and the residue taken up in ethyl acetate/H$_2$O (10 ml/10 ml). The organic layer was dried and the solvent removed in vacuo. The residue was redissolved in N,N-dimethylformamide (3 ml) and potassium carbonate (0.78 g, 5.62 mmol) and 4-fluorobenzyl bromide (0.61 ml, 4.94 mmol) added and stirred for 2 hours. Ethyl acetate (20 ml) and water (10 ml) were added, The organic layer was washed further with water (2×10 ml), dried (MgSO$_4$) and the solvent removed in vacuo. Purification by column chromatography (SiO$_2$, 6:1 cyclohexane/ethyl acetate) yielded the title compound as an oil. 920 mg.

MS (electrospray): m/z, [M+H]$^+$=462

Description 28

(4-Fluorophenyl)methyl 5-bromo-2-{[(4-fluorophenyl)methyl]oxy}-4-(4-morpholinylcarbonyl)benzoate (D28)

(D28)

To a solution of (4-fluorophenyl)methyl 5-bromo-2-{[(4-fluorophenyl)methyl]oxy}-4-formylbenzoate (may be prepared as described in Description 27; 920 mg, 2.00 mmol) in tetrahydrofuran (8 ml), water (5 ml) and dimethyl sulfoxide (0.8 ml) was added sulfamic acid (658 mg, 6.78 mmol) and 2-methyl-1-butene (0.430 ml, 3.99 mmol). The solution was cooled to 0° C. and sodium chlorite (541 mg, 5.98 mmol) in water (3 ml) was added. After 60 minutes at 0° C. the reaction was quenched with saturated Na$_2$S$_2$O$_3$ solution (20 ml) and then extracted with ethyl acetate (3×10 ml). The organic layer was dried (MgSO$_4$) and the solvent removed in vacuo to give the intermediate as oil. The oil was redissolved in N,N-dimethylformamide (5 ml), diisopropylethylamine (0.70 ml, 3.99 mmol), morpholine (0.226 ml, 2.59 mmol), 1-hydroxy-7-azabenzotriazole (326 mg, 2.39 mmol) and EDC (650 mg, 3.39 mmol) were added, and the reaction was stirred for 72 hours. Water (10 ml) and ethyl acetate (20 ml) were added. The organic layer was separated and washed with water (2×10 ml), dried (MgSO$_4$) and the solvent removed in vacuo to give a gum. Purification by column chromatography (SiO$_2$; 1:1 ethyl acetate/cyclohexane) yielded the title compound as a yellow gum. 642 mg.

MS (electrospray): m/z, [M+H]$^+$=547

Description 29

2-{[(4-Fluorophenyl)methyl]oxy}-5-(1-methyl-1H-pyrazol-4-yl)-4-(4-morpholinylcarbonyl)benzoic acid (D29)

To a solution of (4-fluorophenyl) methyl 5-bromo-2-{[(4-fluorophenyl) methyl]oxy}-4-(4-morpholinylcarbonyl)benzoate (may be prepared as described in Description 28; 350 mg, 0.64 mmol) in 1,2-dimethoxyethane (6 ml) was added 1-methyl-4-(4,4,5,5-tetramethyl-1,3,2-dioxaborolan-2-yl)-1H-pyrazole (160 mg, 0.77 mmol), tripotassium phosphate (272 mg, 1.28 mmol) and Pd(Ph$_3$P)$_4$ (44.4 mg, 0.04 mmol) followed by water (0.5 ml). The mixture was heated in a microwave at 130° C. for 2 hours, cooled and the solvent removed in vacuo. Purification by column chromatography (SiO$_2$; 1:1 ethyl acetate/cyclohexane to 10% 7M NH$_3$ in methanol/dichloromethane) gave a yellow gum. The gum was redissolved in tetrahydrofuran (4 ml) and lithium hydroxide (49 mg, 2.05 mmol) was added followed by water (0.5 ml). The mixture was stirred overnight and then neutralised with 2M hydrochloric acid (1.02 ml, 2.04 mmol). The solvent removed in vacuo to yield the title compound as a solid. 282 mg.

MS (electrospray): m/z, [M+H]$^+$=440

Description 30

4-Bromo-5-formyl-2-hydroxybenzoic acid (D30)

To a solution of methyl 4-bromo-2-hydroxy-5-methylbenzoate (may be prepared as described in Description 14; 560 mg, 2.29 mmol) in carbon tetrachloride (10 ml) was added NBS (813 mg, 4.57 mmol) and benzoyl peroxide (44.3 mg, 0.14 mmol). The mixture was heated at 85° C. for 18 hours, then the solvent was removed in vacuo. The residue was purified by column chromatography (SiO$_2$; 6:1 cyclohexane/ethyl acetate) to give the intermediate tribromide. The intermediate was redissolved in 1,4-dioxane (6 ml) and calcium carbonate (686 mg, 6.86 mmol) and water (6 ml) were added. The mixture was heated at 150° C. in the microwave for 1.5 hours. The solvent removed and the residue was slurried in tetrahydrofuran/water (4:1, 20 ml). Lithium hydroxide (210 mg, 8.77 mmol) was added and the mixture was heated at 50° C. for 45 minutes. The solvent was removed in vacuo and to yield the title compound which was used directly in the next step without further purification. 560 mg.

MS (electrospray): m/z, [M+H]$^+$=243/245

Description 31

2-Bromo-4-{[(4-fluorophenyl)methyl]oxy}-5-({[(4-fluorophenyl)methyl]oxy}carbonyl)benzoic acid (D31)

To a solution of 4-bromo-5-formyl-2-hydroxybenzoic acid (may be prepared as described in Description 30; 560 mg, 2.29 mmol) in N,N-dimethylformamide (10 ml) was added cesium carbonate (2234 mg, 6.86 mmol) and 4-fluorobenzyl bromide (0.71 ml, 5.71 mmol). The mixture was at room temperature for 72 hours, then a further 2.5 equivalents of 4-fluorobenzyl bromide added and the mixture was heated at 60° C. for 4 hours. Ethyl acetate (15 ml) and water (15 ml) were added and the organic layer separated, washed further with water (2×10 ml), dried (MgSO$_4$) and the solvent removed in vacuo to give a solid. Purification by column chromatography (SiO$_2$; 5%-15% ethyl acetate/cyclohexane) gave the intermediate. The intermediate was redissolved in tetrahydrofuran (8 ml) and dimethyl sulfoxide (0.8 ml) and 2-methyl-1-butene (0.49 ml, 4.57 mmol) and sulfamic acid (754 mg, 7.77 mmol) were added followed by sodium chlorite (620 mg, 6.86 mmol) in water (8 ml). The mixture was stirred at 0° C. for 1 hour, then quenched with saturated sodium thiosulfate solution (10 ml). The mixture was extracted with ethyl acetate (3×15 ml), the organic layer dried (MgSO$_4$) and the solvent removed in vacuo to yield the title compound as a gum. 520 mg.

MS (electrospray): m/z, [M+H]$^+$=475/477

Description 32

(4-Fluorophenyl)methyl 2-{[(4-fluorophenyl)methyl]oxy}-4-(1-methyl-1H-pyrazol-4-yl)-5-(4-morpholinylcarbonyl)benzoate (D32)

To a solution of 2-bromo-4-{[(4-fluorophenyl)methyl]oxy}-5-({[(4-fluorophenyl)methyl]oxy}carbonyl)benzoic acid (may be prepared as described in Description 31, 520 mg, 1.09 mmol) in N,N-dimethylformamide (5 ml) was added diisopropylethylamine (0.38 ml, 2.18 mmol), morpholine (0.14 ml, 1.63 mmol), 1-hydroxy-7-azabenzotriazole (178 mg, 1.31 mmol) and EDC (355 mg, 1.85 mmol). The solution was stirred for 3 hours, the solvent was removed in vacuo and the residue purified by column chromatography (SiO$_2$; 1:1 cyclohexane/ethyl acetate) to give the intermediate as a gum. The gum was redissolved in 1,2-dimethoxyethane (5 ml) and 1-methyl-4-(4,4,5,5-tetramethyl-1,3,2-dioxaborolan-2-yl)-1H-pyrazole (227 mg, 1.09 mmol), tripotassium phosphate (463 mg, 2.18 mmol) and Pd(Ph$_3$P)$_4$ (76 mg, 0.07 mmol) were added. The mixture heated at 130° C. in a microwave for 2 hours. The solvent was removed in vacuo and the residue was purified by column chromatography (SiO$_2$, 3% 7M NH$_3$ in methanol/dichloromethane) to yield the title compound as a gum. 384 mg.

MS (electrospray): m/z, [M+H]$^+$=547

Description 33

4-Bromo-2-hydroxy-5-(4-morpholinylmethyl)benzoic acid (D33)

Methyl 4-bromo-2-hydroxy-5-(4-morpholinylmethyl)benzoate (may be prepared as described in Description 17; 350 mg, 0.96 mmol) was redissolved in tetrahydrofuran (4 ml) and lithium hydroxide (69 mg, 2.87 mmol) was added followed by water (1 ml). The mixture was heated at 50° C. for 1 hour. The mixture was cooled and the solvent removed in vacuo to yield the title compound as a brown oil. 302 mg.

MS (electrospray): m/z, [M+H]$^+$=316/318 M+H

Description 34

Phenylmethyl 4-bromo-5-(4-morpholinylmethyl)-2-[(phenylmethyl)oxy]benzoate (D34)

To a solution of 4-bromo-2-hydroxy-5-(4-morpholinylmethyl)benzoic acid (may be prepared as described in Description 33; 302 mg, 0.96 mmol) in N,N-dimethylformamide (5 ml) was added potassium carbonate (396 mg, 2.87 mmol) and benzyl bromide (0.25 ml, 2.10 mmol). The mixture was stirred at room temperature for 72 hours. Water (10 ml) and ethyl acetate (20 ml) was added and the organic layer was separated, washed with water (3×10 ml), dried (MgSO$_4$) and the solvent removed in vacuo. Purified by SP4 (20-50% ethyl acetate/hexane) to yield the title compound as an oil. 305 mg.

MS (electrospray): m/z, [M+H]$^+$=496/498

Description 35

4-Bromo-5-(4-morpholinylmethyl)-2-[(phenylmethyl)oxy]benzoic acid (D35)

To a solution of phenylmethyl 4-bromo-5-(4-morpholinylmethyl)-2-[(phenylmethyl)oxy]benzoate (may be prepared as described in Description 34; 305 mg, 0.61 mmol) in tetrahydrofuran (6 ml) was added lithium hydroxide (44.1 mg, 1.84 mmol) and water (1.5 ml). The mixture was stirred at 40° C. overnight, cooled and 2N HCl added. The solvent was removed, water (3 ml) was added and the product filtered to yield the title compound as a white solid which was used directly in the next step without further purification. 170 mg.

MS (electrospray): m/z, [M+H]$^+$=406/408.

Description 36

Phenylmethyl 5-bromo-2-[(phenylmethyl)oxy]-4-(1-piperidinylcarbonyl)benzoate (D36)

To a solution of 2-bromo-5-[(phenylmethyl)oxy]-4-{[(phenylmethyl)oxy]carbonyl}benzoic acid (may be prepared as by oxidation of phenylmethyl 5-bromo-4-formyl-2-[(phenylmethyl)oxy]benzoate—may be prepared as described in Description 24—with sulfamic acid in the presence of 2-methyl-1-butene; 436 mg, 0.99 mmol) in N,N-dimethylformamide (5 ml) was added diisopropylethylamine (0.35 ml, 1.98 mmol), piperidine (0.15 ml, 1.48 mmol), 1-hydroxy-7-azabenzotriazole (188 mg, 1.38 mmol) and EDC (379 mg, 1.98 mmol). The solution was stirred for 18 hours. Ethyl acetate (10 ml) and water (10 ml) were added. The organic layer was separated and washed further with water (2×10 ml), dried (MgSO$_4$) and the solvent removed in vacuo. Purification by column chromatography (SiO$_2$, 1:1 ethyl acetate/cyclohexane) gave the title compound as a white solid. 225 mg.

MS (electrospray): m/z [M+H]$^+$509

Description 37

Phenylmethyl 5-(1-methyl-1H-pyrazol-4-yl)-2-[(phenylmethyl)oxy]-4-(1-piperidinylcarbonyl)benzoate (D37)

Phenylmethyl 5-bromo-2-[(phenylmethyl)oxy]-4-(1-piperidinylcarbonyl)benzoate (may be prepared as described in Description 36; 225 mg, 0.40 mmol). was dissolved in 1,2-dimethoxyethane (5 ml) and 1-methyl-4-(4,4,5,5-tetramethyl-1,3,2-dioxaborolan-2-yl)-1H-pyrazole (103 mg, 0.49 mmol), tripotassium phosphate (189 mg, 0.89 mmol) and Pd(Ph$_3$P)$_4$ (27.4 mg, 0.02 mmol) were added. The mixture was heated at 125° C. for 50 minutes. Ethyl acetate (10 ml) and water (10 ml) were added and the organic layer was separated and dried (MgSO$_4$) and the solvent removed in vacuo. Purification by column chromatography (1:1 ethyl acetate/cyclohexane-10% 2M NH$_3$ in CH$_3$OH/dichloromethane) gave the title compound as a brown gum. 160 mg.

MS (electrospray): m/z [M+H]$^+$510

Description 38

5-(1-Methyl-1H-pyrazol-4-yl)-2-[(phenylmethyl)oxy]-4-(1-piperidinylcarbonyl)benzoic acid (D38)

To a solution of phenylmethyl 5-(1-methyl-1H-pyrazol-4-yl)-2-[(phenylmethyl)oxy]-4-(1-piperidinylcarbonyl)benzoate (may be prepared as described in Description 37; 194 mg, 0.38 mmol) in tetrahydrofuran (4 ml) was added lithium hydroxide (33 mg, 1.38 mmol) and water (1 ml). The solution was stirred for 18 hours then 2M hydrochloric acid (0.69 ml,

Description 39

Phenylmethyl 5-bromo-4-[(dimethylamino)carbonyl]-2-[(phenylmethyl)oxy]benzoate (D39)

To a solution of 2-bromo-5-[(phenylmethyl)oxy]-4-{[(phenylmethyl)oxy]carbonyl}benzoic acid (may be prepared as by oxidation of phenylmethyl 5-bromo-4-formyl-2-[(phenylmethyl)oxy]benzoate—may be prepared as described in Description 24—with sulfamic acid in the presence of 2-methyl-1-butene; 436 mg, 0.99 mmol) in N,N-dimethylformamide (5 ml) was added diisopropylethylamine (0.35 ml, 1.98 mmol), dimethylamine hydrochloride (121 mg, 1.48 mmol), 1-hydroxy-7-azabenzotriazole (188 mg, 1.38 mmol) and EDC (379 mg, 1.98 mmol). The solution was stirred for 18 hours. Ethyl acetate (10 ml) and water (10 ml) were added and the organic layer separated and washed further with water (2×10 ml), dried (MgSO$_4$) and the solvent removed in vacuo. Purification by column chromatography (SiO$_2$, 1:1 ethyl acetate/cyclohexane) gave the title compound as an orange gum. 195 mg.

MS (electrospray): m/z [M+H]$^+$468

Description 40

Phenylmethyl 4-[(dimethylamino)carbonyl]-5-(1-methyl-1H-pyrazol-4-yl)-2-[(phenylmethyl)oxy]benzoate (D40)

Phenylmethyl 5-bromo-4-[(dimethylamino)carbonyl]-2-[(phenylmethyl)oxy]benzoate (may be prepared as described in Description 39; 195 mg) was redissolved in 1,2-dimethoxyethane (5 ml) and 1-methyl-4-(4,4,5,5-tetramethyl-1,3,2-dioxaborolan-2-yl)-1H-pyrazole (103 mg, 0.49 mmol), tripotassium phosphate (168 mg, 0.79 mmol) and Pd(Ph$_3$P)$_4$ (34.3 mg, 0.03 mmol) were added. The mixture was heated at 125° C. for 50 minutes. Ethyl acetate (10 ml) and water (10 ml) were added. The organic layer was separated and dried (MgSO$_4$) and the solvent removed in vacuo. Purification by column chromatography (SiO$_2$, 1:1 ethyl acetate/cyclohexane-10% 2M NH$_3$ in CH$_3$OH/dichloromethane) gave the title compound as a brown gum. 195 mg.

MS (electrospray): m/z [M+H]$^+$469

Description 41

4-[(Dimethylamino)carbonyl]-5-(1-methyl-1H-pyrazol-4-yl)-2-[(phenylmethyl)oxy]benzoic acid (D41)

To a solution of phenylmethyl 4-[(dimethylamino)carbonyl]-5-(1-methyl-1H-pyrazol-4-yl)-2-[(phenylmethyl)oxy]benzoate (may be prepared as described in Description 40; 195 mg, 0.42 mmol) in tetrahydrofuran (4 ml) was added lithium hydroxide (34 mg, 1.42 mmol) and water (1 ml). The mixture was for 18 hours then 2M hydrochloric acid (0.73 ml, 1.45 mmol) was added. The solvent removed in vacuo to give the title compound as a gum. 154 mg.

MS (electrospray): m/z [M+H]$^+$379

Description 42

Methyl 4-methyl-2-(methyloxy)benzoate (D42)

To a suspension of 2-hydroxy-4-methylbenzoic acid (2.5 g, 16.43 mmol) in acetone (25 ml) was added potassium carbonate (7.49 g, 54.2 mmol) and iodomethane (4.32 ml, 69.0 mmol). The mixture was heated at 50° C. for 5 hours, cooled and the acetone was removed in vacuo. The mixture was partitioned between ethyl acetate (30 ml) and water (20 ml). The organic layer was separated, dried (MgSO$_4$) and the solvent removed in vacuo. Purification by column (SiO$_2$, 6:1 cyclohexane/ethyl acetate) gave the title compound as a solid. 2.51 g.

MS (electrospray): m/z [M+H]$^+$181

Description 43

Methyl 5-bromo-4-methyl-2-(methyloxy)benzoate (D43)

Methyl 4-methyl 2-(methyloxy)benzoate (may be prepared as described in Description 42; 2.51 g, 0.01 mmol) was dissolved in chloroform (40 ml) and cooled to 0° C. Bromine (0.72 ml, 13.97 mmol) was added dropwise over 5 minutes. The solution was stirred for one hour, then saturated aqueous sodium sulfite solution (20 ml) was added and the organic layer separated, dried (MgSO$_4$) and the solvent removed in vacuo to give the title compound as a white solid. 2.96 g.

MS (electrospray): m/z [M+H]$^+$259/261

Description 44

Methyl 4-methyl-2-(methyloxy)-5-(trifluoromethyl)benzoate (D44)

To a mixture of methyl 5-bromo-4-methyl-2-(methyloxy)benzoate (may be prepared as described in Description 43; 2.5 g, 9.65 mmol) in N,N-dimethylformamide (40 ml) was added copper (I) iodide (4.04 g, 21.23 mmol) and potassium trifluoroacetate (2.94 g, 19.30 mmol). Toluene (10 ml) was added and the mixture heated in Dean Stark apparatus at 170° C. for 45 minutes. The toluene was removed via the Dean Stark trap and the resulting mixture was heated for 18 hours at 170° C. The mixture was diluted with water (10 ml) and ethyl acetate (20 ml) and the solid was removed using Celite. The filtrate was taken and the organic layer separated, dried (MgSO$_4$) and the solvent removed in vacuo. The residue was purified by column chromatography (SiO$_2$, 50% Cyclohexane/diethyl ether) to yield the title compound as a white solid. 1.76 g.

MS (electrospray): m/z [M+H]$^+$249

Description 45

Methyl 2-hydroxy-4-methyl-5-(trifluoromethyl)benzoate (D45)

To a solution of methyl 4-methyl-2-(methyloxy)-5-(trifluoromethyl)benzoate (may be prepared as described in Description 44; 1.76 g, 7.09 mmol) in dichloromethane (70 ml) at 0° C. was added BBr$_3$ (14.89 ml, 14.89 mmol). The solution was stirred for 2 hours, 2M HCl (30 ml) was added and the organic layer removed in vacuo. The residue was partitioned between water (10 ml) and ethyl acetate (20 ml). The organic layer was separated, dried (MgSO$_4$) and the solvent removed in vacuo. The residue was purified by column chromatography (SiO$_2$, 3:1 cyclohexane/ethyl acetate) to give the title compound as an oil. 1.37 g.

MS (electrospray): Not ionisable (1.38 mmol) was added and the solvent removed in vacuo to give the title compound as a gum. 170 mg.

MS (electrospray): m/z [M+H]$^+$420

Description 46

Methyl 2-(acetyloxy)-4-methyl-5-(trifluoromethyl) benzoate (D46)

Methyl 2-hydroxy-4-methyl-5-(trifluoromethyl)benzoate (may be prepared as described in Description 45; 1.37 g, 5.85 mmol) was dissolved in pyridine (70 ml) and acetic anhydride (1.34 ml, 14.18 mmol) was added. The solution was stirred for 2 hours then the solvent was removed in vacuo to give oil. The oil was purified by column chromatography ($SiO_2$, 3:1 cyclohexane/ethyl acetate) to yield the title compound as a gum. 1.53 g.

MS (electrospray): Not ionisable

Description 47

Methyl 2-(acetyloxy)-4-(bromomethyl)-5-(trifluoromethyl)benzoate and Methyl 2-(acetyloxy)-4-(dibromomethyl)-5-(trifluoromethyl)benzoate (D47)

To a solution of methyl 2-(acetyloxy)-4-methyl-5-(trifluoromethyl)benzoate (may be prepared as described in Description 46; 1.53 g, 5.54 mmol) in carbon tetrachloride (30 ml) was added NBS (1.99 g, 11.19 mmol) and benzoyl peroxide (0.18 g, 0.55 mmol). The mixture was heated at 85° C. for 18 hours. The mixture was cooled, the solvent removed in vacuo and the residue was purified by column chromatography ($SiO_2$, 5% ethyl acetate/cyclohexane) to yield pure methyl 2-(acetyloxy)-4-(dibromomethyl)-5-(trifluoromethyl)benzoate (853 mg) and pure methyl 2-(acetyloxy)-4-(bromomethyl)-5-(trifluoromethyl)benzoate (530 mg).

Description 48

Methyl 2-hydroxy-4-(morpholinomethyl)-5-(trifluoromethyl)benzoate (D48)

To a solution of methyl 2-(acetyloxy)-4-(bromomethyl)-5-(trifluoromethyl)benzoate (may be prepared as described in Description 47; 309 mg, 0.87 mmol) in acetone (5 ml) was added triethylamine (0.24 ml, 1.74 mmol) and morpholine (0.10 ml, 1.13 mmol) the solution was stirred for 2 hours. The solvent was removed in vacuo and the residue was dissolved in ethyl acetate (10 ml), washed with water (10 ml), dried ($MgSO_4$) and the solvent removed in vacuo to give the title compound. 300 mg.

MS (electrospray): m/z $[M+H]^+$ 320

Description 49

Methyl 4-(4-morpholinylmethyl)-2-[(phenylmethyl) oxy]-5-(trifluoromethyl)benzoate (D49)

Methyl 2-hydroxy-4-(morpholinomethyl)-5-(trifluoromethyl)benzoate (may be prepared as described in Description 48; 300 mg, 0.94 mmol) was taken up in N,N-dimethylformamide (5 ml) and cesium carbonate (340 mg, 1.04 mmol) and benzyl bromide (0.16 ml, 1.31 mmol) were added. The mixture was heated at 40° C. for 18 hours. Ethyl acetate (10 ml) and water (10 ml) were added and the organic layer was separated and washed with water (2×10 ml), dried ($MgSO_4$) and the solvent removed in vacuo. Purification by column chromatography (1:1 cyclohexane/ethyl acetate-10% 7M $NH_3$ in methanol/dichloromethane) gave the title compound as oil. 248 mg.

MS (electrospray): m/z $[M+H]^+$ 410

Description 50

4-(4-Morpholinylmethyl)-2-[(phenylmethyl)oxy]-5-(trifluoromethyl)benzoic acid (D50)

Methyl 4-(4-morpholinylmethyl)-2-[(phenylmethyl)oxy]-5-(trifluoromethyl)benzoate (may be prepared as described in Description 49; 248 mg, 0.61 mmol) was dissolved in tetrahydrofuran (4 ml). LiOH (43.8 mg, 1.83 mmol) and water (1 ml) were added and the mixture heated at 40° C. for 2 hours. The mixture was cooled and 2M hydrochloric acid (0.96 ml, 1.91 mmol) was added and the solvent removed in vacuo to give the title compound. 240 mg.

MS (electrospray): m/z $[M+H]^+$ 396

Description 51

Methyl 2-hydroxy-4-(1-piperidinylmethyl)-5-(trifluoromethyl)benzoate (D51)

To a solution of methyl 2-(acetyloxy)-4-(bromomethyl)-5-(trifluoromethyl)benzoate (may be prepared as described in Description 47; 240 mg, 0.68 mmol) in acetone (5 ml) was added triethylamine (0.19 ml, 1.35 mmol) and piperidine (0.09 ml, 0.88 mmol). The solution was stirred for 18 hours. The solvent was removed in vacuo and the residue was taken up in ethyl acetate (10 ml), washed with water (10 ml), dried ($MgSO_4$) and the solvent removed in vacuo to give the title compound. 228 mg.

MS (electrospray): m/z $[M+H]^+$ 318

Description 52

Methyl 2-[(phenylmethyl)oxy]-4-(1-piperidinylmethyl)-5-(trifluoromethyl)benzoate (D52)

Methyl 2-hydroxy-4-(1-piperidinylmethyl)-5-(trifluoromethyl)benzoate (may be prepared as described in Description 51; 230 mg, 0.72 mmol) was dissolved in N,N-dimethylformamide (5 mL) and cesium carbonate (264 mg, 0.81 mmol) and benzyl bromide (0.12 ml, 1.01 mmol) were added. The mixture was heated at 40° C. for 18 hours. Ethyl acetate (10 ml) and water (10 ml) were added and the organic layer was separated and washed with water (2×10 ml), dried ($MgSO_4$) and the solvent removed in vacuo. Purification by column chromatography (1:1 cyclohexane/ethyl acetate-10% 7M $NH_3$ in methanol/dichloromethane) gave the title compound as oil. 232 mg.

MS (electrospray): m/z $[M+H]^+$ 408

Description 53

2-[(Phenylmethyl)oxy]-4-(1-piperidinylmethyl)-5-(trifluoromethyl)benzoic acid (D53)

Methyl 2-[(phenylmethyl)oxy]-4-(1-piperidinylmethyl)-5-(trifluoromethyl)benzoate (may be prepared as described in Description 52; 232 mg, 0.57 mmol) was dissolved in tetrahydrofuran (4 ml) and LiOH (38.8 mg, 1.62 mmol) and water (1 ml) were added. The mixture was heated at 40° C. for 2 hours. The mixture was cooled and 2M hydrochloric acid (0.84 ml, 1.69 mmol) was added and the solvent removed in vacuo to give the title compound as oil. 223 mg.

MS (electrospray): m/z [M+H]$^+$394

Description 54

Phenyl methyl 4-formyl-2-[(phenylmethyl)oxy]-5-(trifluoromethyl)benzoate (D54)

To a solution of methyl 2-(acetyloxy)-4-(dibromomethyl)-5-(trifluoromethyl)benzoate (may be prepared as described in Description 47; 300 mg, 0.69 mmol) in 1,4-dioxane (4 ml) was added calcium carbonate (208 mg, 2.07 mmol) and water (4 ml). The mixture was heated at 150° C. in a microwave for 4 hours. The solvent was removed in vacuo and suspended in N,N-dimethylformamide (5 ml) and cesium carbonate (563 mg, 1.73 mmol) and benzyl bromide (0.18 ml, 1.52 mmol) were added. The mixture was heated at 60° C. for one hour, cooled, and ethyl acetate (20 ml) and water (10 ml) were added. The organic layer was separated, washed further with water (2×10 ml), dried (MgSO$_4$) and solvent removed in vacuo. The residue was redissolved in N,N-dimethylformamide (5 ml) and cesium carbonate (563 mg, 1.73 mmol) and benzyl bromide (0.18 ml, 1.52 mmol) were added. The mixture was heated at 60° C. for 18 hours. The mixture was cooled, ethyl acetate (15 ml) and water (10 ml) were added. The organic layer separated, washed with water (2×10 ml), dried (MgSO$_4$) and solvent removed in vacuo. Purification by column chromatography (5% cyclohexane/ethyl acetate) yielded the title compound as oil. 80 mg.

MS (electrospray): m/z [M+H]$^+$415

Description 55

5-[(Phenylmethyl)oxy]-4-{[(phenylmethyl)oxy]carbonyl}-2-(trifluoromethyl)benzoic acid (D55)

To a solution of phenylmethyl 4-formyl-2-[(phenylmethyl)oxy]-5-(trifluoromethyl)benzoate (may be prepared as described in Description 54; 80 mg, 0.19 mmol) in tetrahydrofuran (4 ml), water (2 ml) and dimethyl sulfoxide (0.4 ml) was added sulfamic acid (63.7 mg, 0.66 mmol) and 2-methyl-1-butene (0.04 ml, 0.39 mmol). The solution was cooled to 0° C. and sodium chlorite (52.4 mg, 0.58 mmol) in water (2 ml) was added dropwise. After 60 minutes the mixture was quenched with saturated aqueous sodium thiosulfate solution (20 ml) and extracted with ethyl acetate (3×10 ml). The organic layer was dried (MgSO$_4$) and the solvent removed in vacuo to give the title compound as oil. 71 mg.

MS (electrospray): m/z [M+H]$^+$431

Description 56

Phenylmethyl 4-(4-morpholinylcarbonyl)-2-[(phenylmethyl)oxy]-5-(trifluoromethyl)benzoate (D56)

To a solution of 5-[(phenylmethyl)oxy]-4-{[(phenylmethyl)oxy]carbonyl}-2-(trifluoromethyl)benzoic acid (may be prepared as described in Description 55; 71 mg, 0.16 mmol) in N,N-dimethylformamide (4 ml) was added diisopropylethylamine (0.07 ml, 0.39 mmol), morpholine (0.03 ml, 0.29 mmol), 1-hydroxy-7-azabenzotriazole (34.2 mg, 0.25 mmol) and EDC (66.6 mg, 0.35 mmol). The mixture was stirred at room temperature for 18 hours. Ethyl acetate (10 ml) and water (10 ml) were added and the organic layer was separated, washed with water (2×10 ml), dried (MgSO$_4$) and solvent removed in vacuo. Purification by column chromatography (SiO$_2$, 1:1 ethyl acetate/cyclohexane) gave the title compound as a solid. 66 mg.

MS (electrospray): m/z [M+H]$^+$500

Description 57

Phenylmethyl 2-[(phenylmethyl)oxy]-4-(1-piperidinylcarbonyl)-5-(trifluoromethyl)benzoate (D57)

To a solution of 5-[(phenylmethyl)oxy]-4-{[(phenylmethyl)oxy]carbonyl}-2-(trifluoromethyl)benzoic acid (may be prepared as described in Description 55; 142 mg, 0.14 mmol) in N,N-dimethylformamide (4 ml) was added diisopropylethylamine (120 ul), piperidine (0.05 ml, 0.52 mmol), 1-hydroxy-7-azabenzotriazole (60 mg), and EDC (120 mg). The solution was stirred for 18 hours. Water (10 ml) and ethyl acetate (10 ml) were added and the organic layer was separated, washed with water (2×10 ml), dried (MgSO$_4$) and the solvent removed in vacuo. The residue was purified by column chromatography (SiO$_2$, 1:1 ethyl acetate/cyclohexane) to yield the title compound as a gum. 170 mg.

MS (electrospray): m/z [M+H]$^+$498

Description 58

2-[(Phenylmethyl)oxy]-4-(1-piperidinylcarbonyl)-5-(trifluoromethyl)benzoic acid (D58)

To a solution of phenylmethyl 2-[(phenylmethyl)oxy]-4-(1-piperidinylcarbonyl)-5-(trifluoromethyl)benzoate (may be prepared as described in Description 57; 170 mg, 0.34 mmol) in tetrahydrofuran (4 ml) was added LiOH (24.55 mg, 1.03 mmol) and water (1 ml). The solution was heated at 45° C. for one hour then room temperature for 18 hours. 2M hydrochloric acid (0.51 ml, 1.03 mmol) was added and the solvent removed in vacuo. The residue was partitioned between ethyl acetate (20 ml) and 2M HCl (10 ml). The organic layer was separated, dried (MgSO$_4$) and the solvent removed in vacuo to give the title compound. 139 mg.

MS (electrospray): m/z [M+H]$^+$408

Description 59

Methyl 5-chloro-2-hydroxy-4-methyl benzoate (D59)

To a solution of methyl 2-hydroxy-4-methylbenzoate (2 g, 12.04 mmol) in acetonitrile (30 ml) was added NCS (1.69 g, 12.64 mmol). The solution was heated at 100° C. for 2 hours, cooled and the solvent removed in vacuo. The residue was redissolved in dichloromethane (20 ml) and washed with water (10 ml) and NaHCO$_3$ solution (15 ml), dried (MgSO$_4$) and the solvent removed in vacuo. Purification by column (SiO$_2$, 5% ethyl acetate/cyclohexane) gave the title compound as a solid. 2.42 g.

Description 60

Methyl 2-(acetyloxy)-5-chloro-4-methyl benzoate (D60)

Methyl 5-chloro-2-hydroxy-4-methylbenzoate (may be prepared as described in Description 59; 2.42 g, 12.04 mmol) was dissolved in pyridine (10 ml) and acetic anhydride (2.39 ml, 25.3 mmol) was added. The mixture was stirred for 4 hours, then the solvent was removed in vacuo and the residue

Description 61

Methyl 2-(acetyloxy)-5-chloro-4-(dibromomethyl)benzoate (D61)

To a solution of methyl 5-chloro-2-hydroxy-4-methylbenzoate (may be prepared as described in Description 59; 2.63 g, 13.11 mmol) in carbon tetrachloride (20 ml) was added NBS (4.78 g, 26.9 mmol) and benzoyl peroxide (0.25 g, 0.79 mmol). The mixture was heated at 85° C. overnight. The mixture was cooled and the solvent removed in vacuo. The residue was purified by column chromatography (SiO$_2$, 5% ethyl acetate/cyclohexane) to give the title compound as an oil. 4.2 g.

Description 62

Phenylmethyl 5-chloro-4-formyl-2-[(phenylmethyl)oxy]benzoate (D62)

A mixture of methyl 2-(acetyloxy)-5-chloro-4-(dibromomethyl)benzoate (may be prepared as described in Description 61; 2.1 g, 5.24 mmol) and calcium carbonate (1.05 g, 10.49 mmol) in 1,4-dioxane (5 ml)/water (5 ml) was heated at 150° C. for 6 hours. The solvent was removed in vacuo and the residue was suspended in N,N-dimethylformamide (5 ml). Cesium carbonate (3.76 g, 11.54 mmol) and benzyl bromide (0.94 ml, 7.87 mmol) were added. The mixture was heated at 50° C. for 18 hours. The N,N-dimethylformamide was removed and the residue was partitioned between 2M HCl (20 ml) and ethyl acetate (15 ml). The organic layer was separated and dried (MgSO$_4$) and the solvent removed in vacuo. The residue was redissolved in N,N-dimethylformamide (5 ml) and cesium carbonate (3.76 g, 11.54 mmol) and benzyl bromide (0.94 ml, 7.87 mmol) were added. The mixture was heated for 2 hours at 50° C. and cooled, then ethyl acetate (15 ml) and water (10 ml) were added. The organic layer was washed with water (2×15 ml). The organic layer was dried (MgSO$_4$) and the solvent removed in vacuo. Purification by column chromatography (6:1 cyclohexane/ethyl acetate) gave the title compound as an off white solid. 1.4 g.

Description 63

2-Chloro-5-[(phenylmethyl)oxy]-4-{[(phenylmethyl)oxy]carbonyl}benzoic acid (D63)

To a solution of phenylmethyl 5-chloro-4-formyl-2-[(phenylmethyl)oxy]benzoate (may be prepared as described in Description 62; 1.4 g, 3.68 mmol) in tetrahydrofuran (8 ml) was added dimethyl sulfoxide (0.8 ml) and 2-methyl-1-butene (0.79 ml, 7.35 mmol), and sulfamic acid (1.21 g, 12.50 mmol). The solution was cooled to 0° C. and sodium chlorite (1.00 g, 11.03 mmol) in water (8 ml) was added. The mixture was stirred for one hour, then saturated sodium thiosulfate solution was added (15 ml) and the mixture was stirred for another 10 minutes, The mixture was extracted with ethyl acetate (3×20 ml) and the organic layer was washed with water (10 ml) and 2M HCl (10 ml), dried (MgSO$_4$) and the solvent removed in vacuo to give the title compound as an off white solid. 1.46 g.

MS (electrospray): m/z [M+H]$^+$395

Description 64

Phenylmethyl 5-chloro-4-[(3,3-difluoro-1-pyrrolidinyl)carbonyl]-2-[(phenylmethyl)oxy]benzoate (D64)

To a solution of 2-chloro-5-[(phenylmethyl)oxy]-4-{[(phenylmethyl)oxy]carbonyl}benzoic acid (may be prepared as described in Description 63; 480 mg, 1.21 mmol) in N,N-dimethylformamide (5 ml) was added diisopropylethylamine (0.63 ml, 3.63 mmol), 3,3-difluoropyrrolidine (208 mg, 1.45 mmol), 1-hydroxy-7-azabenzotriazole (198 mg, 1.45 mmol) and EDC (417 mg, 2.18 mmol). The solution was stirred for 18 hours, then water (10 ml) and ethyl acetate (15 ml) were added and the organic layer was separated. The organic layer was washed further with water (2×10 ml), dried (MgSO$_4$) and the solvent removed in vacuo. Purification by column chromatography (2:1-1:1 cyclohexane/ethyl acetate) gave the title compound as a orange solid. 444 mg.

MS (electrospray): m/z [M+H]$^+$486.

Description 65

5-Chloro-4-[(3,3-difluoro-1-pyrrolidinyl)carbonyl]-2-[(phenylmethyl)oxy]benzoic acid (D65)

Phenylmethyl 5-chloro-4-[(3,3-difluoro-1-pyrrolidinyl)carbonyl]-2-[(phenylmethyl)oxy]benzoate (may be prepared as described in Description 64; 444 mg, 0.92 mmol) was dissolved in tetrahydrofuran (4 ml) and LiOH (66.6 mg, 2.78 mmol) and water (1 ml) were added. The solution was heated at 45° C. for 90 minutes. 2M Hydrochloric acid (1.39 ml, 2.78 mmol) was added and the solvent was removed in vacuo. The solid was partitioned between 2M HCl (5 ml) and ethyl acetate (40 ml), and the organic layer separated, dried (MgSO$_4$) and the solvent removed in vacuo to give the title compound as a brown solid. 374 mg.

MS (electrospray): m/z [M+H]$^+$396

Description 66

Phenylmethyl 5-chloro-4-(4-morpholinylcarbonyl)-2-[(phenylmethyl)oxy]benzoate (D66)

To a solution of 2-chloro-5-[(phenylmethyl)oxy]-4-{[(phenylmethyl)oxy]carbonyl}benzoic acid (may be prepared as described in Description 63; 480 mg, 1.21 mmol) in N,N-dimethylformamide (5 ml) was added diisopropylethylamine (0.63 ml, 3.63 mmol), morpholine (0.13 ml, 1.45 mmol), 1-hydroxy-7-azabenzotriazole (198 mg, 1.45 mmol) and EDC (417 mg, 2.18 mmol). The solution was stirred for 18 hours. Water (10 ml) and ethyl acetate (15 ml) were added and the organic layer was separated. The organic layer was washed further with water (2×10 ml), dried (MgSO$_4$) and the solvent removed in vacuo. Purification by column chromatography (SiO$_2$, 1:1 cyclohexane/ethyl acetate) gave the title compound as an orange solid. 381 mg.

MS (electrospray): m/z [M+H]$^+$466.

Description 67

5-Chloro-4-(4-morpholinylcarbonyl)-2-[(phenylmethyl)oxy]benzoic acid (D67)

Phenylmethyl 5-chloro-4-(4-morpholinylcarbonyl)-2-[(phenylmethyl)oxy]benzoate (may be prepared as described in Description 66; 381 mg, 0.82 mmol) was redissolved in tetrahydrofuran (4 ml) and LiOH (64 mg, 2.67 mmol) and water (1 ml) were added. The solution was heated at 45° C. for 90 minutes, 2M hydrochloric acid (1.33 ml, 2.66 mmol) was added and the solvent removed in vacuo. The solid was partitioned between 2M HCl (5 ml) and ethyl acetate (40 ml). The organic layer was dried (MgSO$_4$) and the solvent removed in vacuo to give a brown solid. 381 mg.

MS (electrospray): m/z [M+H]$^+$376.

Description 68

2-((4-fluorobenzyl)oxy)-5-(1-methyl-1H-pyrazol-4-yl)-4-(morpholine-4-carbonyl)benzoic acid. (D68)

To a solution of 4-fluorobenzyl 5-bromo-2-((4-fluorobenzyl)oxy)-4-(morpholine-4-carbonyl)benzoate (380 mg, 0.696 mmol) (may be prepared as described in description D19) in 1,2-Dimethoxyethane (DME) (10 mL)/Water (1.00 mL) was added 1-methyl-4-(4,4,5,5-tetramethyl-1,3,2-dioxaborolan-2-yl)-1H-pyrazole (217 mg, 1.043 mmol), Tetrakis (48.2 mg, 0.042 mmol), tripotassium phosphate (295 mg, 1.391 mmol). The vial was sealed and heated to 130° C. for 25 min. Mixture was diluted with water (50 ml) and extracted with ethyl acetate (3×50 ml), the organics were combined, dried (MgSO4) and evaporated on a buchi under reduced pressure. No attempt was made to purify this intermediate it was taken up into a mixture of Tetrahydrofuran (THF) (10.00 mL)/Water (1.00 mL) and lithium hydroxide (33.3 mg, 1.391 mmol) was added. The mixture was then heated to 80° C. for 3 hrs. The mixture on cooling was diluted with water (50 ml) and acidified to pH2 using 2M aqueous HCl. The solid formed was filtered off, washed with water (2×20 ml) and dried in air under vacuum to give the title compound as an off white solid.

Yield: 300 mg

MS (electrospray): m/z [M+H]+440.

Description 69

2-(Benzyloxy)-5-bromo-N-(3-chlorophenyl)-4-(morpholinomethyl)benzamide (D69)

To a solution of 5-Bromo-4-(4-morpholinylmethyl)-2-[(phenylmethyl)oxy]benzoic acid (may be prepared as described in D7) (1 g, 2.461 mmol) in N,N-Dimethylformamide (DMF) (20 mL) was added EDC (0.849 g, 4.43 mmol), 1-hydroxy-7-azabenzotriazole (0.503 g, 3.69 mmol), 3-chloroaniline (0.504 mL, 4.92 mmol), DIPEA (0.860 mL, 4.92 mmol) and the mixture was stirred at room temperature overnight. The DMF was removed on a buchi under reduced pressure, the residue was taken up into DCM (50 ml) and washed with water (2×20 ml). The DCM was evaporated on a buchi under reduced pressure and the residue was purified using the Companion eluting with 0-50% ethyl acetate/cyclohexane to give the title compound as pale yellow oil which solidified on standing. Yield: 400 mg MS (electrospray): m/z [M+H]+517.

Description 70

Methyl 5-chloro-2-hydroxy-4-methylbenzoate (D70)

To a solution of methyl 2-hydroxy-4-methylbenzoate (2 g, 12.04 mmol) in acetonitrile (30 mL) was added NCS (1.688 g, 12.64 mmol). The solution was stirred at 100° C. for 2 hours and then cooled. The solvent was removed in vacuo. The residue was redissolved in DCM (20 mL), washed with water (10 mL) and NaHCO$_3$ solution (15 mL), dried over MgSO$_4$ and the solvent removed in vacuo. Purification by column (Si, Isolute, 5% EtOAc/Cyclohexane) gave the title product as a solid (2.42 g, 100% yield).

$^1$H NMR (400 MHz, CDCl$_3$): 2.38 (3H, s), 3.95 (3H, s), 6.88 (1H, s), 7.80 (1H, s), 10.58 (1H, s).

Description 71

Methyl 2-acetoxy-5-chloro-4-methylbenzoate (D71)

To a solution of methyl 2-acetoxy-5-chloro-4-methylbenzoate (may be prepared as described in D70) (2.42 g, 12.04 mmol) in pyridine (10 mL) was added acetic anhydride (2.385 mL, 25.3 mmol). The solution was stirred for 4 hours, and then the solvent was removed in vacuo. The residue was purified by column (Si, Isolute, 3:1 Cyclohexane/EtOAc) to give the title product as oil (2.64 g, 90% yield).

$^1$H NMR (400 MHz, CDCl$_3$): 2.35 (3H, s), 2.42 (3H, s), 3.87 (3H, s), 7.00 (1H, s), 8.01 (1H, s).

Description 72

Methyl 2-acetoxy-5-chloro-4-(dibromomethyl)benzoate (D72)

To a solution of methyl 5-chloro-2-hydroxy-4-methylbenzoate (may be prepared as described in D71) (2.63 g, 13.11 mmol) in carbon tetrachloride (20 mL) were added NBS (4.78 g, 26.9 mmol) and benzoyl peroxide (0.254 g, 0.787 mmol). The mixture was stirred at 85° C. overnight and then cooled. The solvent was removed in vacuo. Purification by column (Si, Isolute, 5% EtOAc/Cyclohexane) gave the title product as oil (4.2 g, 80% yield).

$^1$H NMR (400 MHz, CDCl$_3$): 2.38 (3H, s), 3.90 (3H, s), 7.00 (1H, s), 7.75 (1H, s), 8.00 (1H, s).

LCMS: MH$^+$=401

Description 73

Benzyl 2-(benzyloxy)-5-chloro-4-formyl benzoate (D73)

A mixture of methyl 2-(acetyloxy)-5-chloro-4-(dibromomethyl)benzoate (may be prepared as described in D72) (2.1 g, 5.24 mmol) and calcium carbonate (1.050 g, 10.49 mmol) in 1,4-dioxane (5 mL)/water (5.00 mL) was stirred at 150° C. for 6 hour 20 minutes. The solvent was removed in vacuo. The residue was suspended in N,N-Dimethylformamide (DMF) (5.00 mL) and cesium carbonate (3.76 g, 11.54 mmol) and benzyl bromide (0.936 mL, 7.87 mmol) were added. The mixture was stirred at 50° C. for 2 hours and then cooled. EtOAc (15 mL) and water (10 mL) were added and the organic layer was washed further with water (2×15 mL), dried over MgSO$_4$ and concentrated in vacuo. Purification by column (6:1 Cyclohexane/EtOAc) gave the title product as an off-white solid (1.4 g, 70% yield).
LCMS: MH$^+$=381

Description 74

5-(Benzyloxy)-4-((benzyloxy)carbonyl)-2-chlorobenzoic acid (D74)

To a solution of benzyl 2-(benzyloxy)-5-chloro-4-formylbenzoate (may be prepared as described in D73) (1.4 g, 3.68 mmol) in tetrahydrofuran (THF) (8 mL) and dimethyl sulfoxide (DMSO) (0.8 mL) were added 2-methyl-1-butene (0.792 mL, 7.35 mmol) and sulfamic acid (1.214 g, 12.50 mmol). The solution was cooled to 0° C. and a solution of sodium chlorite (0.997 g, 11.03 mmol) in water (8 mL) was added. The mixture was stirred for one hour, then saturated sodium thiosulfate solution was added (15 mL) and the mixture was stirred for another 10 minutes. The mixture was extracted with EtOAc (3×20 mL). The organic layer was washed with water (10 mL) and 2M HCl (10 mL), dried over MgSO$_4$ and concentrated in vacuo to give the title product as an off-white solid (1.46 g, 100% yield).
LCMS: [M−H]$^−$=395

Description 75

Benzyl 2-(benzyloxy)-5-chloro-4-(4-methylpiperazine-1-carbonyl)benzoate (D75)

To a solution of 5-(benzyloxy)-4-((benzyloxy)carbonyl)-2-chlorobenzoic acid (may be prepared as described in D74) (500 mg, 1.260 mmol) in N,N-Dimethylformamide (DMF) (5 mL) were added DIPEA (0.660 mL, 3.78 mmol), 1-methylpiperazine (0.182 mL, 1.638 mmol), 1-hydroxy-7-azabenzotriazole (206 mg, 1.512 mmol) and EDC (435 mg, 2.268 mmol). The mixture was stirred at room temperature for 8 hrs. The solvent was removed in vacuo. The residue was redissolved in DCM (10 mL) and washed with water (10 mL), dried over MgSO$_4$ and concentrated in vacuo. Purification by column (Si, Isolute, 10% 2M NH3 in MeOH/DCM) gave the title product as a yellow solid (400 mg, 66% yield).
LCMS: MH$^+$=479

Description 76

2-(benzyloxy)-5-chloro-4-(4-methylpiperazine-1-carbonyl)benzoic acid (D76)

To a solution of benzyl 2-(benzyloxy)-5-chloro-4-(4-methylpiperazine-1-carbonyl)benzoate (may be prepared as described in D75) (400 mg, 0.837 mmol) in tetrahydrofuran (THF) (5.00 mL) were added lithium hydroxide (63.4 mg, 2.65 mmol) and water (1.5 mL). The mixture was stirred at 40° C. for 2 hours. After cooling, 2M hydrochloric acid (1.386 mL, 2.77 mmol) was added. The solvent was removed in vacuo to give the title product as a crude solid (324 mg, assuming 100% yield).
LCMS: MH$^+$=389

Example 1

5-Bromo-4-(4-morpholinylmethyl)-2-[(phenylmethyl)oxy]-N-4-pyridazinylbenzamide (E1)

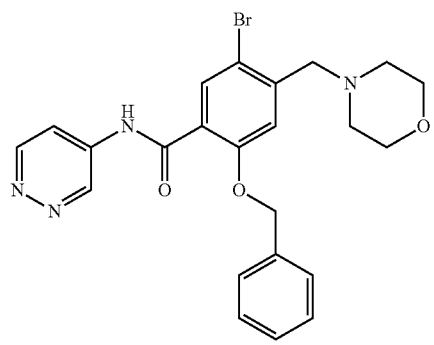 [SMILES: O=C(Nc1ccnnc1)c1cc(Br)c(CN2CCOCC2)cc1OCc1ccccc1]

Diisopropylethylamine (0.08 ml, 0.47 mmol), HOBT (43.0 mg, 0.28 mmol), 4-pyridazinamine (33.4 mg, 0.35 mmol) and EDC (90 mg, 0.47 mmol) were added to a solution of 5-bromo-4-(4-morpholinylmethyl)-2-[(phenylmethyl)oxy] benzoic acid (may be prepared as described in Description 7; 95 mg, 0.23 mmol) in N,N-dimethylformamide (5 ml). The mixture was stirred overnight, the solvent removed in vacuo and the solid recrystallised with 1:1 methanol/DMSO to give the title compound as a white solid. 56.1 mg.
MS (electrospray): m/z [M+H]$^+$483/485
$^1$H NMR (DMSO-d$_6$): 2.29-2.43 (4H, m), 3.50-3.63 (6H, m), 5.30 (2H, s), 7.24-7.40 (4H, m), 7.49 (2H, d, J=6.80 Hz), 7.83 (1H, s), 8.02 (1H, dd, J=5.92, 2.63 Hz), 9.07 (1H, dd, J=5.92, 0.88 Hz), 9.19-9.30 (1H, m) 10.82 (1H, s)

Example 2

5-Bromo-4-(4-morpholinylmethyl)-2-[(phenylmethyl)oxy]-N-3-pyridinylbenzamide (E2)

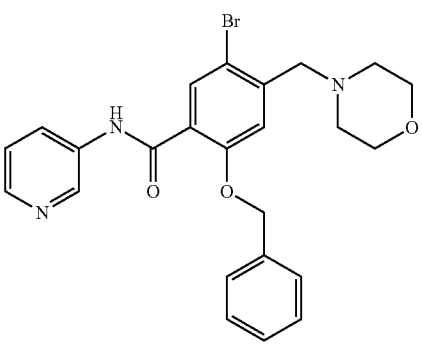 [SMILES: O=C(Nc1cccnc1)c1cc(Br)c(CN2CCOCC2)cc1OCc1ccccc1]

Diisopropylethylamine (72.2 μl, 0.414 mmol), HOBT (38.0 mg, 0.248 mmol), 3-aminopyridine (29.2 mg, 0.310 mmol) and EDC (79 mg, 0.414 mmol) To a solution of 5-bromo-4-(4-morpholinylmethyl)-2-[(phenylmethyl)oxy] benzoic acid (may be prepared as described in Description 7;

84 mg, 0.207 mmol) in N,N-dimethylformamide was added. The reaction was stirred over the weekend, then the solvent was removed in vacuo. Purification by MDAP gave the title compound as a white solid. 30 mg.

MS (electrospray): m/z [M+H]$^+$ 484/486

$^1$H NMR (DMSO-d$_6$): 2.30-2.44 (4H, m), 3.52-3.65 (6H, m), 5.31 (2H, s), 7.26-7.43 (5H, m), 7.51 (2H, d, J=6.80 Hz), 7.84 (1H, s), 8.01-8.16 (1H, m), 8.29 (1H, dd, J=4.71, 1.43 Hz), 8.70 (1H, d, J=2.41 Hz), 10.38 (1H, s)

Method B

Diisopropylethylamine (132 μl, 0.76 mmol), HOBT (69.7 mg, 0.46 mmol), 3-aminopyridine (53.5 mg, 0.57 mmol) and EDC (145 mg, 0.76 mmol) were added to a solution of 5-bromo-4-(4-morpholinylmethyl)-2-[(phenylmethyl)oxy] benzoic acid (may be prepared as described in Description 7; 154 mg, 0.38 mmol) in N,N-dimethylformamide. The reaction was stirred overnight, then the solvent was removed in vacuo. Purification by MDAP yielded the title compound as a white solid. 42 mg.

MS (electrospray): m/z [M+H]$^+$ 481/483

Example 3

5-(1-Methyl-1H-pyrazol-4-yl)-4-(4-morpholinylmethyl)-2-[(phenylmethyl)oxy]-N-4-pyridazinylbenzamide (E3)

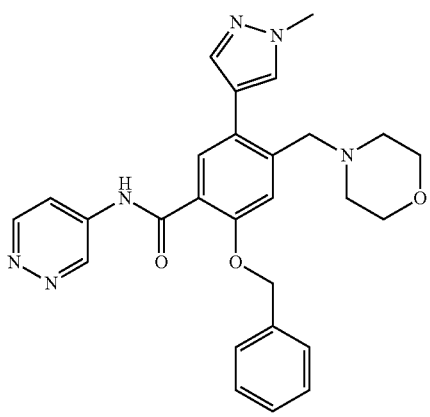 [SMILES: Cn1cc(-c2cc(C(=O)Nc3ccnnc3)c(OCc3ccccc3)cc2CN2CCOCC2)cn1]

Na$_2$CO$_3$ (0.25 ml, 0.25 mmol) and palladium tetrakis (8.61 mg, 7.45 μmol) was added to 5-bromo-4-(4-morpholinylmethyl)-2-[(phenylmethyl)oxy]-N-4-pyridazinylbenzamide (may be prepared as described in Example 1; 60 mg, 0.12 mmol) and (1-methyl-1H-pyrazol-4-yl)boronic acid (18.76 mg, 0.149 mmol) in 1,2-dimethoxyethane (3 ml). The mixture was heated at 120° C. in a microwave for one hour and the solvent was removed in vacuo. The residue was purified by MDAP to yield the title compound as a white solid. 8 mg.

MS (electrospray): m/z [M+H]$^+$ 485

$^1$H NMR (DMSO-d$_6$): 2.32 (4H, br. s.), 3.14-3.48 (8H, m), 3.88 (3H, s), 5.32 (2H, s), 7.25-7.40 (4H, m), 7.51 (1H, d, J=7.02 Hz), 7.64 (2H, s), 7.95 (1H, s), 8.05 (1H, dd, J=5.81, 2.74 Hz), 8.17 (1H, s), 9.06 (1H, d, J=5.92 Hz), 9.27 (1H, d, J=1.97 Hz), 10.78 (1H, s)

Example 4

5-(1-Methyl-1H-pyrazol-4-yl)-4-(4-morpholinylmethyl)-2-[(phenylmethyl)oxy]-N-3-pyridinylbenzamide (E4)

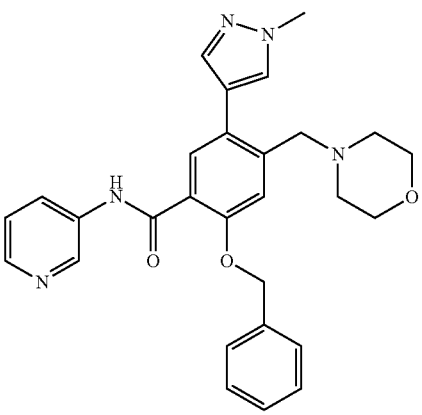 [SMILES: Cn1cc(-c2cc(C(=O)Nc3cccnc3)c(OCc3ccccc3)cc2CN2CCOCC2)cn1]

Na$_2$CO$_3$ (0.23 ml, 0.23 mmol) and palladium tetrakis (7.91 mg, 6.84 μmol) were added to 5-bromo-4-(4-morpholinylmethyl)-2-[(phenylmethyl)oxy]-N-3-pyridinylbenzamide (may be prepared as described in Example 2; 55 mg, 0.11 mmol) and (1-methyl-1H-pyrazol-4-yl)boronic acid (17.23 mg, 0.137 mmol) in 1,2-dimethoxyethane (3 ml). The mixture was heated at 120° C. in a microwave for one hour and the solvent was removed in vacuo. The residue was purified by MDAP to yield the title compound as a white solid. 27 mg.

MS (electrospray): m/z [M+H]$^+$ 484

$^1$H NMR (DMSO-d$_6$): 2.33 (4H, br. s.), 3.16-3.62 (9H, m), 5.33 (2H, s), 7.25-7.43 (5H, m), 7.46-7.59 (2H, m), 7.67 (2H, d, J=5.48 Hz), 7.95 (1H, s), 8.12 (1H, d, J=8.55 Hz), 8.22-8.35 (1H, m), 8.72 (1H, d, J=2.19 Hz), 10.39 (1H, s)

Example 5

5-Bromo-4-methyl-2-[(phenylmethyl)oxy]-N-4-pyridazinyl benzamide (E5)

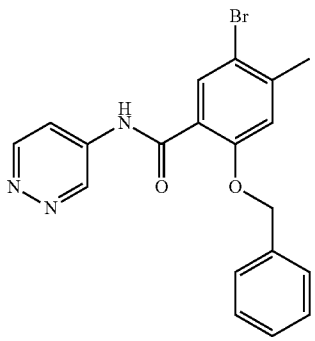 [SMILES: Cc1cc(OCc2ccccc2)c(C(=O)Nc2ccnnc2)cc1Br]

4-Pyridazinamine (207 mg, 2.18 mmol), diisopropylethylamine (0.52 ml, 2.97 mmol) and HATU (904 mg, 2.38 mmol) were added to a solution of 5-bromo-4-methyl-2-[(phenylmethyl)oxy]benzoic acid (may be prepared as described in Description 9; 636 mg, 1.98 mmol) in N,N-dimethylformamide (10 ml). The mixture was stirred for 2 hours, after 10 minutes a solid had crashed out of solution. The solid was filtered and washed with ethyl acetate (10 ml) to yield the title compound. 475 mg.

MS (electrospray): m/z [M+H]⁺398/400

¹H NMR (DMSO-d₆): 2.42 (3H, s), 5.25 (2H, s), 7.28-7.43 (4H, m), 7.51 (2H, dd, J=7.78, 1.43 Hz), 7.82 (1H, s), 7.99 (1H, dd, J=5.92, 2.85 Hz), 9.05 (1H, dd, J=5.92, 0.88 Hz), 9.13-9.23 (1H, m), 10.72 (1H, s)

Example 6

5-Bromo-4-methyl-2-[(phenylmethyl)oxy]-N-3-pyridinylbenzamide (E6)

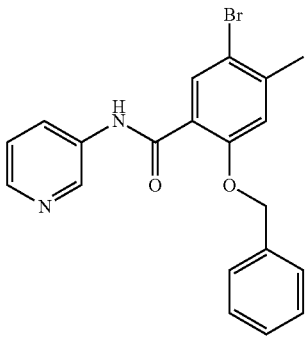 [SMILES: Cc1cc(OCc2ccccc2)c(C(=O)Nc2cccnc2)cc1Br]

3-Aminopyridine (193 mg, 2.06 mmol), and HATU (852 mg, 2.24 mmol) were added to a solution of 5-bromo-4-methyl-2-[(phenylmethyl)oxy]benzoic acid (may be prepared as described in Description 9; 600 mg, 1.87 mmol) in N,N-dimethylformamide (10 ml). The reaction was stirred overnight and the solid was filtered. Solvent was removed in vacuo and water was added. The solid was filtered and washed with ethyl acetate (10 ml) to give a white solid. The products were combined to yield the title compound as an off white solid. 508 mg.

MS (electrospray): m/z [M+H]⁺397/399

¹H NMR (DMSO-d₆): 2.42 (3H, s), 5.26 (2H, s), 7.28-7.42 (5H, m), 7.54 (2H, d, J=7.23 Hz), 7.84 (1H, s), 8.06 (1H, d, J=8.33 Hz), 8.27 (1H, d, J=4.60 Hz), 8.62 (1H, d, J=2.19 Hz), 10.31 (1H, s)

Example 7

4-Methyl-5-(1-methyl-1H-pyrazol-4-yl)-2-[(phenylmethyl)oxy]-N-3-pyridinylbenzamide (E7)

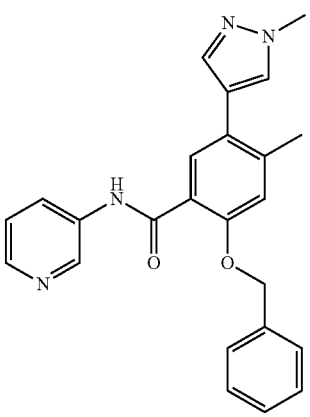 [SMILES: Cc1cc(OCc2ccccc2)c(C(=O)Nc2cccnc2)cc1-c1cnn(C)c1]

1-Methyl-4-(4,4,5,5-tetramethyl-1,3,2-dioxaborolan-2-yl)-1H-pyrazole (86 mg, 0.42 mmol), palladium tetrakis (26.2 mg, 0.02 mmol) and Na₂CO₃ (0.76 ml, 0.76 mmol) were added to a solution of 5-bromo-4-methyl-2-[(phenylmethyl)oxy]-N-3-pyridinylbenzamide (may be prepared as described in Example 6; 150 mg, 0.38 mmol) in 1,2-dimethoxyethane (3 ml). The mixture was heated at 120° C. in a microwave for 1 hour. The solvent was removed in vacuo and the residue purified by MDAP to yield the title compound as a white solid. 73 mg.

MS (electrospray): m/z [M+H]⁺399

¹H NMR (DMSO-d₆): 2.44 (3H, s), 3.88 (3H, s), 5.28 (2H, s), 7.25 (1H, s), 7.30-7.45 (4H, m), 7.57 (2H, d, J=6.58 Hz), 7.66 (1H, s), 7.70 (1H, s), 7.96 (1H, s), 8.07 (1H, dd, J=8.33, 1.53 Hz), 8.26 (1H, dd, J=4.60, 1.32 Hz), 8.62 (1H, d, J=2.41 Hz), 10.29 (1H, s)

Example 8

4-Methyl-5-(1-methyl-1H-pyrazol-4-yl)-2-[(phenylmethyl)oxy]-N-4-pyridazinylbenzamide (E8)

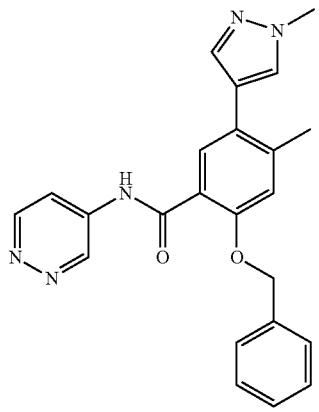 [SMILES: Cc1cc(OCc2ccccc2)c(C(=O)Nc2ccnnc2)cc1-c1cnn(C)c1]

1-Methyl-4-(4,4,5,5-tetramethyl-1,3,2-dioxaborolan-2-yl)-1H-pyrazole (86 mg, 0.42 mmol), palladium tetrakis (26.1 mg, 0.02 mmol) and Na₂CO₃ (0.75 ml, 0.75 mmol) were added to a solution of 5-bromo-4-methyl-2-[(phenylmethyl)oxy]-N-4-pyridazinylbenzamide (may be prepared as described in Example 5; 150 mg, 0.38 mmol) in 1,2-dimethoxyethane (3 ml).

The mixture was heated at 120° C. in a microwave for 1 hour. The solvent was removed in vacuo. The residue was triturated with methanol (5 ml) and the solid filtered to give the title compound as an off white solid. 90 mg.

MS (electrospray): m/z [M+H]⁺400

¹H NMR (DMSO-d₆): 2.44 (3H, s), 3.88 (3H, s), 5.27 (2H, s), 7.25 (1H, s), 7.30-7.43 (3H, m), 7.54 (2H, d, J=6.58 Hz), 7.66 (2H, d, J=7.02 Hz), 7.92-8.04 (2H, m), 9.03 (1H, d, J=5.92 Hz), 9.16 (1H, d, J=1.97 Hz), 10.67 (1H, br. s.)

Example 9

4-Bromo-5-methyl-2-[(phenylmethyl)oxy]-N-3-pyridinylbenzamide (E9)

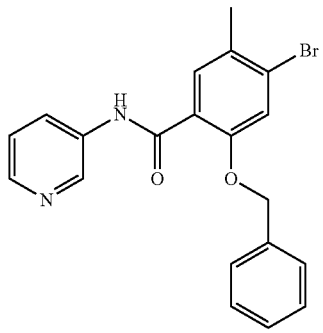 [SMILES: Cc1cc(C(=O)Nc2cccnc2)c(OCc2ccccc2)cc1Br]

3-Aminopyridine (52.7 mg, 0.56 mmol), diisopropylethylamine (0.16 ml, 0.93 mmol) and HATU (266 mg, 0.70 mmol) were added to a solution of 4-bromo-5-methyl-2-[(phenylmethyl)oxy]benzoic acid (may be prepared as described in Description 12; 150 mg, 0.47 mmol) in N,N-dimethylformamide (3 ml). The solution was stirred overnight and the solid filtered to give the product as a white solid (76 mg). A 2nd crop was obtained (31 mg). The two crops were combined to yield the title compound as a white solid. 107 mg.

MS (electrospray): m/z [M+H]$^+$397/399

$^1$H NMR (DMSO-d$_6$): 2.34 (3H, s), 5.26 (2H, s), 7.30-7.41 (4H, m), 7.46-7.58 (3H, m), 7.66 (1H, s), 8.01-8.10 (1H, m), 8.28 (1H, dd, J=4.60, 1.53 Hz), 8.66 (1H, d, J=2.41 Hz), 10.31 (1H, s)

Example 10

4-Bromo-5-methyl-2-[(phenylmethyl)oxy]-N-4-pyridazinylbenzamide (E10)

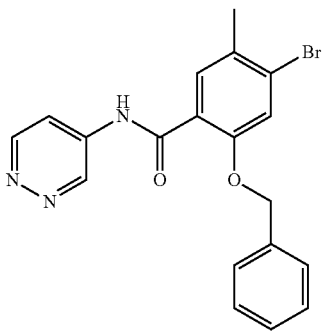 [SMILES: Cc1cc(C(=O)Nc2ccnnc2)c(OCc2ccccc2)cc1Br]

4-Aminopyridazine (53.3 mg, 0.56 mmol), diisopropylethylamine (0.16 ml, 0.93 mmol) and HATU (266 mg, 0.70 mmol) were added to a solution of 4-bromo-5-methyl-2-[(phenylmethyl)oxy]benzoic acid (may be prepared as described in Description 12; 150 mg, 0.47 mmol) in N,N-dimethylformamide (3 ml). The mixture was stirred overnight. The solid was filtered and washed with water (2 ml) and methanol (3 ml) to give the product as a white solid (80 mg). A 2nd crop was obtained (33 mg). The crops were combined to yield the title compound as a white solid. 113 mg.

MS (electrospray): m/z [M+H]$^+$398/400

$^1$H NMR (DMSO-d$_6$): 2.34 (3H, s), 5.25 (2H, s), 7.25-7.41 (3H, m), 7.48 (2H, dd, J=7.67, 1.53 Hz), 7.57 (1H, s), 7.64 (1H, s), 7.99 (1H, dd, J=5.92, 2.63 Hz), 9.05 (1H, dd, J=5.92, 1.10 Hz), 9.20 (1H, dd, J=2.74, 0.99 Hz), 10.73 (1H, s)

Example 11

5-Methyl-4-(1-methyl-1H-pyrazol-4-yl)-2-[(phenylmethyl)oxy]-N-3-pyridinylbenzamide (E11)

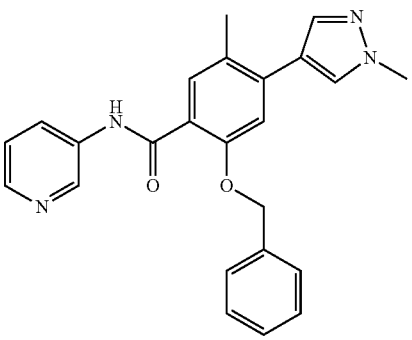 [SMILES: Cc1cc(C(=O)Nc2cccnc2)c(OCc2ccccc2)cc1-c1cnn(C)c1]

Sodium carbonate (0.30 ml, 0.30 mmol) was added to 4-bromo-5-methyl-2-[(phenylmethyl)oxy]-N-3-pyridinylbenzamide (may be prepared as described in Example 9; 59 mg, 0.15 mmol), 1-methyl-4-(4,4,5,5-tetramethyl-1,3,2-dioxaborolan-2-yl)-1H-pyrazole (37.1 mg, 0.18 mmol) and palladium tetrakis (10.30 mg, 8.91 µmol) in 1,2-dimethoxyethane (3 ml). The mixture was heated in a microwave at 120° C. for 1 hour, the solvent was removed in vacuo and the solid purified by MDAP to yield the title compound as a white solid. 30 mg.

MS (electrospray): m/z [M+H]$^+$399

$^1$H NMR (DMSO-d$_6$): 2.38 (3H, s), 3.92 (3H, s), 5.32 (2H, s), 7.24-7.44 (5H, m), 7.52-7.67 (3H, m), 7.84 (1H, s), 8.01-8.15 (2H, m), 8.18 (1H, s), 8.26 (1H, dd, J=4.60, 1.10 Hz), 8.60 (1H, d, J=2.19 Hz), 10.28 (1H, s)

Example 12

5-Methyl-4-(1-methyl-1H-pyrazol-4-yl)-2-[(phenylmethyl)oxy]-N-4-pyridazinylbenzamide (E12)

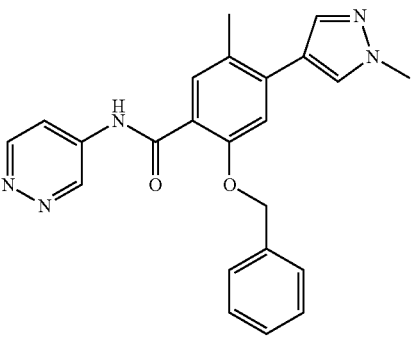 [SMILES: Cc1cc(C(=O)Nc2ccnnc2)c(OCc2ccccc2)cc1-c1cnn(C)c1]

Sodium carbonate (0.32 ml, 0.32 mmol) was added to 4-bromo-5-methyl-2-[(phenylmethyl)oxy]-N-4-pyridazinylbenzamide (may be prepared as described in Example 10; 64 mg, 0.16 mmol), 1-methyl-4-(4,4,5,5-tetramethyl-1,3,2-dioxaborolan-2-yl)-1H-pyrazole (40.1 mg, 0.19 mmol) and Pd(Ph$_3$P)$_4$ (11.14 mg, 9.64 μmol) in 1,2-dimethoxyethane (3 ml). The mixture was heated in a microwave at 120° C. for 1 hour, the solvent was removed in vacuo and the solid triturated with DMSO/methanol (1:1, 1 ml) to yield the title compound as a white solid. 9 mg.

MS (electrospray): m/z [M+H]$^+$400

$^1$H NMR (DMSO-d$_6$): 2.38 (3H, s), 3.92 (3H, s), 5.31 (2H, s), 7.19-7.45 (4H, m), 7.47-7.64 (3H, m), 7.85 (1H, s), 8.01 (1H, dd, J=5.81, 2.74 Hz), 8.13 (1H, s), 9.04 (1H, d, J=5.70 Hz), 9.14 (1H, d, J=1.97 Hz), 10.65 (1H, s)

Example 13

2-{[(4-Fluorophenyl)methyl]oxy}-4-(1-methyl-1H-pyrazol-4-yl)-5-(4-morpholinylmethyl)-N-3-pyridinylbenzamide (E13)

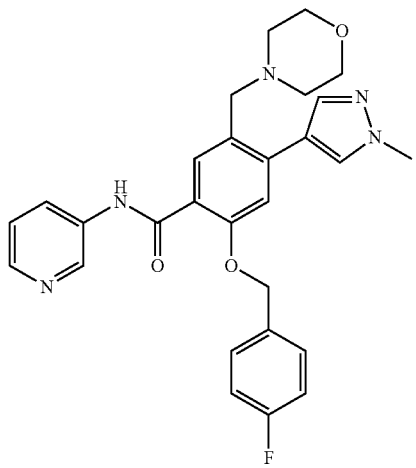 [SMILES: Cn1cc(-c2cc(OCc3ccc(F)cc3)c(C(=O)Nc3cccnc3)cc2CN2CCOCC2)cn1]

To a solution of methyl 2-{[(4-fluorophenyl)methyl]oxy}-4-(1-methyl-1H-pyrazol-4-yl)-5-(4-morpholinylmethyl)benzoate (may be prepared as described in Description 18; 155 mg, 0.353 mmol) in tetrahydrofuran (4 ml) was added lithium hydroxide (31 mg, 1.29 mmol) followed by water (1 ml). The mixture was heated at 50° C. for one hour. 2M hydrochloric acid (0.79 ml, 1.59 mmol) was added and the solvent removed in vacuo. The residue was redissolved in N,N-dimethylformamide (4 ml) and diisopropylethylamine (0.12 ml, 0.71 mmol), 3-aminopyridine (43.2 mg, 0.46 mmol), 1-hydroxy-7-azabenzotriazole (57.6 mg, 0.42 mmol) and EDC (101 mg, 0.53 mmol) were added. The solution was stirred overnight, then the solvent was removed in vacuo to give a residue. Purification by MDAP yielded the title compound as a white solid. 84 mg.

MS (electrospray): m/z, [M+H]$^+$=502

$^1$H NMR (400 MHz, DMSO-d$_6$); 2.35-2.44 (4H, m), 3.44-3.50 (2H, m), 3.59 (4H, t, J=4.14 Hz), 3.87-3.98 (3H, m), 5.31 (2H, s), 7.15-7.27 (2H, m), 7.28-7.40 (2H, m), 7.62 (2H, dd, J=8.53, 5.52 Hz), 7.74 (1H, s), 7.87 (1H, s), 8.06 (1H, d, J=8.78 Hz), 8.13 (1H, s), 8.20-8.31 (1H, m), 8.61 (1H, d, J=2.26 Hz), 10.23 (1H, s).

Example 14

2-{[(4-Fluorophenyl)methyl]oxy}-4-(1-methyl-1H-pyrazol-4-yl)-5-(4-morpholinylmethyl)-N-4-pyridazinylbenzamide (E14)

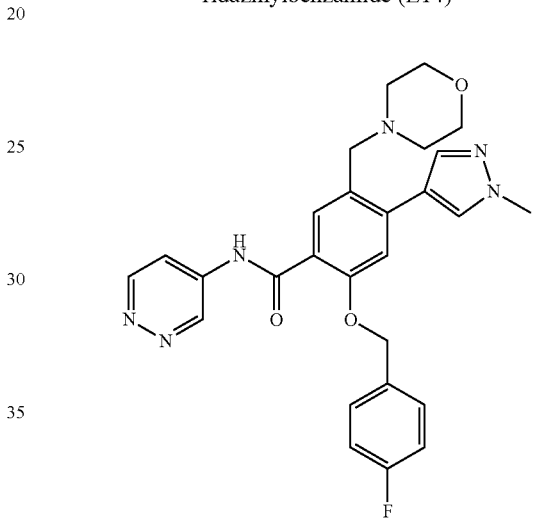

To a solution of methyl 2-{[(4-fluorophenyl)methyl]oxy}-4-(1-methyl-1H-pyrazol-4-yl)-5-(4-morpholinylmethyl)benzoate (may be prepared as described in Description 18; 144 mg, 0.33 mmol) in tetrahydrofuran (4 ml) was added lithium hydroxide (23.54 mg, 0.98 mmol) and water (1 ml). The mixture was stirred at room temperature for 18 hours then neutralised with 2M hydrochloric acid (0.79 ml, 1.59 mmol). The solvent was removed in vacuo and the residue redissolved in N,N-dimethylformamide (4 ml). Diisopropylethylamine (0.11 m, 0.66 mmol), 4-pyridazinamine (40.5 mg, 0.43 mmol), 1-hydroxy-7-azabenzotriazole (53.5 mg, 0.39 mmol) and EDC (94 mg, 0.49 mmol) were added and the solution was stirred for 3 hours. The solvent was removed in vacuo and the residue purified by MDAP to yield the title compound as a white solid. 57 mg.

MS (electrospray): m/z, [M+H]$^+$=503

$^1$H NMR (400 MHz, DMSO-d$_6$); 2.34-2.46 (4H, m), 3.43-3.49 (2H, m), 3.59 (4H, t, J=4.14 Hz), 3.92 (3H, s), 5.30 (2H, s), 7.21 (2H, t, J=8.91 Hz), 7.33 (1H, s), 7.60 (2H, dd, J=8.66, 5.65 Hz), 7.70 (1H, s), 7.87 (1H, s), 7.99 (1H, dd, J=5.77, 2.76 Hz), 8.14 (1H, s), 9.05 (1H, d, J=5.77 Hz), 9.16 (1H, d, J=1.76 Hz), 10.61 (1H, s).

Example 15

5-Bromo-2-{[(4-fluorophenyl)methyl]oxy}-4-(4-morpholinylmethyl)-N-3-pyridinylbenzamide (E15)

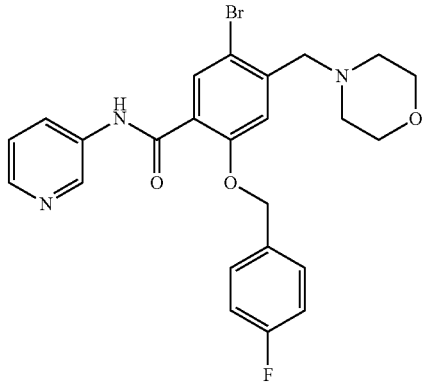 [SMILES: O=C(Nc1cccnc1)c1cc(Br)c(CN2CCOCC2)cc1OCc1ccc(F)cc1]

To a solution of 5-bromo-2-{[(4-fluorophenyl)methyl]oxy}-4-(4-morpholinylmethyl)benzoic acid (may be prepared as described in Description 20; 150 mg, 0.35 mmol) in N,N-dimethylformamide (4 ml) was added 3-aminopyridine (39.9 mg, 0.42 mmol), diisopropylethylamine (0.12 ml, 0.71 mmol), 1-hydroxy-7-azabenzotriazole (57.7 mg, 0.42 mmol) and EDC (102 mg, 0.53 mmol). The mixture was stirred for 18 hours, then the solvent removed in vacuo to give a solid. Purification by MDAP yielded the title compound as a solid. 95 mg.

MS (electrospray): m/z, [M+H]$^+$=500/502

Example 16

5-Bromo-2-{[(4-fluorophenyl)methyl]oxy}-N-(3-methyl-4-isoxazolyl)-4-(4-morpholinylmethyl)benzamide (E16)

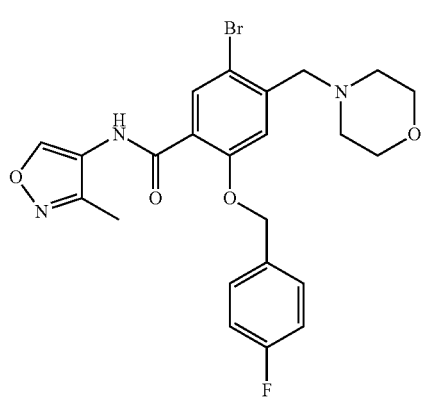 [SMILES: Cc1nocc1NC(=O)c1cc(Br)c(CN2CCOCC2)cc1OCc1ccc(F)cc1]

To a solution of 5-bromo-2-{[(4-fluorophenyl)methyl]oxy}-4-(4-morpholinylmethyl)benzoic acid (may be prepared as described in Description 20; 150 mg, 0.35 mmol) in N,N-dimethylformamide (4 ml) was added 3-methyl-4-isoxazolamine (41.6 mg, 0.42 mmol), diisopropylethylamine (0.12 ml, 0.71 mmol), 1-hydroxy-7-azabenzotriazole (57.7 mg, 0.42 mmol) and EDC (102 mg, 0.53 mmol). The mixture was stirred for 18 hours, then the solvent removed in vacuo to give a residue. The residue was purified by column chromatography (10% 7M NH$_3$ in methanol/dichloromethane) to yield the title compound as a solid. 178 mg.

MS (electrospray): m/z, [M+H]$^+$=504/506

Example 17

2-{[(4-Fluorophenyl)methyl]oxy}-5-(1-methyl-1H-pyrazol-4-yl)-4-(4-morpholinylmethyl)-N-3-pyridinylbenzamide (E17)

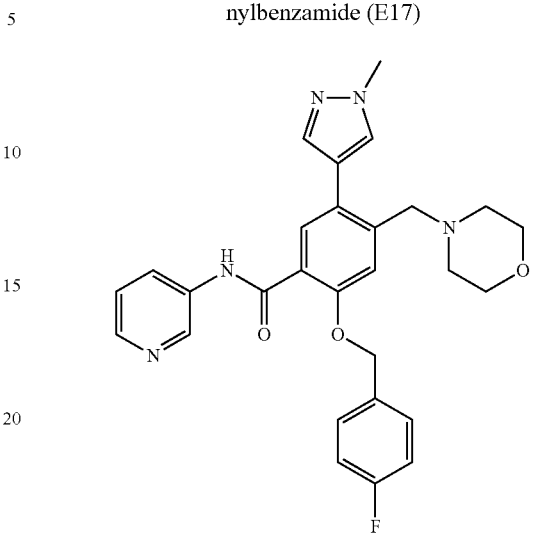

To a solution of 5-bromo-2-{[(4-fluorophenyl)methyl]oxy}-4-(4-morpholinylmethyl)-N-3-pyridinylbenzamide (may be prepared as described in Example 15; 95 mg, 0.19 mmol) in 1,2-dimethoxyethane (5 ml) was added 1-methyl-4-(4,4,5,5-tetramethyl-1,3,2-dioxaborolan-2-yl)-1H-pyrazole (47.4 mg, 0.23 mmol), Pd(Ph$_3$P)$_4$ (13.16 mg, 0.01 mmol) and sodium carbonate (0.38 ml, 0.38 mmol). The mixture was heated at 120° C. in the microwave for 35 minutes, cooled and the solvent removed in vacuo to give a solid. Purification by MDAP yielded the title compound as a colourless gum. 36 mg.

MS (electrospray): m/z, [M+H]$^+$=m/z 502

$^1$H NMR (400 MHz, DMSO-d$_6$): 1.68-1.85 (4H, m), 2.25-2.40 (4H, m), 3.60-3.67 (2H, m), 3.88 (3H, s), 5.30 (2H, s), 7.21 (2H, t, J=8.91 Hz), 7.29 (1H, s), 7.37 (1H, dd, J=8.28, 4.77 Hz), 7.58 (2H, dd, J=8.41, 5.65 Hz), 7.66 (2H, d, J=7.78 Hz), 7.94 (1H, s), 8.11 (1H, d, J=8.78 Hz), 8.28 (1H, dd, J=4.64, 1.13 Hz), 8.72 (1H, d, J=2.01 Hz), 10.34 (1H, s).

Example 18

2-{[(4-Fluorophenyl)methyl]oxy}-N-(3-methyl-4-isoxazolyl)-5-(1-methyl-1H-pyrazol-4-yl)-4-(4-morpholinylmethyl)benzamide (E18)

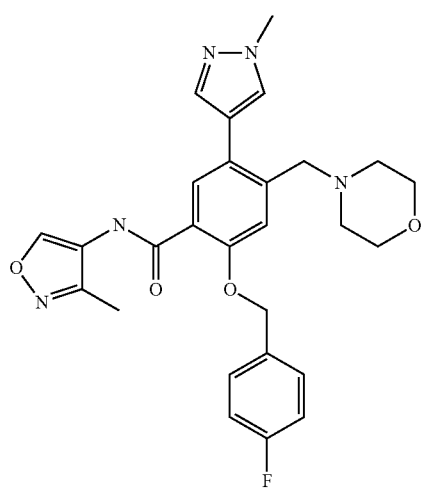 [SMILES: Cc1nocc1NC(=O)c1cc(-c2cnn(C)c2)c(CN2CCOCC2)cc1OCc1ccc(F)cc1]

To a solution of 5-bromo-2-{[(4-fluorophenyl)methyl]oxy}-N-(3-methyl-4-isoxazolyl)-4-(4-morpholinylmethyl)benzamide (may be prepared as described in Example 16; 89 mg, 0.18 mmol) in 1,2-dimethoxyethane (3 ml) was added 1-methyl-4-(4,4,5,5-tetramethyl-1,3,2-dioxaborolan-2-yl)-1H-pyrazole (40.4 mg, 0.19 mmol), sodium carbonate (0.35 ml, 0.35 mmol) and Pd(Ph$_3$P)$_4$ (12.23 mg, 10.59 μmol). The mixture was heated at 120° C. in a microwave for 35 minutes, the solvent removed in vacuo and the residue purified by MDAP to yield the title compound as a white solid. 12 mg.

MS (electrospray): m/z, [M+H]$^+$=506

$^1$H NMR (400 MHz, DMSO-d$_6$); 1.96 (3H, s), 2.29-2.42 (4H, m), 3.51-3.65 (6H, m), 3.88 (3H, s), 5.31 (2H, s), 7.18-7.45 (2H, m), 7.55-7.82 (4H, m), 7.91-8.03 (2H, m), 8.53 (1H, br. s.), 9.15 (1H, s), 9.82 (1H, br. s.).

Example 19

5-Bromo-2-{[(2,4-difluorophenyl)methyl]oxy}-4-(4-morpholinylmethyl)-N-3-pyridinylbenzamide (E19)

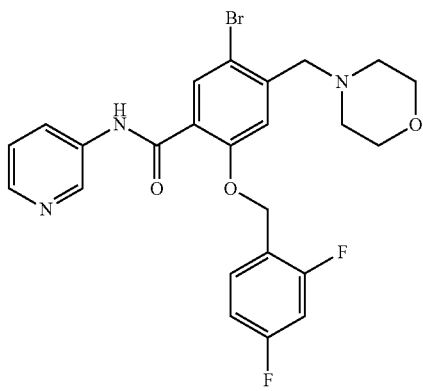 [SMILES: O=C(Nc1cccnc1)c1cc(Br)c(CN2CCOCC2)cc1OCc1ccc(F)cc1F]

To a solution of 5-bromo-2-{[(2,4-difluorophenyl)methyl]oxy}-4-(4-morpholinylmethyl)benzoic acid (may be prepared as described in Description 22; 150 mg, 0.34 mmol) in N,N-dimethylformamide (4 ml) was added 3-aminopyridine (38.3 mg, 0.41 mmol), diisopropylethylamine (0.12 ml, 0.68 mmol), 1-hydroxy-7-azabenzotriazole (55.4 mg, 0.41 mmol) and EDC (98 mg, 0.51 mmol). The mixture was stirred overnight and the solvent removed in vacuo to give a residue. Purification by column chromatography (SiO$_2$; 10% 7M NH$_3$ in methanol/dichloromethane) yielded the title compound as a solid. 162 mg.

MS (electrospray): m/z, [M+H]$^+$=518/520

$^1$H NMR (400 MHz, DMSO-d$_6$); 2.38-2.45 (4H, m), 3.17 (2H, d, J=5.27 Hz), 3.53-3.66 (4H, m), 5.28-5.39 (2H, m), 7.09 (1H, td, J=8.34, 2.38 Hz), 7.34-7.43 (2H, m), 7.56-7.66 (1H, m), 7.82 (1H, s), 7.89-8.01 (1H, m), 8.03-8.13 (1H, m), 8.29 (1H, dd, J=4.64, 1.38 Hz), 8.69 (1H, d, J=2.26 Hz), 10.33 (1H, s).

Example 20

2-{[(2,4-Difluorophenyl)methyl]oxy}-5-(1-methyl-1H-pyrazol-4-yl)-4-(4-morpholinylmethyl)-N-3-pyridinylbenzamide (E20)

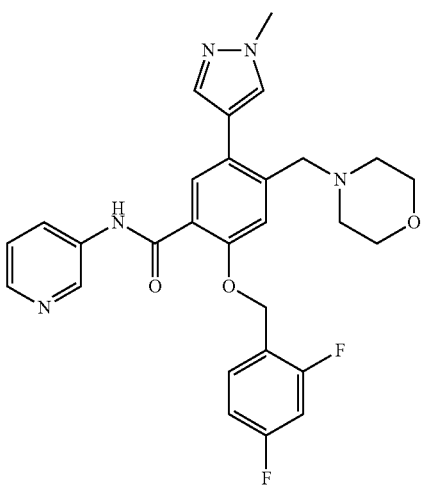 [SMILES: Cn1cc(-c2cc(C(=O)Nc3cccnc3)c(OCc3ccc(F)cc3F)cc2CN2CCOCC2)cn1]

To a solution of 5-bromo-2-{[(2,4-difluorophenyl)methyl]oxy}-4-(4-morpholinylmethyl)-N-3-pyridinylbenzamide (may be prepared as described in Example 9; 162 mg, 0.31 mmol) in 1,2-dimethoxyethane (5 ml) was added 1-methyl-4-(4,4,5,5-tetramethyl-1,3,2-dioxaborolan-2-yl)-1H-pyrazole (78 mg, 0.38 mmol), Pd(Ph$_3$P)$_4$ (21.67 mg, 0.02 mmol) and sodium carbonate (0.63 ml, 0.63 mmol). The mixture was heated at 120° C. in the microwave for 35 minutes, cooled and the solvent removed in vacuo. Purification by MDAP yielded the title compound as a brown solid. 75 mg.

MS (electrospray): m/z, [M+H]$^+$=520

$^1$H NMR (400 MHz, DMSO-d$_6$); 2.29-2.42 (4H, m), 3.53-3.65 (6H, m), 3.82-3.96 (3H, m), 5.34 (2H, s), 7.10 (1H, td, J=8.47, 2.13 Hz), 7.26-7.45 (2H, m), 7.59-7.73 (2H, m), 7.96 (1H, s), 8.05-8.18 (3H, m), 8.28 (1H, dd, J=4.64, 1.38 Hz), 8.71 (1H, d, J=2.26 Hz), 10.30 (1H, s).

Example 21

5-Bromo-2-{[(2,4-difluorophenyl)methyl]oxy}-N-(3-methyl-4-isoxazolyl)-4-(4-morpholinylmethyl)benzamide (E21)

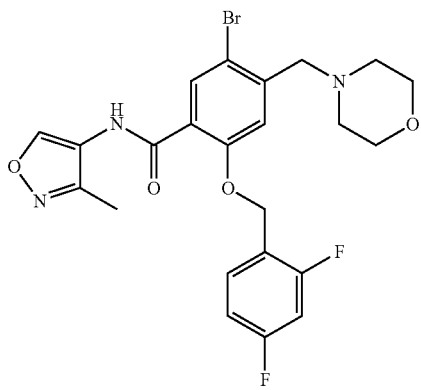 [SMILES: Cc1nocc1NC(=O)c1cc(Br)c(CN2CCOCC2)cc1OCc1ccc(F)cc1F]

To a solution of 5-bromo-2-{[(2,4-difluorophenyl)methyl]oxy}-4-(4-morpholinylmethyl)benzoic acid (may be prepared as described in Description 22; 150 mg, 0.34 mmol) in N,N-dimethylformamide (4 ml) was added diisopropylethylamine (0.12 ml, 0.68 mmol), 1-hydroxy-7-azabenzotriazole (55.4 mg, 0.41 mmol), 3-methyl-4-isoxazolamine hydrochloride (39.9 mg, 0.41 mmol) and EDC (98 mg, 0.51 mmol). The reaction was stirred for 18 hours. The solvent was removed in vacuo and the residue was purified by column chromatography (SiO$_2$; ethyl acetate) to yield the title compound as a solid. 162 mg.

LCMS: m/z 523 M+H.

Example 22

2-{[(2,4-Difluorophenyl)methyl]oxy}-N-(3-methyl-4-isoxazolyl)-5-(1-methyl-1H-pyrazol-4-yl)-4-(4-morpholinylmethyl)benzamide (E22)

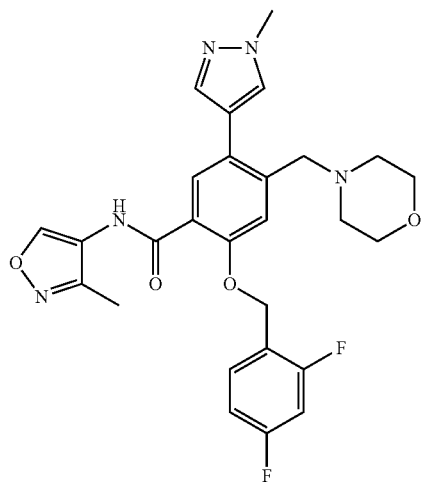 [SMILES: Cc1nocc1NC(=O)c1cc(-c2cnn(C)c2)c(CN2CCOCC2)cc1OCc1ccc(F)cc1F]

To a solution of 5-bromo-2-{[(4-fluorophenyl)methyl]oxy}-N-(3-methyl-4-isoxazolyl)-4-(4-morpholinylmethyl)benzamide (may be prepared as described in Example 21; 89 mg, 0.18 mmol) in 1,2-dimethoxyethane (3 ml) was added 1-methyl-4-(4,4,5,5-tetramethyl-1,3,2-dioxaborolan-2-yl)-1H-pyrazole (40.4 mg, 0.19 mmol), sodium carbonate (0.35 ml, 0.35 mmol) and Pd(Ph$_3$P)$_4$ (12.23 mg, 10.59 µmol). The mixture was heated at 120° C. in a microwave for 35 minutes, the solvent removed in vacuo and the residue purified by MDAP to yield the title compound as a white solid. 12 mg.

MS (electrospray): m/z, [M+H]$^+$=524

$^1$H NMR (400 MHz, DMSO-d$_6$); 2.00 (3H, s), 2.31-2.43 (4H, m), 3.46-3.68 (6H, m), 3.88 (3H, s), 5.36 (2H, br. s.), 7.05-7.23 (1H, m), 7.39 (2H, s), 7.54-7.82 (3H, m), 7.95 (1H, s), 9.14 (1H, s), 9.78 (1H, s).

Example 23

5-(1-Methyl-1H-pyrazol-4-yl)-4-(4-morpholinylcarbonyl)-2-[(phenylmethyl)oxy]-N-3-pyridinylbenzamide (E23)

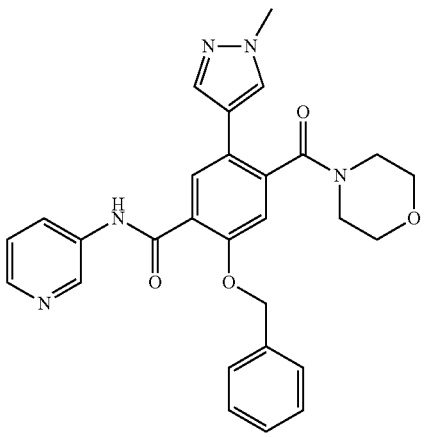 [SMILES: Cn1cc(-c2cc(C(=O)Nc3cccnc3)c(OCc3ccccc3)cc2C(=O)N2CCOCC2)cn1]

To a solution of 5-(1-methyl-1H-pyrazol-4-yl)-4-(4-morpholinylcarbonyl)-2-[(phenylmethyl)oxy]benzoic acid (may be prepared as described in Description 26; 150 mg, 0.36 mmol) in N,N-dimethylformamide (3 ml) was added diisopropylethylamine (0.12 ml, 0.71 mmol), 3-aminopyridine (40.2 mg, 0.43 mmol), 1-hydroxy-7-azabenzotriazole (58.1 mg, 0.43 mmol) and EDC (116 mg, 0.61 mmol). The reaction was stirred for 18 hours and then the solvent was removed in vacuo. The residue was purified by MDAP to yield the title compound as a yellow gum. 111 mg.

MS (electrospray): m/z, [M+H]$^+$=498

$^1$H NMR (400 MHz, DMSO-d$_6$); 2.79-3.11 (3H, m), 3.44-3.74 (5H, m), 3.79-3.96 (2H, m), 5.15-5.36 (2H, m), 7.20 (1H, s), 7.29-7.42 (3H, m), 7.45-7.63 (3H, m), 7.76 (1H, s), 7.85 (1H, s), 8.02-8.19 (2H, m), 8.29 (1H, dd, J=4.64, 1.38 Hz), 8.73 (1H, d, J=2.26 Hz), 10.44 (1H, s).

Example 24

5-(1-Methyl-1H-pyrazol-4-yl)-4-(4-morpholinylcarbonyl)-2-[(phenylmethyl)oxy]-N-4-pyridazinylbenzamide (E24)

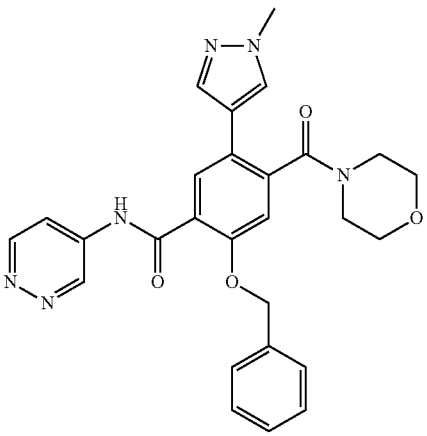 [SMILES: Cn1cc(-c2cc(C(=O)Nc3ccnnc3)c(OCc3ccccc3)cc2C(=O)N2CCOCC2)cn1]

To a solution of 5-(1-methyl-1H-pyrazol-4-yl)-4-(4-morpholinylcarbonyl)-2-[(phenylmethyl)oxy]benzoic acid (may be prepared as described in Description 26; 150 mg, 0.36 mmol) in N,N-dimethylformamide (3 ml) was added diisopropylethylamine (0.12 ml, 0.71 mmol), 4-aminopyridazine (33.8 mg, 0.36 mmol), 1-hydroxy-7-azabenzotriazole (58.1 mg, 0.43 mmol) and EDC (116 mg, 0.61 mmol). The reaction was stirred for 18 hours and then the solvent was removed in vacuo. The residue was purified by MDAP to yield the title compound as a yellow gum. 117 mg.

MS (electrospray): m/z, [M+H]$^+$=499

$^1$H NMR (400 MHz, DMSO-d$_6$); 2.74-3.11 (3H, m), 3.41-3.76 (5H, m), 3.81-3.95 (3H, m), 5.15-5.38 (2H, m), 7.22 (1H, s), 7.26-7.41 (3H, m), 7.48 (2H, d, J=6.78 Hz), 7.59 (1H, s), 7.75 (1H, s), 7.85 (1H, s), 8.03 (1H, dd, J=5.90, 2.64 Hz), 9.07 (1H, d, J=5.77 Hz), 9.27 (1H, d, J=1.76 Hz), 10.87 (1H, s).

Example 25

N-(3-Methyl-4-isoxazolyl)-5-(1-methyl-1H-pyrazol-4-yl)-4-(4-morpholinylcarbonyl)-2-[(phenylmethyl)oxy]benzamide (E25)

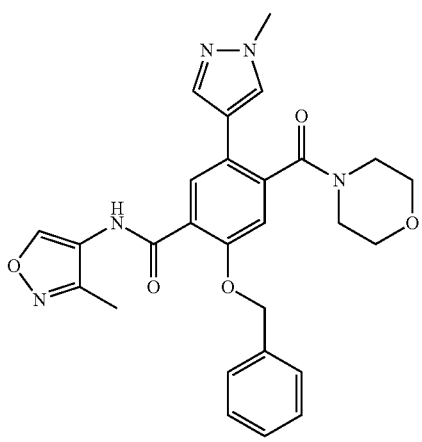 [SMILES: Cc1nocc1NC(=O)c1cc(-c2cnn(C)c2)c(C(=O)N2CCOCC2)cc1OCc1ccccc1]

To a solution of 5-(1-methyl-1H-pyrazol-4-yl)-4-(4-morpholinylcarbonyl)-2-[(phenylmethyl)oxy]benzoic acid (may be prepared as described in Description 26; 44 mg, 0.10 mmol) in N,N-dimethylformamide (5 ml) was added diisopropylethylamine (0.04 ml, 0.21 mmol), 3-methyl-4-isoxazolamine (20.48 mg, 0.21 mmol), 1-hydroxy-7-azabenzotriazole (21.32 mg, 0.16 mmol) and EDC (34.0 mg, 0.18 mmol). The reaction was stirred for 18 hours and then the solvent was removed in vacuo. The residue was purified by MDAP to yield the title compound as a white solid. 43 mg.

MS (electrospray): m/z, [M+H]$^+$=502

$^1$H NMR (400 MHz, DMSO-d$_6$); 1.92 (s, 3H), 2.80-3.13 (m, 3H), 3.35-3.72 (m, 5H), 3.92 (s, 3H), 5.13-5.41 (m, 2H), 7.24 (s, 1H), 7.33-7.45 (m, 3H), 7.47-7.62 (m, 3H), 7.85 (d, J=3.01 Hz, 2H), 9.16 (s, 1H), 9.90 (s, 1H).

Example 26

2-{[(4-Fluorophenyl)methyl]oxy}-5-(1-methyl-1H-pyrazol-4-yl)-4-(4-morpholinylcarbonyl)-N-3-pyridinylbenzamide (E26)

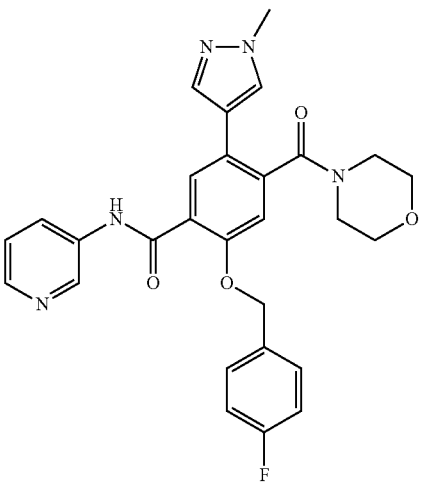 [SMILES: Cn1cc(-c2cc(C(=O)Nc3cccnc3)c(OCc3ccc(F)cc3)cc2C(=O)N2CCOCC2)cn1]

To a solution of 2-{[(4-fluorophenyl)methyl]oxy}-5-(1-methyl-1H-pyrazol-4-yl)-4-(4-morpholinylcarbonyl)benzoic acid (may be prepared as described in Description 29; 12 mg, 0.02 mmol) in N,N-dimethylformamide (4 ml), was added diisopropylethylamine (4.15 μL, 0.02 mmol), 3-aminopyridine (2.23 mg, 0.02 mmol) and HATU (9.03 mg, 0.02 mmol). The reaction stirred for 18 hours, then the solvent was removed in vacuo. The residue was purified by MDAP to yield the title compound as a gum. 4.8 mg.

MS (electrospray): m/z, [M+H]$^+$=516

$^1$H NMR (400 MHz, MeOD); 2.84-2.99 (2H, m), 3.05-3.19 (1H, m), 3.38-3.84 (5H, m), 3.94 (3H, s), 5.30 (2H, s), 7.07-7.20 (2H, m), 7.25 (1H, s), 7.39 (1H, dd, J=8.41, 4.89 Hz), 7.53-7.62 (3H, m), 7.80 (1H, s), 8.02 (1H, s), 8.07 (1H, dt, J=8.47, 1.91 Hz), 8.26 (1H, d, J=3.76 Hz), 8.54 (1H, d, J=2.26 Hz).

Example 27

2-{[(4-Fluorophenyl)methyl]oxy}-5-(1-methyl-1H-pyrazol-4-yl)-4-(4-morpholinylcarbonyl)-N-4-pyridazinylbenzamide (E27)

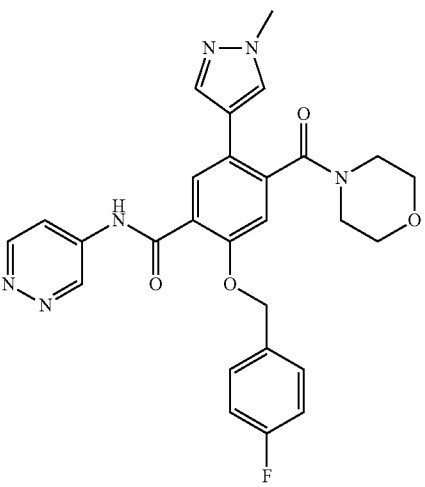 [SMILES: Cn1cc(-c2cc(C(=O)Nc3ccnnc3)c(OCc3ccc(F)cc3)cc2C(=O)N2CCOCC2)cn1]

To a solution of 2-{[(4-fluorophenyl)methyl]oxy}-5-(1-methyl-1H-pyrazol-4-yl)-4-(4-morpholinylcarbonyl)benzoic acid (may be prepared as described in Description 29; 95 mg, 0.22 mmol) in N,N-dimethylformamide (3 ml) was added diisopropylethylamine (0.08 ml, 0.43 mmol), 4-pyridazinamine (24.67 mg, 0.26 mmol), 1-hydroxy-7-azabenzotriazole (35.3 mg, 0.26 mmol) and EDC (62.2 mg, 0.32 mmol). The mixture was stirred for 2 hours, the solvent removed in vacuo and the residue was purified by MDAP to yield the title compound as a white solid. 50 mg.

MS (electrospray): m/z, [M+H]$^+$=517

$^1$H NMR (400 MHz, DMSO-d$_6$); 2.73-3.11 (3H, m), 3.46-3.76 (5H, m), 3.90 (3H, s), 5.14-5.35 (2H, m), 7.11-7.28 (3H, m), 7.47-7.64 (3H, m), 7.75 (1H, s), 7.85 (1H, s), 8.02 (1H, dd, J=5.90, 2.64 Hz), 9.07 (1H, d, J=5.77 Hz), 9.28 (1H, d, J=2.01 Hz), 10.84 (1H, s).

Example 28

2-{[(4-Fluorophenyl)methyl]oxy}-4-(1-methyl-1H-pyrazol-4-yl)-5-(4-morpholinylcarbonyl)-N-3-pyridinylbenzamide (E28)

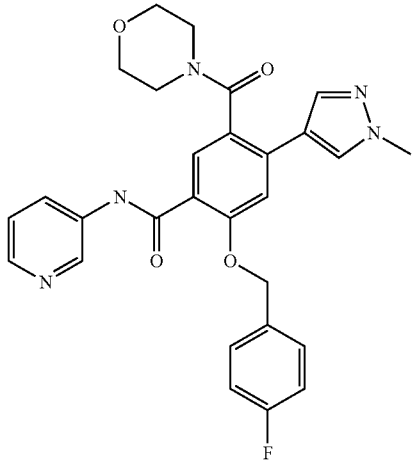 [SMILES: Cn1cc(-c2cc(OCc3ccc(F)cc3)c(C(=O)Nc3cccnc3)cc2C(=O)N2CCOCC2)cn1]

To a solution of (4-fluorophenyl) methyl 2-{[(4-fluorophenyl)methyl]oxy}-4-(1-methyl-1H-pyrazol-4-yl)-5-(4-morpholinylcarbonyl)benzoate (may be prepared as described in Description 32; 191 mg, 0.35 mmol) in tetrahydrofuran (6 ml) was added lithium hydroxide (60 mg, 2.51 mmol) and water (1.5 ml). The mixture was stirred for 3 hours then neutralised with 2M hydrochloric acid (1.26 ml, 2.51 mmol). The solvent was removed in vacuo and the residue was redissolved in N,N-dimethylformamide (6 ml), and diisopropylethylamine (0.12 ml, 0.70 mmol), 3-aminopyridine (39.4 mg, 0.42 mmol), 1-hydroxy-7-azabenzotriazole (57.0 mg, 0.42 mmol) and EDC (100 mg, 0.52 mmol) were added. The reaction stirred for 18 hours, then the solvent was removed in vacuo and the residue purified by MDAP to yield the title compound as a white solid MS (electrospray): m/z, [M+H]$^+$=516

$^1$H NMR (400 MHz, DMSO-d$_6$); 2.75-3.16 (3H, m), 3.37-3.71 (5H, m), 3.82-3.97 (3H, m), 5.35 (2H, s), 7.23 (2H, t, J=8.78 Hz), 7.31-7.49 (2H, m), 7.53-7.67 (3H, m), 7.74 (1H, s), 7.98 (1H, s), 8.07 (1H, d, J=8.53 Hz), 8.28 (1H, dd, J=4.64, 1.38 Hz), 8.63 (1H, d, J=2.51 Hz), 10.29 (1H, s).

Example 29

2-{[(4-Fluorophenyl)methyl]oxy}-4-(1-methyl-1H-pyrazol-4-yl)-5-(4-morpholinylcarbonyl)-N-4-pyridazinylbenzamide (E29)

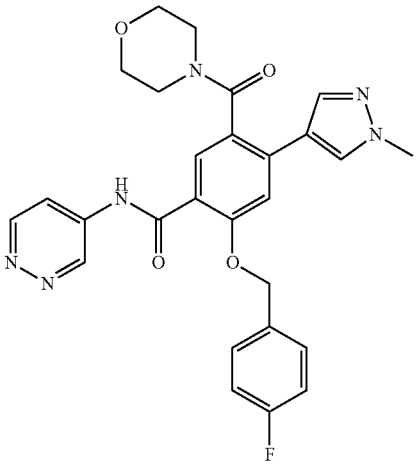 [SMILES: Cn1cc(-c2cc(OCc3ccc(F)cc3)c(C(=O)Nc3ccnnc3)cc2C(=O)N2CCOCC2)cn1]

To a solution of (4-fluorophenyl) methyl 2-{[(4-fluorophenyl)methyl]oxy}-4-(1-methyl-1H-pyrazol-4-yl)-5-(4-morpholinylcarbonyl)benzoate (may be prepared as described in Description 32; 191 mg, 0.35 mmol) in tetrahydrofuran (6 ml) was added lithium hydroxide (60 mg, 2.51 mmol) and water (1.5 ml). The mixture was stirred for 3 hours then quenched with 2M hydrochloric acid (1.26 ml, 2.51 mmol). The solvent was removed in vacuo and the residue was redissolved in N,N-dimethylformamide (6 ml) and diisopropylethylamine (0.12 ml, 0.70 mmol), 4-pyridazinamine (39.8 mg, 0.42 mmol), 1-hydroxy-7-azabenzotriazole (57.0 mg, 0.42 mmol) and EDC (100 mg, 0.52 mmol) were added. The reaction was stirred for 18 hours then the solvent was removed in vacuo and the residue purified by MDAP to yield the title compound as a white solid. 64 mg.

MS (electrospray): m/z, [M+H]$^+$=517

$^1$H NMR (400 MHz, DMSO-d$_6$); 2.74-3.13 (3H, m), 3.35-3.75 (5H, m), 3.86-3.96 (3H, m), 5.33 (2H, s), 7.15-7.29 (2H, m), 7.43 (1H, s), 7.50-7.66 (3H, m), 7.74 (1H, s), 7.94-8.07 (2H, m), 8.95-9.10 (1H, m), 9.20 (1H, d, J=1.76 Hz), 10.69 (1H, s).

Example 30

4-Bromo-5-(4-morpholinylmethyl)-2-[(phenylmethyl)oxy]-N-3-pyridinylbenzamide (E30)

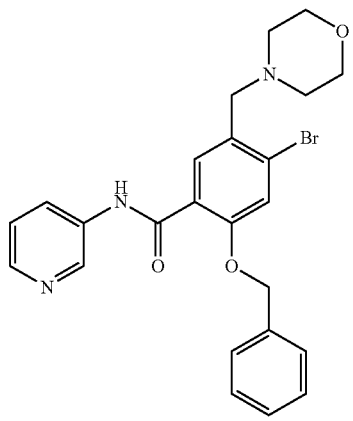 [SMILES: O=C(Nc1cccnc1)c1cc(CN2CCOCC2)c(Br)cc1OCc1ccccc1]

To a suspension of 4-bromo-5-(4-morpholinylmethyl)-2-[(phenylmethyl)oxy]benzoic acid (may be prepared as described in Description 35; 100 mg, 0.25 mmol) in N,N-dimethylformamide (5 ml) was added diisopropylethylamine (0.09 ml, 0.49 mmol), HOBT (45.2 mg, 0.30 mmol), 3-aminopyridine (30.1 mg, 0.32 mmol) and EDC (94 mg, 0.49 mmol). The mixture was heated at 50° C. for 5 hours to allow dissolution. The solvent was removed in vacuo and purified by MDAP to yield the title compound as a white solid. 67 mg.

MS (electrospray): m/z, [M+H]$^+$=481/483

$^1$H NMR (DMSO-$d_6$): 2.36-2.47 (4H, m), 3.51-3.64 (6H, m), 5.28 (2H, s), 7.30-7.45 (4H, m), 7.49-7.60 (3H, m), 7.75 (1H, s), 8.06 (1H, dd, J=8.55, 1.75 Hz), 8.28 (1H, dd, J=4.71, 1.43 Hz), 8.65 (1H, d, J=2.41 Hz), 10.31 (1H, s)

Example 31

5-(1-Methyl-1H-pyrazol-4-yl)-2-[(phenylmethyl)oxy]-4-(1-piperidinylcarbonyl)-N-3-pyridinylbenzamide (E31)

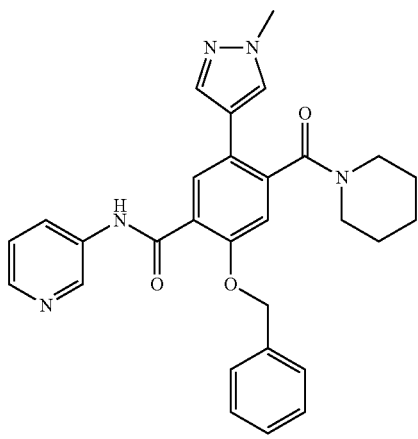 [SMILES: Cn1cc(-c2cc(C(=O)Nc3cccnc3)c(OCc3ccccc3)cc2C(=O)N2CCCCC2)cn1]

To a solution of 5-(1-methyl-1H-pyrazol-4-yl)-2-[(phenylmethyl)oxy]-4-(1-piperidinylcarbonyl)benzoic acid (may be prepared as described in Description 38; 80 mg, 0.19 mmol) in N,N-dimethylformamide (5 ml) was added diisopropylethylamine (0.13 ml, 0.76 mmol), 3-aminopyridine (32.3 mg, 0.34 mmol), 1-hydroxy-7-azabenzotriazole (46.7 mg, 0.34 mmol) and EDC (91 mg, 0.48 mmol). The solution was stirred for 3 hours. The solvent was removed in vacuo and the residue purified by MDAP to give the title compound as a white solid. 33 mg.

MS (electrospray): m/z [M+H]$^+$496

$^1$H NMR (DMSO-$d_6$): 0.78-0.99 (1H, m), 1.15-1.33 (1H, m), 1.34-1.61 (4H, m), 2.82-3.09 (2H, m), 3.52-3.70 (2H, m), 3.86 (3H, s), 5.20-5.36 (2H, m), 7.14 (1H, s), 7.29-7.42 (4H, m), 7.51 (2H, d, J=6.78 Hz), 7.56-7.63 (1H, m), 7.76 (1H, s), 7.84 (1H, s), 8.12 (1H, d, J=8.53 Hz), 8.29 (1H, d, J=3.76 Hz), 8.74 (1H, d, J=2.01 Hz), 10.43 (1H, s).

Example 32

N,N-Dimethyl-2-(1-methyl-1H-pyrazol-4-yl)-5-[(phenylmethyl)oxy]-N'-3-pyridinyl-1,4-benzenedicarboxamide (E32)

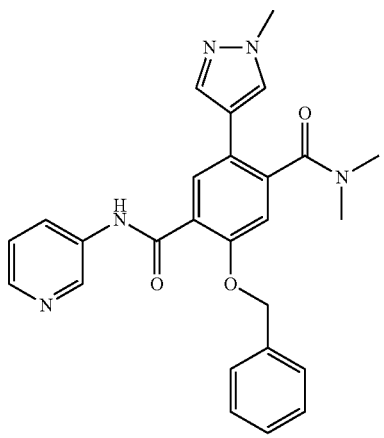 [SMILES: CN(C)C(=O)c1cc(OCc2ccccc2)c(C(=O)Nc2cccnc2)cc1-c1cnn(C)c1]

To a solution of 4-[(dimethylamino)carbonyl]-5-(1-methyl-1H-pyrazol-4-yl)-2-[(phenylmethyl)oxy]benzoic acid (may be prepared as described in Description 41; 152 mg, 0.41 mmol) in N,N-dimethylformamide (5 ml) was added diisopropylethylamine (0.15 ml, 0.83 mmol), 3-aminopyridine (50.8 mg, 0.54 mmol), 1-hydroxy-7-azabenzotriazole (73.5 mg, 0.54 mmol) and EDC (159 mg, 0.83 mmol). The solution was stirred for 3 hours. The solvent was removed in vacuo and the residue purified by MDAP to give the title compound as a white solid. 112 mg.

MS (electrospray): m/z [M+H]$^+$456

$^1$H NMR (DMSO-$d_6$): 2.62 (3H, s), 2.98 (3H, s), 3.86 (3H, s), 5.27 (2H, d, J=5.52 Hz), 7.16 (1H, s), 7.25-7.44 (4H, m), 7.47-7.61 (3H, m), 7.78 (1H, s), 7.84 (1H, s), 8.11 (1H, d, J=8.53 Hz), 8.29 (1H, d, J=3.51 Hz), 8.73 (1H, d, J=2.26 Hz), 10.43 (1H, s).

Example 33

2-(Benzyloxy)-4-(morpholinomethyl)-N-(pyridin-3-yl)-5-(trifluoromethyl)benzamide (E33)

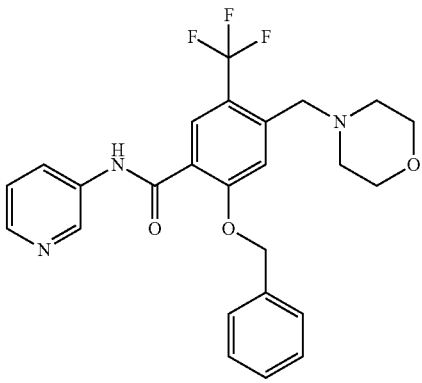 [SMILES: O=C(Nc1cccnc1)c1cc(C(F)(F)F)c(CN2CCOCC2)cc1OCc1ccccc1]

To a solution of 4-(4-morpholinylmethyl)-2-[(phenylmethyl)oxy]-5-(trifluoromethyl)benzoic acid (may be prepared as described in Description 50; 120 mg, 0.30 mmol) in N,N-dimethylformamide (5 ml) was added diisopropylethylamine (0.11 ml, 0.61 mmol), 3-aminopyridine (42.8 mg, 0.46 mmol), 1-hydroxy-7-azabenzotriazole (53.7 mg, 0.40 mmol) and EDC (116 mg, 0.61 mmol). The solution was stirred for 2 hours, then the solvent was removed in vacuo. The yellow residue was purified by MDAP to give the title compound as a white solid. 106 mg.

MS (electrospray): m/z [M+H]$^+$ 472

$^1$H NMR (DMSO-d$_6$): 2.29-2.40 (4H, m), 3.51-3.59 (4H, m), 3.65 (2H, s), 5.39 (2H, s), 7.22-7.45 (4H, m), 7.53 (2H, d, J=7.03 Hz), 7.61 (1H, s), 7.95 (1H, s), 8.07-8.19 (1H, m), 8.30 (1H, dd, J=4.77, 1.51 Hz), 8.72 (1H, d, J=2.51 Hz), 10.44 (1H, s).

Example 34

4-(4-Morpholinylmethyl)-2-[(phenylmethyl)oxy]-N-4-pyridazinyl-5-(trifluoromethyl)benzamide (E34)

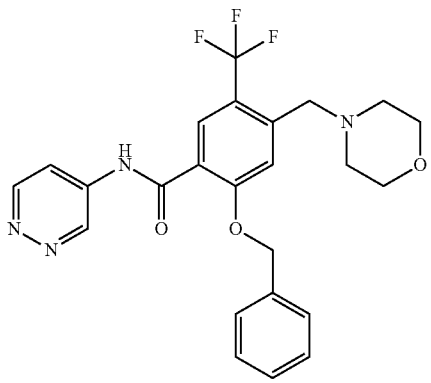 [SMILES: O=C(Nc1ccnnc1)c1cc(C(F)(F)F)c(CN2CCOCC2)cc1OCc1ccccc1]

To a solution of 4-(4-morpholinylmethyl)-2-[(phenylmethyl)oxy]-5-(trifluoromethyl)benzoic acid (may be prepared as described in Description 50; 120 mg, 0.30 mmol) in N,N-dimethylformamide (5 ml) was added diisopropylethylamine (0.11 ml, 0.61 mmol), 4-pyridazinamine (43.3 mg, 0.46 mmol), 1-hydroxy-7-azabenzotriazole (53.7 mg, 0.40 mmol) and EDC (116 mg, 0.61 mmol). The reaction was stirred for 3 hours and the solvent was removed in vacuo to give yellow oil. Purification by MDAP gave the title compound as a white solid. 72 mg.

MS (electrospray): m/z [M+H]$^+$ 473

$^1$H NMR (DMSO-d$_6$): 2.27-2.42 (4H, m), 3.51-3.61 (4H, m), 3.63 (2H, s), 5.38 (2H, s), 7.26-7.42 (3H, m), 7.51 (2H, d, J=6.78 Hz), 7.62 (1H, s), 7.94 (1H, s), 8.03 (1H, dd, J=5.90, 2.64 Hz), 9.08 (1H, d, J=5.77 Hz), 9.28 (1H, d, J=2.01 Hz), 10.85 (1H, s).

Example 35

2-[(Phenylmethyl)oxy]-4-(1-piperidinylmethyl)-N-3-pyridinyl-5-(trifluoromethyl)benzamide (E35)

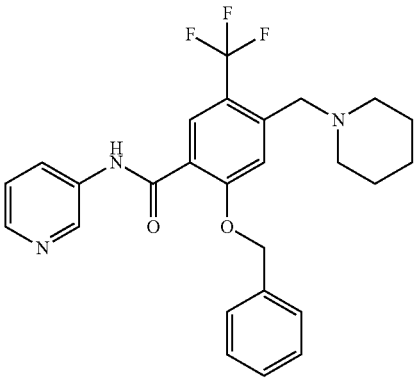 [SMILES: O=C(Nc1cccnc1)c1cc(C(F)(F)F)c(CN2CCCCC2)cc1OCc1ccccc1]

To a solution of 2-[(phenylmethyl)oxy]-4-(1-piperidinylmethyl)-5-(trifluoromethyl)benzoic acid (may be prepared as described in Description 53; 112 mg, 0.29 mmol) in N,N-dimethylformamide (5 ml) was added diisopropylethylamine (0.10 ml, 0.57 mmol), 3-aminopyridine (40.2 mg, 0.43 mmol), 1-hydroxy-7-azabenzotriazole (50.4 mg, 0.37 mmol) and EDC (109 mg, 0.57 mmol). The reaction was stirred for 3 hours, then the solvent removed in vacuo to give a yellow oil. Purification by MDAP gave the title compound as a white solid. 69 mg.

MS (electrospray): m/z [M+H]$^+$ 470

$^1$H NMR (DMSO-d$_6$): 1.33-1.54 (6H, m), 2.25-2.39 (4H, m), 3.58 (2H, s), 5.36 (2H, s), 7.28-7.44 (4H, m), 7.54 (2H, d, J=7.03 Hz), 7.64 (1H, s), 7.94 (1H, s), 8.10 (1H, d, J=8.53 Hz), 8.30 (1H, d, J=3.76 Hz), 8.71 (1H, d, J=2.01 Hz), 10.41 (1H, s).

Example 36

2-[(Phenylmethyl)oxy]-4-(1-piperidinylmethyl)-N-4-pyridazinyl-5-(trifluoromethyl)benzamide (E36)

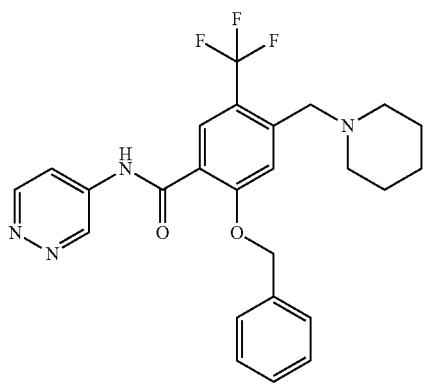 [SMILES: O=C(Nc1ccnnc1)c1cc(C(F)(F)F)c(CN2CCCCC2)cc1OCc1ccccc1]

To a solution of 2-[(phenylmethyl)oxy]-4-(1-piperidinylmethyl)-5-(trifluoromethyl)benzoic acid (may be prepared as described in Description 53; 112 mg, 0.29 mmol) in N,N-dimethylformamide (5 ml) was added diisopropylethylamine (0.10 ml, 0.57 mmol), 4-pyridazinamine (40.6 mg, 0.43 mmol), 1-hydroxy-7-azabenzotriazole (50.4 mg, 0.37 mmol) and EDC (109 mg, 0.57 mmol). The reaction was stirred for 18 hours, then the solvent removed in vacuo to give a yellow oil. Purification by MDAP gave the title compound as a white solid. 66 mg.

MS (electrospray): m/z [M+H]$^+$471

$^1$H NMR (DMSO-d$_6$): 1.29-1.60 (6H, m), 2.23-2.41 (5H, m), 3.50-3.70 (2H, m), 5.36 (2H, s), 7.18-7.44 (3H, m), 7.46-7.57 (2H, m), 7.64 (1H, s), 7.93 (1H, s), 8.02 (1H, dd, J=5.90, 2.64 Hz), 9.08 (1H, d, J=5.77 Hz), 9.27 (1H, d, J=2.51 Hz), 10.84 (1H, s).

Example 37

4-(4-Morpholinylcarbonyl)-2-[(phenylmethyl)oxy]-N-3-pyridinyl-5-(trifluoromethyl)benzamide (E37)

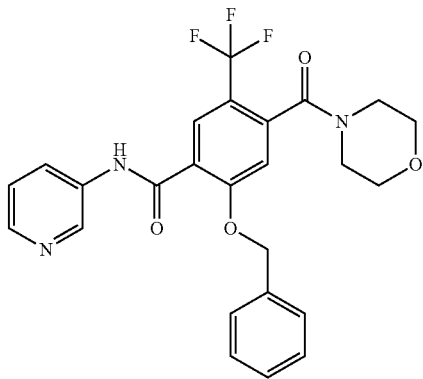 [SMILES: O=C(Nc1cccnc1)c1cc(C(F)(F)F)c(C(=O)N2CCOCC2)cc1OCc1ccccc1]

To a solution of phenylmethyl 4-(4-morpholinylcarbonyl)-2-[(phenylmethyl)oxy]-5-(trifluoromethyl)benzoate (may be prepared as described in Description 56; 64 mg, 0.13 mmol) in tetrahydrofuran (3 ml) was added lithium hydroxide (9.21 mg, 0.38 mmol) and water (0.75 ml). The solution was heated at 45° C. for one hour, cooled and 2M hydrochloric acid (0.19 ml, 0.38 mmol) was added. The solvent was removed in vacuo and the residue redissolved in N,N-dimethylformamide (4 ml). Diisopropylethylamine (0.06 ml, 0.32 mmol), 3-aminopyridine (18.09 mg, 0.19 mmol), 1-hydroxy-7-azabenzotriazole (22.67 mg, 0.17 mmol) and EDC (44.2 mg, 0.23 mmol) were added and the mixture was stirred for 18 hours. Ethyl acetate (20 ml) and water (10 ml) were added and the organic layer washed further with water (2×5 ml), dried (MgSO$_4$) and the solvent removed in vacuo to give a gum. Purification by MDAP gave the title compound as a white solid. 38 mg.

MS (electrospray): m/z [M+H]$^+$486

$^1$H NMR (DMSO-d$_6$): 2.99-3.19 (2H, m), 3.37-3.77 (6H, m), 5.37 (2H, d, J=3.76 Hz), 7.26-7.47 (5H, m), 7.51 (2H, d, J=6.78 Hz), 8.00 (1H, s), 8.10 (1H, d, J=8.53 Hz), 8.31 (1H, d, J=4.77 Hz), 8.72 (1H, d, J=2.26 Hz), 10.51 (1H, s).

Example 38

4-(4-Morpholinylcarbonyl)-2-[(phenylmethyl)oxy]-N-4-pyridazinyl-5-(trifluoromethyl)benzamide (E38)

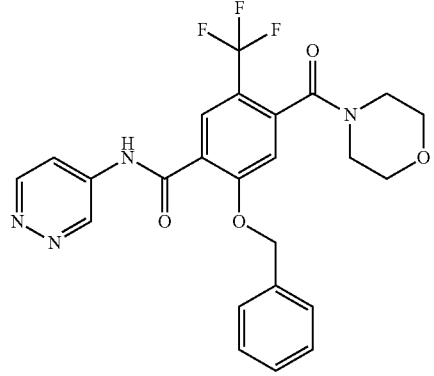 [SMILES: O=C(Nc1ccnnc1)c1cc(C(F)(F)F)c(C(=O)N2CCOCC2)cc1OCc1ccccc1]

To a solution of phenylmethyl 4-(4-morpholinylcarbonyl)-2-[(phenylmethyl)oxy]-5-(trifluoromethyl)benzoate (may be prepared as described in Description 56; 80 mg, 0.16 mmol) in tetrahydrofuran (4 ml) was added lithium hydroxide (11.51 mg, 0.48 mmol) and water (1 ml). The mixture was heated at 45° C. for one hour, cooled and 2M hydrochloric acid (0.24 ml, 0.48 mmol) was added. The solvent was removed in vacuo to give a residue. The residue was redissolved in N,N-dimethylformamide (4 ml) and diisopropylethylamine (0.06 ml, 0.32 mmol), 4-pyridazinamine (19.80 mg, 0.21 mmol), 1-hydroxy-7-azabenzotriazole (28.3 mg, 0.21 mmol) and EDC (55.3 mg, 0.29 mmol) were added. The mixture was stirred for 72 hours. Ethyl acetate (10 ml) and water (10 ml) were added and the organic layer separated and washed further with water (10 ml), dried (MgSO$_4$) and the solvent removed in vacuo to give a gum. Purification by MDAP gave the title compound as a white solid. 30 mg.

MS (electrospray): m/z [M+H]$^+$487

$^1$H NMR (DMSO-d$_6$): 2.96-3.16 (2H, m), 3.37-3.80 (6H, m), 5.25-5.44 (2H, m), 7.27-7.41 (3H, m), 7.41-7.51 (3H, m), 7.93-8.08 (2H, m), 9.09 (1H, d, J=6.02 Hz), 9.27 (1H, d, J=1.76 Hz), 10.95 (1H, s).

Example 39

2-[(Phenylmethyl)oxy]-4-(1-piperidinylcarbonyl)-N-3-pyridinyl-5-(trifluoromethyl)benzamide (E39)

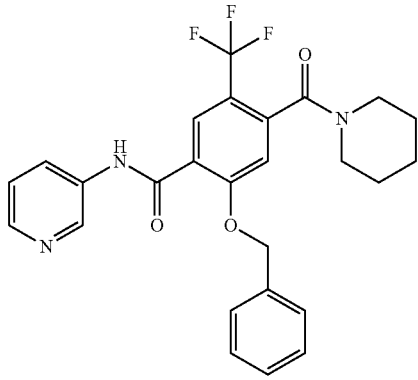 [SMILES: O=C(Nc1cccnc1)c1cc(C(F)(F)F)c(C(=O)N2CCCCC2)cc1OCc1ccccc1]

2-[(Phenylmethyl)oxy]-4-(1-piperidinylcarbonyl)-5-(trifluoromethyl)benzoic acid (may be prepared as described in Description 58; 69 mg) was dissolved in N,N-dimethylformamide (4 ml). Diisopropylethylamine (0.06 ml, 0.34 mmol) and HATU (130 mg, 0.34 mmol) were added, the solution was stirred for 5 minutes then 3-aminopyridine (32.2 mg, 0.34 mmol) was added. The solution was stirred for 90 minutes, the solvent was removed in vacuo and the residue purified by MDAP to give the title compound as a white solid. 29 mg.

MS (electrospray): m/z [M+H]$^+$484

$^1$H NMR (DMSO-d$_6$): 1.23-1.72 (6H, m), 2.96-3.10 (2H, m), 3.48-3.73 (2H, m), 5.37 (2H, s), 7.28-7.43 (5H, m), 7.51 (2H, d, J=6.78 Hz), 7.98 (1H, s), 8.06-8.15 (1H, m), 8.31 (1H, dd, J=4.77, 1.26 Hz), 8.73 (1H, d, J=2.26 Hz), 10.50 (1H, s).

Example 40

2-[(Phenylmethyl)oxy]-4-(1-piperidinylcarbonyl)-N-4-pyridazinyl-5-(trifluoromethyl)benzamide (E40)

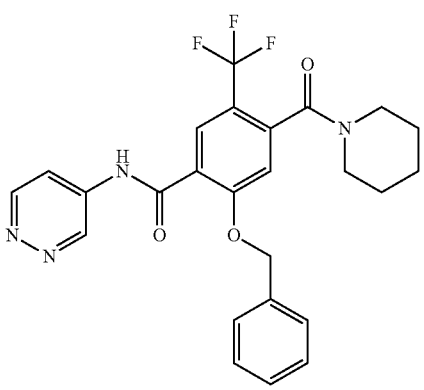 [SMILES: O=C(Nc1ccnnc1)c1cc(C(F)(F)F)c(C(=O)N2CCCCC2)cc1OCc1ccccc1]

2-[(Phenylmethyl)oxy]-4-(1-piperidinylcarbonyl)-5-(trifluoromethyl)benzoic acid (may be prepared as described in Description 58; 70 mg, 0.17 mmol) was dissolved in N,N-dimethylformamide (4 ml). Diisopropylethylamine (0.06 ml, 0.34 mmol) and HATU (131 mg, 0.34 mmol) were added. The mixture was stirred for 5 minutes then 4-pyridazinamine (32.7 mg, 0.34 mmol) was added. The solution was stirred for 90 minutes. The solvent was removed in vacuo and the residue purified by MDAP to give the title compound as a white solid. 30 mg.

MS (electrospray): m/z [M+H]$^+$485

$^1$H NMR (DMSO-d$_6$): 1.20-1.72 (6H, m), 2.97-3.10 (2H, m), 3.45-3.73 (2H, m), 5.36 (2H, s), 7.23-7.43 (5H, m), 7.48 (2H, d, J=6.78 Hz), 7.91-8.10 (2H, m), 9.08 (1H, d, J=5.77 Hz), 9.27 (1H, d, J=1.76 Hz), 10.94 (1H, br. s.).

Example 41

5-Chloro-4-[(3,3-difluoro-1-pyrrolidinyl)carbonyl]-2-[(phenylmethyl)oxy]-N-3-pyridinylbenzamide (E41)

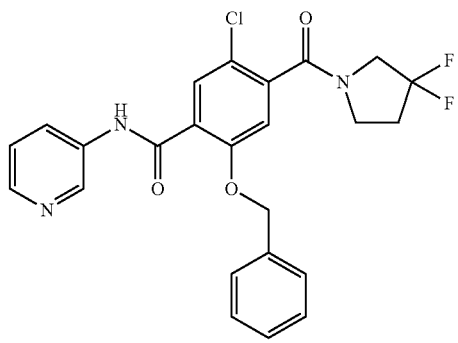 [SMILES: O=C(Nc1cccnc1)c1cc(Cl)c(C(=O)N2CCC(F)(F)C2)cc1OCc1ccccc1]

To a solution of 5-chloro-4-[(3,3-difluoro-1-pyrrolidinyl)carbonyl]-2-[(phenylmethyl)oxy]benzoic acid (may be prepared as described in Description 65; 90 mg, 0.23 mmol) in N,N-dimethylformamide (3 ml) was added diisopropylethylamine (0.08 ml, 0.46 mmol), HATU (156 mg, 0.41 mmol) and 3-aminopyridine (25.7 mg, 0.27 mmol). The solution was stirred for 18 hours. The solvent removed in vacuo to give a gum. Purification by MDAP gave the title compound as a white solid. 65 mg.

MS (electrospray): m/z [M+H]$^+$472

$^1$H NMR (DMSO-d$_6$): 2.41-2.60 (2H, m), 3.39 (1H, t, J=7.40 Hz), 3.59 (1H, t, J=12.42 Hz), 3.75 (1H, t, J=7.53 Hz), 3.93 (1H, t, J=13.18 Hz), 5.28 (2H, s), 7.26-7.43 (5H, m), 7.49 (2H, d, J=6.53 Hz), 7.77 (1H, d, J=2.01 Hz), 8.09 (1H, d, J=8.78 Hz), 8.30 (1H, dd, J=4.77, 1.25 Hz), 8.71 (1H, d, J=2.26 Hz), 10.48 (1H, d, J=8.03 Hz).

Example 42

5-Chloro-4-[(3,3-difluoro-1-pyrrolidinyl)carbonyl]-2-[(phenylmethyl)oxy]-N-4-pyridazinylbenzamide (E42)

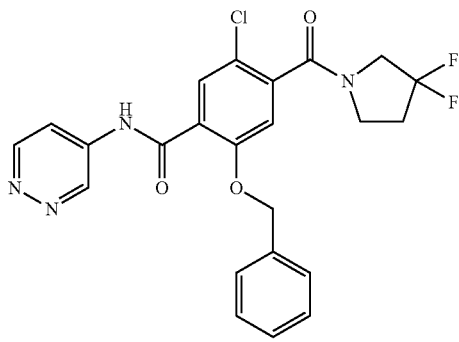 [SMILES: O=C(Nc1ccnnc1)c1cc(Cl)c(C(=O)N2CCC(F)(F)C2)cc1OCc1ccccc1]

To a solution of 5-chloro-4-[(3,3-difluoro-1-pyrrolidinyl)carbonyl]-2-[(phenylmethyl)oxy]benzoic acid (may be prepared as described in Description 65; 90 mg, 0.23 mmol) in N,N-dimethylformamide (3 ml) was added diisopropylethylamine (0.08 ml, 0.46 mmol), HATU (156 mg, 0.41 mmol) and 4-pyridazinamine (26.0 mg, 0.27 mmol). The solution was stirred for 18 hours. The solvent removed in vacuo and purified by MDAP to give the title compound as a white solid. 68 mg.

MS (electrospray): m/z [M+H]$^+$473

$^1$H NMR (DMSO-d$_6$): 2.40-2.60 (2H, m), 3.37-3.43 (1H, m), 3.52-3.67 (1H, m), 3.75 (1H, t, J=7.53 Hz), 3.93 (1H, t, J=13.05 Hz), 5.27 (2H, s), 7.29-7.45 (5H, m), 7.47 (1H, s), 7.78 (1H, d, J=3.01 Hz), 8.01 (1H, dd, J=5.77, 2.51 Hz), 9.08 (1H, d, J=5.77 Hz), 9.26 (1H, d, J=1.51 Hz), 10.92 (1H, br. s.).

Example 43

5-Chloro-4-[(3,3-difluoro-1-pyrrolidinyl)carbonyl]-N-(3-methyl-4-isoxazolyl)-2-[(phenylmethyl)oxy]benzamide (E43)

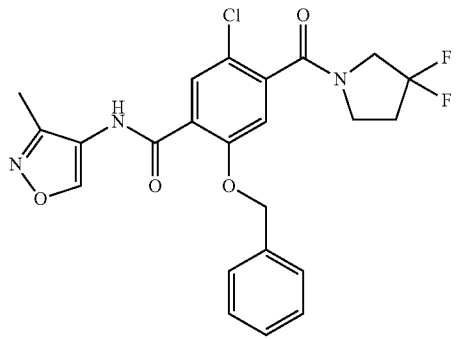 [SMILES: Cc1nocc1NC(=O)c1cc(Cl)c(C(=O)N2CCC(F)(F)C2)cc1OCc1ccccc1]

To a solution of 5-chloro-4-[(3,3-difluoro-1-pyrrolidinyl)carbonyl]-2-[(phenylmethyl)oxy]benzoic acid (may be prepared as described in Description 65; 90 mg, 0.23 mmol) in N,N-dimethylformamide (3 ml) was added diisopropylethylamine (0.08 ml, 0.46 mmol), HATU (156 mg, 0.41 mmol) and 3-methyl-4-isoxazolamine (26.8 mg, 0.27 mmol). The solution was stirred for 18 hours. The solvent removed in vacuo and purified by MDAP to give the title compound as a white solid. 65 mg.

MS (electrospray): m/z [M+H]$^+$476

$^1$H NMR (DMSO-d$_6$): 1.94 (3H, d, J=3.26 Hz), 2.40-2.60 (2H, m), 3.40 (1H, t, J=7.28 Hz), 3.54-3.68 (1H, m), 3.75 (1H, t, J=7.53 Hz), 3.93 (1H, t, J=13.18 Hz), 5.28 (2H, s), 7.32-7.45 (4H, m), 7.51 (2H, d, J=6.78 Hz), 7.81 (1H, s), 9.16 (1H, s), 9.97 (1H, br. s.).

Example 44

5-Chloro-4-(4-morpholinylcarbonyl)-2-[(phenylmethyl)oxy]-N-3-pyridinylbenzamide (E44)

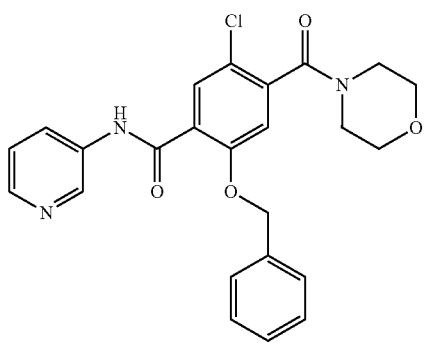 [SMILES: O=C(Nc1cccnc1)c1cc(Cl)c(C(=O)N2CCOCC2)cc1OCc1ccccc1]

To a solution of 5-chloro-4-(4-morpholinylcarbonyl)-2-[(phenylmethyl)oxy]benzoic acid (may be prepared as described in Description 67; 90 mg, 0.24 mmol) in N,N-dimethylformamide (3 ml) was added diisopropylethylamine (0.08 ml, 0.48 mmol), HATU (164 mg, 0.43 mmol) and 3-aminopyridine (27.0 mg, 0.29 mmol). The solution was stirred for 72 hours. The solvent removed in vacuo and purified by MDAP to give the title compound as a white solid. 55 mg.

MS (electrospray): m/z [M+H]$^+$452

$^1$H NMR (DMSO-d$_6$): 3.14 (2H, t, J=4.52 Hz), 3.54 (2H, t, J=3.51 Hz), 3.62-3.72 (4H, m), 5.21-5.33 (2H, m), 7.29-7.41 (5H, m), 7.49 (2H, d, J=6.53 Hz), 7.74 (1H, s), 8.05-8.14 (1H, m), 8.30 (1H, dd, J=4.52, 1.25 Hz), 8.71 (1H, d, J=2.51 Hz), 10.47 (1H, s).

Example 45

5-Chloro-N-(3-chlorophenyl)-4-(4-morpholinylcarbonyl)-2-[(phenylmethyl)oxy]benzamide (E44)

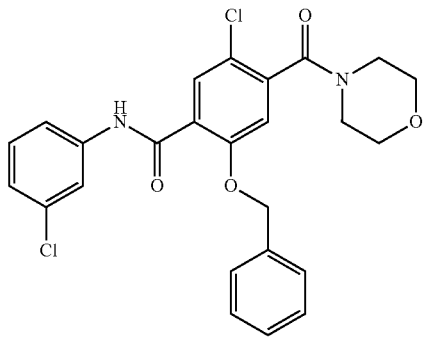 [SMILES: O=C(Nc1cccc(Cl)c1)c1cc(Cl)c(C(=O)N2CCOCC2)cc1OCc1ccccc1]

To a solution of 5-chloro-4-(4-morpholinylcarbonyl)-2-[(phenylmethyl)oxy]benzoic acid (may be prepared as described in Description 67; 90 mg, 0.24 mmol) in N,N-dimethylformamide (3 ml) was added diisopropylethylamine (0.08 ml, 0.48 mmol), HATU (164 mg, 0.43 mmol) and 3-chloroaniline (0.03 ml, 0.29 mmol). The solution was stirred for 2 hours and the solvent removed in vacuo. The residue was purified by column chromatography (SiO$_2$, (solute, 1:1 ethyl acetate/cyclohexane) to yield the title compound as a white solid. 55 mg.

MS (electrospray): m/z [M+H]$^+$485/487

$^1$H NMR(CHLOROFORM-d): 3.18-3.43 (2H, m), 3.56-3.69 (1H, m), 3.70-3.86 (4H, m), 3.88-4.00 (1H, m), 5.16-5.27 (2H, m), 7.03 (1H, d, J=7.78 Hz), 7.08-7.20 (4H, m), 7.53 (5H, s), 8.35 (1H, s), 9.85 (1H, s).

Example 46

5-Chloro-4-(4-morpholinylcarbonyl)-2-[(phenylmethyl)oxy]-N-4-pyridazinylbenzamide (E46)

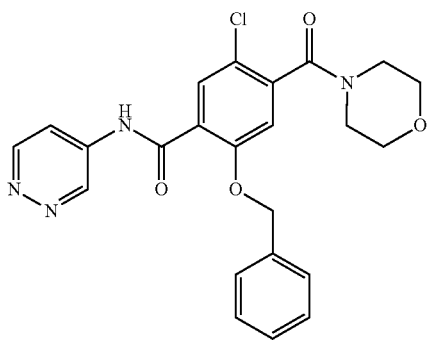 [SMILES: O=C(Nc1ccnnc1)c1cc(Cl)c(C(=O)N2CCOCC2)cc1OCc1ccccc1]

To a solution of 5-chloro-4-(4-morpholinylcarbonyl)-2-[(phenylmethyl)oxy]benzoic acid (may be prepared as described in Description 67; 90 mg, 0.24 mmol) in N,N-dimethylformamide (3 ml) was added diisopropylethylamine (0.08 ml, 0.48 mmol), HATU (164 mg, 0.43 mmol) and 4-aminopyridazine (26.8 mg, 0.29 mmol). The solution was stirred for 2 hours and the solvent removed in vacuo. The residue was purified by column chromatography (SiO$_2$, Isolute, 1:1 ethyl acetate/cyclohexane) to give the title compound as a white solid. 71 mg.

MS (electrospray): m/z [M+H]$^+$453

$^1$H NMR (DMSO-d$_6$): 3.13 (2H, t, J=4.77 Hz), 3.51-3.59 (2H, m), 3.62-3.73 (4H, m), 5.25 (2H, d, J=4.02 Hz), 7.27-7.41 (4H, m), 7.42-7.52 (2H, m), 7.74 (1H, s), 8.00 (1H, dd, J=5.77, 2.76 Hz), 9.07 (1H, d, J=5.77 Hz), 9.24 (1H, d, J=1.76 Hz).

Example 47

2-((4-fluorobenzyl)oxy)-N-(3-fluorophenyl)-5-(1-methyl-1H-pyrazol-4-yl)-4-(morpholine-4-carbonyl)benzamide (E47)

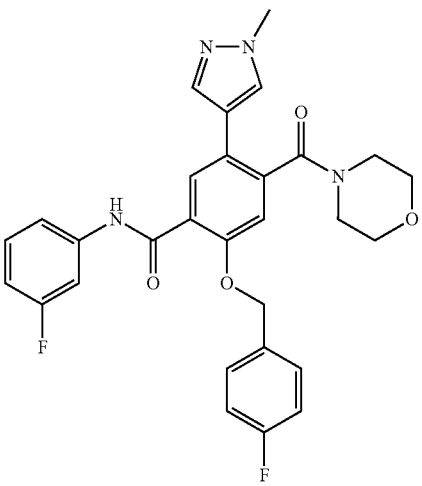 [SMILES: Cn1cc(-c2cc(C(=O)Nc3cccc(F)c3)c(OCc3ccc(F)cc3)cc2C(=O)N2CCOCC2)cn1]

To a solution of 2-((4-fluorobenzyl)oxy)-5-(1-methyl-1H-pyrazol-4-yl)-4-(morpholine-4-carbonyl)benzoic acid (150 mg, 0.341 mmol) (may be prepared as described in description D68) in N,N-Dimethylformamide (DMF) (3 mL), was added EDC (98 mg, 0.512 mmol), 1-hydroxy-7-azabenzotriazole (55.8 mg, 0.410 mmol), DIPEA (0.119 mL, 0.683 mmol) 3-fluoroaniline (0.049 mL, 0.512 mmol) and the mixture was stirred at room temperature overnight. The organics were evaporated and the residue was purified using the MDAP to give the title compound. Yield: 85 mg MS (electrospray): m/z [M+H]+533

$^1$H NMR (400 MHz, CHLOROFORM-d) ppm 2.85-3.19 (3H, m) 3.40-3.66 (2H, m) 3.65-3.90 (3H, m) 3.94-4.07 (3H, m) 5.28 (2H, s) 6.74-6.87 (2H, m) 7.14 (1H, s) 7.17-7.30 (3H, m) 7.31-7.42 (1H, m) 7.57 (2H, dd, J=8.28, 5.27 Hz) 7.66 (1H, s) 7.74 (1H, s) 8.41 (1H, s) 9.93 (1H, s)

Example 48

N-(3-chlorophenyl)-2-((4-fluorobenzyl)oxy)-5-(1-methyl-1H-pyrazol-4-yl)-4-(morpholine-4-carbonyl)benzamide (E48)

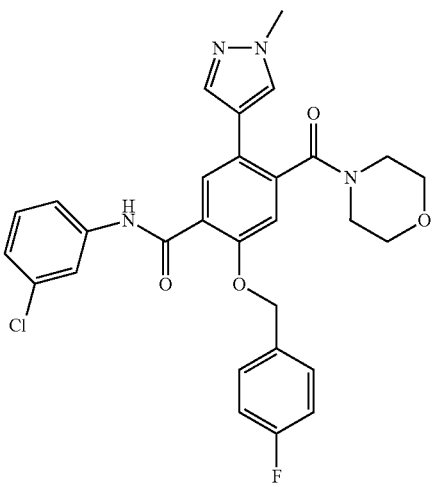 [SMILES: Cn1cc(-c2cc(C(=O)Nc3cccc(Cl)c3)c(OCc3ccc(F)cc3)cc2C(=O)N2CCOCC2)cn1]

To a solution of 2-((4-fluorobenzyl)oxy)-5-(1-methyl-1H-pyrazol-4-yl)-4-(morpholine-4-carbonyl)benzoic acid (150 mg, 0.341 mmol) (may be prepared as described in description D68) in N,N-Dimethylformamide (DMF) (3 mL), was added EDC (98 mg, 0.512 mmol), 1-hydroxy-7-azabenzotriazole (55.8 mg, 0.410 mmol), DIPEA (0.119 mL, 0.683 mmol) 3-chloroaniline (0.054 mL, 0.512 mmol) and the mixture was stirred at room temperature overnight. The organics were evaporated and the residue was purified using the MDAP to give the title compound. Yield: 58 mg MS (electrospray): m/z [M+H]+549

$^1$H NMR (400 MHz, CHLOROFORM-d) ppm 2.80-3.15 (3H, m) 3.57 (2H, d, J=10.54 Hz) 3.62-3.88 (3H, m) 3.97 (3H, s) 5.23 (2H, s) 6.96-7.12 (2H, m) 7.12-7.30 (6H, m) 7.53 (2H, dd, J=8.53, 5.27 Hz) 7.59-7.73 (2H, m) 8.37 (1H, s)

Example 49

2-(benzyloxy)-N-(3-chlorophenyl)-5-(1-methyl-1H-pyrazol-4-yl)-4-(morpholinomethyl)benzamide (E49)

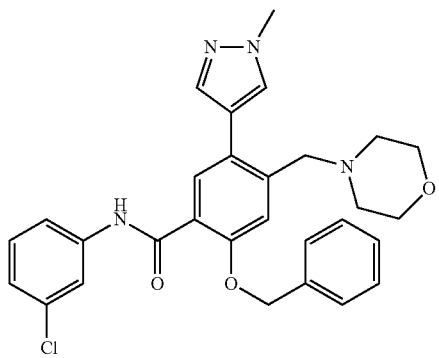 [SMILES: Cn1cc(-c2cc(C(=O)Nc3cccc(Cl)c3)c(OCc3ccccc3)cc2CN2CCOCC2)cn1]

To a solution of 2-(benzyloxy)-5-bromo-N-(3-chlorophenyl)-4-(morpholinomethyl)benzamide (400 mg, 0.775 mmol) (may be prepared as described in description D68) in 1,4-Dioxane (5 mL) in a microwave vial was added Tetrakis (53.8 mg, 0.047 mmol), sodium carbonate (1.551 mL, 1.551 mmol), the vial was sealed and heated to 130° C. for 30 min under microwave conditions. Mixture was evaporated on a buchi under reduced pressure to give a gum, this was purified using a Companion eluting with 50-100% ethyl acetate/cyclohexane. To give the title compound. Yield: 130 mg MS (electrospray): m/z [M+H]+518.

$^1$H NMR (400 MHz, CHLOROFORM-d) δ ppm 2.38-2.59 (4H, m) 3.54 (2H, s) 3.67-3.78 (4H, m) 3.98 (3H, s) 5.29 (2H, s) 7.01 (1H, d, J=7.53 Hz) 7.14 (1H, t, J=8.28 Hz) 7.21-7.35 (4H, m) 7.47-7.58 (4H, m) 7.61 (1H, s) 7.72 (1H, s) 8.28 (1H, s) 10.02 (1H, s).

$^1$H NMR (400 MHz, DMSO-d6) δ ppm 2.34 (4H, br. s.) 3.41-3.64 (6H, m) 3.88 (3H, s) 5.31 (2H, s) 7.13 (1H, s) 7.25-7.41 (5H, m) 7.46-7.57 (3H, m) 7.66 (2H, d, J=3.01 Hz) 7.76 (1H, br. s.) 7.94 (1H, s) 10.32 (1H, s)

Example 50

2-(benzyloxy)-N-(3-chlorophenyl)-5-(1-methyl-1H-pyrazol-4-yl)-4-(morpholinomethyl)benzamide, Hydrochloride (E50)

To a solution of 2-(benzyloxy)-N-(3-chlorophenyl)-5-(1-methyl-1H-pyrazol-4-yl)-4-(morpholinomethyl)benzamide (43 mg, 0.083 mmol) (may be prepared as described in example 49) in Methanol (3 mL) was added an excess of 1,4-dioxane HCl solution (1 mL, 11.69 mmol) at room temperature. The mixture was stirred at room temperature for 1 hour and evaporated on a buchi under reduced pressure to give a pale yellow solid. The solid was triturated with ether (5 ml) and the solid filtered off to give the title compounds as a pale yellow solid. Yield: 44 mg $^1$H NMR (400 MHz, METHANOL-d4) d ppm 3.02 (2H, br. s.) 3.65 (2H, s) 3.92 (4H, br. s.) 3.97-4.13 (3H, m) 4.54 (2H, s) 5.47 (2H, s) 7.07 (1H, dt, J=6.40, 2.20 Hz) 7.13-7.25 (2H, m) 7.37-7.51 (4H, m) 7.60 (2H, d, J=5.27 Hz) 7.82 (1H, s) 7.90-8.01 (3H, m)

Example 51

2-(benzyloxy)-N-(3-chlorophenyl)-5-(1-methyl-1H-pyrazol-4-yl)-4-(morpholinomethyl)benzamide, Maleic acid salt (E51)

To a solution of 2-(benzyloxy)-N-(3-chlorophenyl)-5-(1-methyl-1H-pyrazol-4-yl)-4-(morpholinomethyl)benzamide (43 mg, 0.083 mmol) (may be prepared as described in example 49) in Methanol (3 mL) was added AH10119 Maleic acid (9.65 mg, 0.083 mmol) and the mixture was stirred at room temperature for 1 hour. The solution was evaporated on a buchi under reduced pressure to give a gum, this was triturated with ether (5 ml) to give the title compound as a white solid. Yield: 34 mg MS (electrospray): m/z [M+H]+518.

$^1$H NMR (400 MHz, DMSO-d6) δ ppm 2.63 (4H, br. s.) 3.65 (4H, br. s.) 3.74-3.96 (5H, m) 5.32 (2H, s) 6.20 (2H, s) 7.13 (1H, d, J=7.03 Hz) 7.26-7.45 (5H, m) 7.45-7.59 (3H, m) 7.66 (2H, s) 7.76 (1H, br. s.) 7.94 (1H, s) 10.35 (1H, s)

Example 52

2-(Benzyloxy)-N-(3-chlorophenyl)-4-(morpholinomethyl)-5-(trifluoromethyl)benzamide (E52)

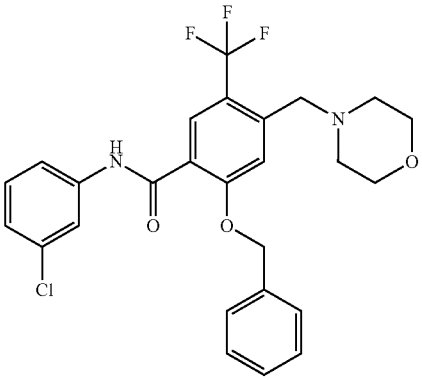 [SMILES: O=C(Nc1cccc(Cl)c1)c1cc(C(F)(F)F)c(CN2CCOCC2)cc1OCc1ccccc1]

To a solution of 2-(benzyloxy)-4-(morpholinomethyl)-5-(trifluoromethyl)benzoic acid (may be prepared as described in description 50, 270 mg, 0.683 mmol) in N,N-Dimethylformamide (DMF) (5 mL) was added DIPEA (0.239 mL, 1.366 mmol), 3-chloroaniline (72.0 μl, 0.683 mmol), 1-hydroxy-7-azabenzotriazole (112 mg, 0.819 mmol) and EDC (262 mg, 1.366 mmol). The solution was stirred for 3 hours then partitioned between EtOAc (20 ml) and water (15 ml). The organic layer was separated, washed further with water (2×20 ml), dried (MgSO4) and the solvent removed. Purification by column (SiO2, Isolute, 3:1-1:1 Cyclohexane/EtOAc) gave the product as a white solid. 205 mg.

MS (electrospray): m/z [M+H]+505
¹H NMR (DMSO-d6): 2.27-2.40 (4H, m), 3.30-3.39 (4H, m), 3.64 (6H, m), 5.36 (2H, s), 7.14 (1H, dd, J=8.03, 1.25 Hz), 7.27-7.43 (4H, m), 7.52 (3H, d, J=6.78 Hz), 7.60 (1H, s), 7.73 (1H, s), 7.93 (1H, s), 10.37 (1H, s).

Example 53

2-(Benzyloxy)-N-(3-fluorophenyl)-4-(morpholinomethyl)-5-(trifluoromethyl)benzamide (E53)

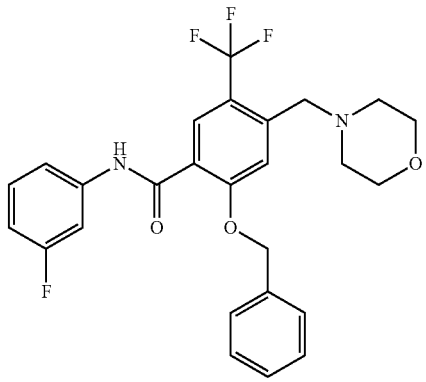 [SMILES: O=C(Nc1cccc(F)c1)c1cc(C(F)(F)F)c(CN2CCOCC2)cc1OCc1ccccc1]

To a solution of 2-(benzyloxy)-4-(morpholinomethyl)-5-(trifluoromethyl)benzoic acid (270 mg, 0.683 mmol) in N,N-Dimethylformamide (DMF) (5 mL) was added DIPEA (0.239 mL, 1.366 mmol), 3-fluoroaniline (0.086 mL, 0.888 mmol), 1-hydroxy-7-azabenzotriazole (112 mg, 0.819 mmol) and EDC (262 mg, 1.366 mmol). The solution was stirred for 3 hours then partitioned between EtOAc (20 ml) and water (15 ml). The organic layer was separated, washed further with water (2×20 ml), dried (MgSO4) and the solvent removed. Purification by column (SiO₂, Isolute 3:1-1:1 Cyclohexane/EtOAc) gave the product as a white solid. 133 mg.

MS (electrospray): m/z [M+H]⁺489
¹H NMR (CHLOROFORM-d): 2.46-2.59 (4H, m), 3.62-3.83 (6H, m), 5.33 (2H, s), 6.70-6.82 (1H, m), 6.82-6.92 (1H, m), 7.10-7.23 (2H, m), 7.47-7.60 (5H, m), 7.71 (1H, s), 8.62 (1H, s), 9.89 (1H, br. s.).

Example 54

2-(benzyloxy)-5-chloro-4-(4-methylpiperazine-1-carbonyl)-N-(pyridin-3-yl)benzamide (E54)

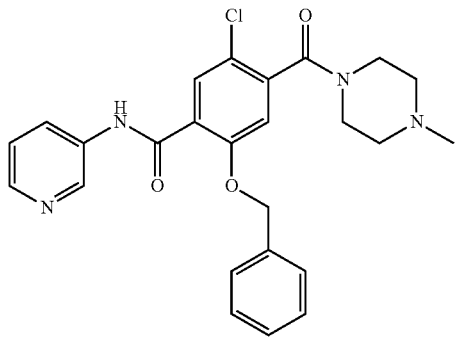

To a solution of 2-(benzyloxy)-5-chloro-4-(4-methylpiperazine-1-carbonyl)benzoic acid (may be prepared as described in D 76) (108 mg, 0.278 mmol) in N,N-dimethylformamide (DMF) (5 mL) was added DIPEA (0.97 ml, 0.555 mmol), 3-aminopyridine (39.2 mg, 0.417 mmol) and 1-hydroxy-7-azabenzotriazole (HOAt) (45 mg, 0333 mmol) and EDC (96 mg, 0.5 mmol). The solution was stirred overnight. The solvent was removed in vacuo and the residue was purified by MDAP (tartan, High pH, 25 minute run) to give a white solid (33 mg, 9% yield).

¹H NMR (400 MHz, CDCl₃): 2.21 (3H, s), 2.24-2.26 (2H, m), 2.38-2.41 (2H, m), 3.11-3.14 (2H, m), 3.63-3.67 (2H, m), 5.27 (2H, s), 7.30-7.37 (5H, m), 7.48-7.50 (2H, m), 7.73 (1H, s), 8.08-8.10 (1H, m), 8.29-8.30 (1H, m), 8.69-8.72 (1H, m), 10.44 (1H, s).

LCMS: MH⁺=465.3

Example 55

2-(benzyloxy)-5-chloro-4-(4-methylpiperazine-1-carbonyl)-N-(pyridazin-4-yl)benzamide (E55)

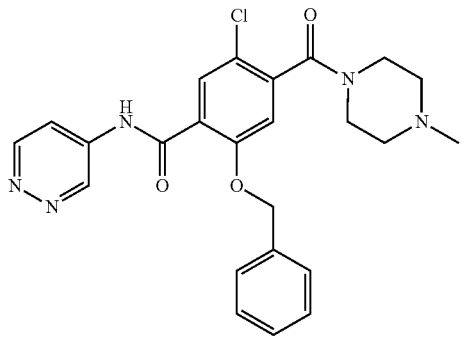 [SMILES: CN1CCN(C(=O)c2cc(OCc3ccccc3)c(C(=O)Nc3ccnnc3)cc2Cl)CC1]

Example 55 may be prepared according to procedures described in Example 54 using different starting material with modifications known to one skilled in the art.

¹H NMR (400 MHz, CDCl₃): 2.21 (3H, s), 2.24-2.28 (2H, m), 2.37-2.40 (2H, m), 3.12-3.13 (2H, m), 3.65-3.66 (2H, m), 5.26 (2H, s), 7.31-7.39 (5H, m), 7.46-7.48 (1H, m), 7.75 (1H, s), 8.01-8.303 (1H, m), 9.09 (1H, d, J=4), 9.27 (1H, d, J=4), 10.93 (1H, s).

LCMS: MH⁺=466.3

Example 56

2-(benzyloxy)-5-chloro-4-(4-methylpiperazine-1-carbonyl)-N-(pyridazin-3-yl)benzamide (E56)

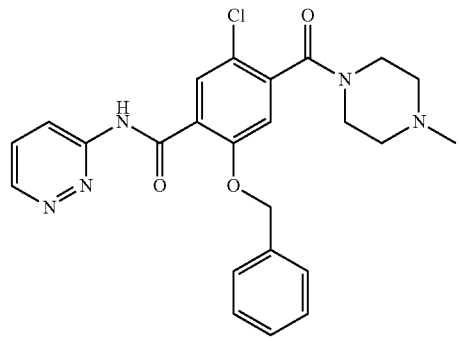 [SMILES: CN1CCN(C(=O)c2cc(OCc3ccccc3)c(C(=O)Nc3cccnn3)cc2Cl)CC1]

Example 56 may be prepared according to procedures described in Example 54 by using different starting material with modifications known to one skilled in the art.

$^1$H NMR (400 MHz, CDCl$_3$): 2.20 (3H, s), 2.23-2.25 (2H, m), 2.36-2.41 (2H, m), 3.11-3.13 (2H, m), 3.63-3.67 (2H, m), 5.33 (2H, s), 7.30-7.35 (4H, m), 7.49-7.50 (2H, m), 7.74-7.76 (1H, m), 7.80 (1H, s), 8.41-8.43 (1H, m), 9.01-9.03 (1H, m), 11.28 (1H, s).

LCMS: MH$^+$=466.2

Example 57

2-(benzyloxy)-5-chloro-4-(4-methylpiperazine-1-carbonyl)-N-phenylbenzamide (E57)

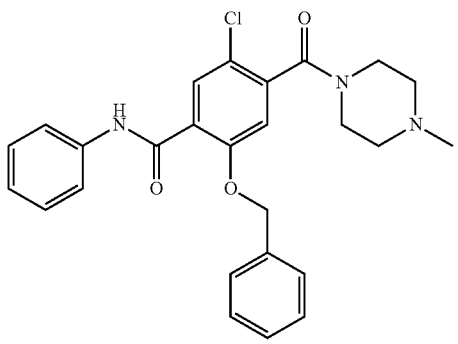 [SMILES: CN1CCN(C(=O)c2cc(OCc3ccccc3)c(C(=O)Nc3ccccc3)cc2Cl)CC1]

Example 57 may be prepared according to procedures described in Example 54 by using different starting material with modifications known to one skilled in the art.

$^1$H NMR (400 MHz, CDCl$_3$): 3.14-3.16 (2H, m), 3.54-3.56 (2H, m), 3.66-3.69 (4H, m), 5.27 (2H, s), 7.06-7.10 (1H, m), 7.29-7.38 (6H, m), 7.51 (2H, d, J=4), 7.58 (2H, d, J=8), 7.73 (1H, s), 10.23 (1H, s).

LCMS: MH$^+$=451.2

Biological Data

As stated above, the compounds of present invention are LRRK2 inhibitors, and are useful in the treatment of diseases mediated by LRRK2. The biological activities of the compounds of present invention can be determined using any suitable assay for determining the activity of a candidate compound as a LRRK2 inhibitor, as well as tissue and in vivo models.

Production of 6His-Tev-LRRK2 (1326-2527)

A LRRK2 cDNA encoding residues 1326-2527 was received from Dundee University (described in M. Jaleel et al., 2007, Biochem J, 405: 407-417). This gene fragment was subcloned into pFB-HTb (Invitrogen) using BamHI and NotI restriction sites. The LRRK2 plasmid was recombined into the baculovirus genome according to the BAC-to-BAC protocol described by Invitrogen. Transfection into *Spodoptera frugiperda* (Sf9) insect cells was performed using Cellfectin (Invitrogen), according to the manufacturer's protocol.

Sf9 cells were grown in Excell 420 (SAFC Biosciences) growth media at 27° C., 80 rpm in shake flask until of a sufficient volume to inoculate a bioreactor. The cells were grown in a 100 liter working volume bioreactor (Applikon) at 27° C., 40% dissolved oxygen and an agitation rate of 60-150 rpm until the required volume was achieved with a cell concentration of approximately 4xe6 cells/ml. The insect cells were infected with Baculovirus at a multiplicity of infection (MOI) of 3. The cultivation was continued for a 48 hour expression phase. The infected cells were removed from the growth media by centrifugation at 2500 g using a Viafuge (Carr) continuous centrifuge at a flow rate of 80 liters/hour. The cell pellet was immediately frozen and subsequently supplied for purification.

A 100 g pellet was allowed to thaw in a water bath at 27° C. with 200 ml lysis buffer/buffer A (50 mm Tris-HCl pH8.5, 300 mm NaCl, 1 mm DTT, 10% glycerol, 1 ml/L calbiochem complete protease inhibitor cocktail and benzonase (20 ul/300 ml)) before being dounce homogenised on ice using 20 strokes per 100 ml. The suspension was then centrifuged at 100,000 g for 90 min, at 4° C.

The lysate was decanted from the insoluble pellet and loaded (at 1.5 ml/min over one cycle volume) onto 5 ml hisHP column that had been pre-equilibrated with 10 column volumes buffer A. The column was then washed with 10 column volumes buffer A, 10 column volumes buffer B (buffer A+1M NaCl) and 10 column volumes buffer C (buffer A+20 mm imidazole). The column was then eluted with 15 column volumes buffer D (buffer A+300 mm imidazole) collecting 2.5 ml fractions. All washes and elution were conducted at 2.5 ml/min.

Fractions identified by SDS-PAGE as containing protein of interest were pooled and loaded directly onto a 320 ml SEC Superdex 200 pg column that was pre-equilibrated with buffer E (50 mM Tris-HCl pH8.5, 300 mM NaCl, 10% glycerol, 1 mM DTT). The column was loaded and eluted with 1.2 column volumes buffer E at 3 ml/min collecting 2 ml fractions.

Fractions identified by SDS-PAGE as containing protein of interest were tested for activity.

Production of Biotin-LRRKtide

The peptide (biotin-RLGRDKYKTLRQIRQGNTKQR-OH) was assembled at a 0.2 mM scale using FMOC solid phase peptide synthesis on an ACT 357 MPS automated peptide synthesizer. The resulting crude peptide was cleaved from the resin using a 95: 2.5: 2.5 mix of trifluoroacetic acid: triisopropylsilane: water. The crude cleaved peptide was purified by reverse phase HPLC, eluting with a 5-35% gradient of 0.1% trifluoroacetic acid/acetonitrile in 0.1% trifluoroacetic acid/water.

Production of GST-PS-Moesin (400-577)

A fragment of human moesin (400-577) was amplified by PCR using a full length cDNA clone encoding human moesin (described in M. Jaleel et al., 2007, Biochem J, 405: 407-417) as a template. The fragment was subcloned into pGEX6P1 (Amersham) using BamHI and XhoI restriction sites. The moesin plasmid was transformed into BL21*(DE3) competent cells (Invitrogen) for expression.

The transformed cells were cultured in LB medium (10 g/L tryptone, 5 g/L yeast extract, 10 g/L NaCl) at 37° C. Once the culture had reached an optical density (600 nm) of 0.5, it was induced with 0.1 mM IPTG and cultured at 30° C. for 20 h. The cells were then collected by centrifugation at 4,400 rpm in for 20 mins at 4° C. and the cell pellets were stored at –80° C. 70 g of cell pellet was thawed at room temperature in 280 ml pre-chilled lysis buffer (50 mM Tris-HCl pH 7.5, 1% Triton X-100, 0.27 M Sucrose, 5 mM beta-mercaptoethanol, 1 ml/L Calbiochem complete protease inhibitor cocktail, 500 mM NaCl, 1 mM Sodium orthovanadate, 10 mM sodium 2-glycerophosphate, 50 mM NaF, 5 mM Sodium pyrophosphate, 0.1 mg/L Lysozyme, 0.1 ml/L) for 30 minutes with constant stirring. The suspension was then sonicated in a pyrex beaker in an ice-water bath at 40% amplitude for 5 minutes, using a pulse of 9.9 sec on/9.9 sec off. Following sonication, the lysate was clarified by centrifugation at 100,000 g for 60 min.

Four 5 ml GST-HP columns were connected in series and were pre-equilibrated with 10 column volumes Buffer F (50 mM Tris/HCl pH 7.5, 0.27 M Sucrose, 5 mM beta-mercaptoethanol, 1 ml/L calbiochem complete protease inhibitor, 500 mM NaCl). The clarified lysate was loaded onto the column at 1 ml/min. The non absorbed fraction was retained. The column was then washed with 10 column volumes Buffer F at 3 ml/min (the non-absorbed fraction was retained). The column was then eluted at 2 ml/min using Buffer G (Buffer F plus 20 mM reduced glutathione) collecting 10 ml fractions. Fractions containing protein of interest were identified using SDS-PAGE and pooled.

A 500 ml SEC Superdex 200 pg column was pre-equilibrated in Buffer H (50 mM Tris-HCl pH 6.4, 0.27 M Sucrose, 5 mM Beta-mercaptoethanol. 150 mM NaCl). The pooled fractions were loaded onto the column at 2 ml/min. The column was then eluted over 1.2 column volumes Buffer H at 2 ml/min, collecting 2 ml fractions. Fractions containing protein of interest were identified by SDS-PAGE and pooled and tested for activity.

Compounds of formula (I) may be tested for in vitro kinase activity in accordance with the following assays, using the non natural, in vitro, substrates moesin and the Longer Biotin-LRRKtide. Moesin and a shorter version of the peptide were identified as substrates in Jaleel et al. (2007, Biochem J, 405: 307-317).

LRRK2 Peptide Substrate Assay a) 100 nl of a 1:4 serial dilution of test compound with a top final assay concentration of 30 µM is added to certain wells in a low volume 384 well black plate. 100 nl of DMSO is used in certain wells as controls.

b) 3 µl enzyme solution (80 nM purified recombinant 6His-Tev-LRRK2 (1326-2527) in assay buffer: 50 mM Hepes (pH 7.2), 10 mM $MgCl_2$, 150 mM NaCl, 5% glycerol, 0.0025% triton X-100 and 1 mM DTT) is added to certain wells. 3 µl assay buffer is added to certain wells as a 100% inhibition (no enzyme) control.

c) After incubation at room temperature for 30 minutes, 3 µl substrate solution (2 µM Biotin-LRRKtide peptide substrate and ATP at $K_m$ in assay buffer) is added to each well. Plates are then incubated for a further 1-2 hours at room temperature (incubation time varies depending upon rate and linearity of reaction with differing enzyme batches).

d) 6 µl detection solution (50 nM Streptavidin SureLight® APC (PerkinElmer), 4 nM Eu-W1024 labelled anti-rabbit IgG antibody (PerkinElmer), 1:500 dilution (dilution determined on a batch to batch basis) of Phospho-Ezrin (Thr567)/Radixin (Thr564)/Moesin (Thr558) Polyclonal Antibody (New England Biolabs) and 60 mM EDTA in buffer: 40 mM Hepes (pH 7.2), 150 mM NaCl, 0.03% BSA) is added to each well. Plates are then incubated for a further 2 hours at room temperature before reading on a suitable plate reader (Excitation 330 nm, emission 620 nm (Eu) and 665 nm (APC)). Data is analysed using ActivityBase software (IDBS).

LRRK2 AlphaScreen Desensitised Protein Substrate Assay a) 100 nl of a 1:4 serial dilution of test compound with a top final assay concentration of 30 µM is added to certain wells in a low volume 384 well black plate. 100 nl of DMSO is used in certain wells as controls.

b) 3 µl enzyme solution (80 nM purified recombinant 6His-Tev-LRRK2 (1326-2527) in assay buffer: 50 mM Hepes (pH 7.2), 10 mM $MgCl_2$, 150 mM NaCl, 5% glycerol, 0.0025% triton X-100 and 1 mM DTT) is added to certain wells. 3 µl assay buffer is added to certain wells as a 100% inhibition (no enzyme) control.

c) After incubation at room temperature for 30 minutes, 3 µl substrate solution (200 nM GST-PS-Moesin (400-577) and 2 mM ATP in assay buffer) is added to each well. Plates are then incubated for 20 minutes at room temperature.

d) 6 µl detection solution (1:250 dilution of AlphaLisa Protein A Acceptor beads (PerkinElmer), 1:64 dilution of AlphaLisa Gluthathione Donor beads (PerkinElmer) and 1:600 dilution (dilution determined on a batch to batch basis) of Phospho-Ezrin (Thr567)/Radixin (Thr564)/Moesin (Thr558) Polyclonal Antibody (New England Biolabs) in a buffer: 50 mM Hepes (pH 7.5), 250 mM NaCl, 60 mM EDTA, 1% PEG and 0.01% Brij 35) is added to each well. Plates are then incubated for a further 2 hours at room temperature in the dark before reading on an EnVision™ plate reader with AlphaScreen HTS turbo option module and AlphaScreen settings. Data is analysed using ActivityBase software (IDBS).

Pharmacological Data

Examples 1-13, 14, 17, 18, 20, 22-28 and 31-57 were tested in the LRRK2 peptide substrate assay and/or LRRK2 alphascreen desensitised protein substrate assay or a similar assay described above. The data mentioned below represents a mean pIC 50 value of multiple test results. It is understood that the data illustrated below may have reasonable variation depending on the specific conditions and procedures used by the person conducting the testing.

The compounds of examples 1-13, 14, 17, 18, 20, 23-28, and 31-57 were tested in the LRRK2 peptide substrate assay and exhibited a pIC50≥5.9. The compounds of examples 1-13, 17, 18, 20, 23, 25-27, 31-33, 37, 39, 41-51 and 53-57 were tested in the LRRK2 peptide substrate assay and exhibited a pIC50≥7.0. The compounds of examples 2, 5, 6, 9-12, 31, 45, 47, 48 and 53 were tested in the LRRK2 peptide substrate assay and exhibited a pIC50≥8.0.

The compound of example 22 was tested in the LRRK2 peptide substrate assay and exhibited a pIC50<4.6.

The compounds of examples 1-14, 17, 18, 20, 22-29, and 31-48 and 54-57 were tested in the LRRK2 alphascreen desensitised protein substrate assay and exhibited a pIC50≥4.6. The compounds of examples 2, 4-7, 9-12, 17, 20, 23, 26, 31-33, 39, 41, 44, 45, 47, 48 and 55 were tested in the LRRK2 alphascreen protein substrate assay and exhibited a pIC50≥6.5.

The compounds of example 49-54 were tested in the LRRK2 alphascreen protein substrate assay and exhibited a pIC50<4.6.

The compounds of examples 2, 4, 7, 9, 10, 11, 12, 13, 17, 18, 20, 23, 27, 31, 32, 37, 39, 42, 44, 47 and 48 were tested in the LRRK2 peptide substrate assay and in the LRRK2 alphascreen desensitised protein substrate assay. Mean pIC50 values for each compound are indicated in the attached table:

| Example No | LRRK2 peptide substrate assay (pIC50) | LRRK2 alphascreen desensitized protein substrate assay (pIC50) |
|---|---|---|
| 2 | 8 | 6.6 |
| 4 | 7.8 | 6.9 |
| 7 | 7.8 | 6.8 |
| 9 | 8 | 6.9 |
| 10 | 8.2 | 7.0 |
| 11 | 8.1 | 7.3 |
| 12 | 8.0 | 7.0 |
| 13 | 7.1 | 6.1 |
| 17 | 7.3 | 6.8 |
| 18 | 7.9 | 6.4 |
| 20 | 7.2 | 6.7 |
| 23 | 7.9 | 6.7 |
| 27 | 7.3 | 5.8 |
| 31 | 8.2 | 7.3 |
| 32 | 7.3 | 6.7 |

-continued

| Example No | LRRK2 peptide substrate assay (pIC50) | LRRK2 alphascreen desensitized protein substrate assay (pIC50) |
|---|---|---|
| 37 | 7.4 | 6.1 |
| 39 | 7.8 | 6.5 |
| 42 | 7.3 | 6.3 |
| 44 | 7.5 | 6.8 |
| 47 | 8.0 | 6.9 |
| 48 | 8.2 | 7.8 |

The invention claimed is:

1. A compound of formula (I) or a salt thereof:

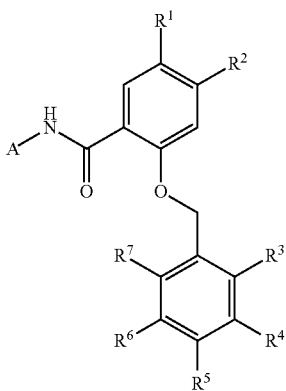

(I)

wherein:
A represents pyridin-2-yl, pyridin-3-yl, pyridazin-3-yl, pyridazin-4-yl, pyrimidin-5-yl, 1,3-oxazol-2-yl, 1H-pyrazol-4-yl or isoxazol-4-yl or a group of formula (a) wherein * represents the point of attachment:

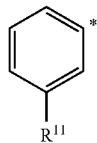

(a)

wherein when A represents pyridin-3-yl, the pyridinyl ring may optionally be substituted at the 2 position by fluoro, methoxy or $CH_2OH$, at the 4 position by methyl or $CH_2OH$, or at the 5 position by fluoro; when A represents 1H-pyrazol-4-yl, the pyrazolyl ring may optionally be substituted at the 1 position by methyl, and where A represents isoxazol-4-yl, the isoxazolyl ring may optionally be substituted at the 3 position by methyl or at the 5 position by methyl;
$R^1$ and $R^2$ independently represent halo, $C_{1-3}$ haloalkyl, $—(CH_2)_nR^8$, $—(CO)R^8$, nitrogen containing heteroaryl ring optionally substituted with one, two or three groups selected from methyl and trifluoromethyl:
n represents 1, 2 or 3;
$R^3$, $R^4$, $R^5$, $R^6$ and $R^7$ independently represent hydrogen, halo, CN, $C_{1-3}$alkyl or $C_{1-3}$ alkoxy;
$R^8$ represents hydrogen or $—NR^9R^{10}$; $R^9$ and $R^{10}$ are either independently selected from hydrogen and $C_{1-3}$ alkyl, wherein said $C_{1-3}$ alkyl group is optionally substituted with one, two or three halo, hydroxy, cyano or $C_{1-2}$alkoxy groups, or, together with the nitrogen atom to which they are attached, join together to form a nitrogen containing monoheterocyclic ring which ring is optionally substituted with one, two or three groups selected from halo, methyl and trifluoromethyl; and $R^{11}$ represents hydrogen, halo, CN, $C_{1-2}$alkyl, $C_{1-2}$alkoxy, $—CH_2CO_2H$ or $—CONHCH_3$.

2. A compound of claim 1, wherein A represents pyridin-3-yl, pyridazin-4-yl, 1H-pyrazol-4-yl or isoxazol-4-yl, wherein, where A represents pyridin-3-yl, the pyridinyl ring is optionally substituted at the 2 position by fluoro, wherein A represents 1H-pyrazol-4-yl, the pyrazolyl ring is optionally substituted at the 1 position by methyl and where A represents isoxazol-4-yl, the isoxazolyl ring is optionally substituted at the 3 position by methyl or at the 5 position by methyl.

3. A compound of claim 1, wherein A represents a group of formula (a), and $R_{11}$ is Cl.

4. A compound according to claim 1, wherein $R_1$ represents Br or Cl.

5. A compound according to claim 1, wherein $R_1$ represents methyl.

6. A compound according to claim 1, wherein $R_1$ represents 4-morpholinylcarbonyl.

7. A compound according to claim 1, wherein $R_2$ represents 4-morpholinylmethyl.

8. A compound according to claim 1, wherein $R_2$ represents pyrazol-4-yl optionally substituted with one methyl group.

9. A compound according to claim 1, wherein $R_2$ represents 4-morpholinylcarbonyl.

10. A compound of according to claim 1, wherein $R^3$, $R^4$, $R^5$, $R^6$ and $R^7$ are independently hydrogen or fluoro.

11. A compound according to claim 1, wherein $R_1$ represents 4-morpholinylmethyl.

12. A pharmaceutical composition which comprises the compound of formula (I) as defined in claim 1, or a pharmaceutically acceptable salt thereof and a pharmaceutically acceptable carrier or excipient.

13. A method of treatment of Parkinson's disease which comprises administering to a host in need thereof an effective amount of a compound of formula (I) as defined in claim 1 or a pharmaceutically acceptable salt thereof.

14. A method of claim 13, wherein the host is human.

* * * * *